United States Patent
Kimura et al.

(10) Patent No.: US 9,777,219 B2
(45) Date of Patent: Oct. 3, 2017

(54) LIQUID CRYSTAL COMPOUND HAVING TETRACYCLE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Keiji Kimura, Chiba (JP); Takahiro Kobayashi, Tokyo (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 15/155,170

(22) Filed: May 16, 2016

(65) Prior Publication Data
US 2016/0340584 A1    Nov. 24, 2016

(30) Foreign Application Priority Data

May 19, 2015 (JP) .................................. 2015-101444

(51) Int. Cl.

| | |
|---|---|
| G02F 1/1333 | (2006.01) |
| C09K 19/34 | (2006.01) |
| C09K 19/30 | (2006.01) |
| C07C 43/225 | (2006.01) |
| C07C 43/192 | (2006.01) |
| C07C 323/19 | (2006.01) |
| C07C 69/757 | (2006.01) |
| C07C 69/76 | (2006.01) |
| C09K 19/32 | (2006.01) |
| C09K 19/04 | (2006.01) |

(52) U.S. Cl.
CPC ........ *C09K 19/3458* (2013.01); *C07C 43/192* (2013.01); *C07C 43/225* (2013.01); *C07C 69/757* (2013.01); *C07C 69/76* (2013.01); *C07C 323/19* (2013.01); *C09K 19/3066* (2013.01); *C09K 19/3068* (2013.01); *C09K 19/32* (2013.01); *C09K 19/3402* (2013.01); *C07C 2601/14* (2017.05); *C09K 2019/0466* (2013.01); *C09K 2019/308* (2013.01); *C09K 2019/3071* (2013.01); *C09K 2019/3077* (2013.01); *C09K 2019/3083* (2013.01); *C09K 2019/3422* (2013.01); *C09K 2019/3425* (2013.01)

(58) Field of Classification Search
CPC ............ C09K 19/3458; C09K 19/3068; C09K 19/3066; C09K 19/3402; C09K 19/32; C09K 2019/3077; C09K 2019/308; C09K 2019/3083; C09K 2019/3422; C09K 2019/3071; C09K 2019/0466; C09K 2019/3425; C07C 43/225; C07C 43/192; C07C 323/19; C07C 2601/14; C07C 69/757; C07C 69/76

USPC .......................... 252/299.01, 299.61; 428/1.1
See application file for complete search history.

(56) References Cited

U.S. PATENT DOCUMENTS

| | | |
|---|---|---|
| 5,728,319 A | 3/1998 | Matsui et al. |
| 6,007,740 A | 12/1999 | Andou et al. |
| 8,603,359 B2 * | 12/2013 | Kubo ................... C07D 213/30 252/299.01 |

FOREIGN PATENT DOCUMENTS

CN    103333139    10/2013

\* cited by examiner

*Primary Examiner* — Geraldina Visconti
(74) *Attorney, Agent, or Firm* — Wenderoth, Lind & Ponack, L.L.P.

(57) ABSTRACT

A problem is to provide a liquid crystal compound satisfying at least one physical property such as high stability to heat and light, a high clearing point (or high maximum temperature), a low minimum temperature of a liquid crystal phase, small viscosity, suitable optical anisotropy, large dielectric anisotropy, a suitable elastic constant and excellent compatibility with other liquid crystal compounds, a liquid crystal composition containing the compound and a liquid crystal display device including the composition.

A solution is a compound represented by formula (1).

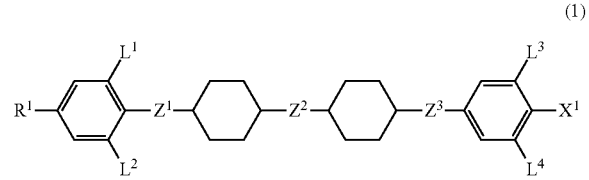

(1)

In which, $R^1$ is alkyl having 1 to 10 carbons or the like; $Z^1$, $Z^2$ and $Z^3$ are independently a single bond, —COO—, —OCH$_2$—, —CF$_2$O— or the like, and at least one of $Z^1$, $Z^2$ and $Z^3$ is —CF$_2$O—; $X^1$ is hydrogen, fluorine, —CF$_3$ or —OCF$_3$; and $L^1$, $L^2$, $L^3$ and $L^4$ are independently hydrogen, fluorine or chlorine.

15 Claims, No Drawings

LIQUID CRYSTAL COMPOUND HAVING TETRACYCLE, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a liquid crystal compound having a $CF_2O$ group, a liquid crystal composition that contains the compound and has a nematic phase, and a liquid crystal display device including the composition.

A liquid crystal display device has been widely used for a display of a personal computer, a television and so forth. The device utilizes physical properties such as an optical anisotropy and a dielectric anisotropy of a liquid crystal compound. As an operating mode of the liquid crystal display device, such a mode exists as a phase change (PC) mode, a twisted nematic (TN) mode, a super twisted nematic (STN) mode, abistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the device, the liquid crystal compound contained in the composition preferably has physical properties described in (1) to (8) below: (1) a high stability to heat and light, (2) a high clearing point, (3) a low minimum temperature of a liquid crystal phase, (4) a small viscosity ($\eta$), (5) a suitable optical anisotropy ($\Delta n$), (6) a large dielectric anisotropy ($\Delta\epsilon$), (7) a suitable elastic constant (K) and (8) an excellent compatibility with other liquid crystal compounds.

An effect of physical properties of the liquid crystal compound on the characteristics of the device is as described below. A compound having the high stability to heat and light as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as a nematic phase and a smectic phase as described in (3), in particular, a compound having the low minimum temperature of the nematic phase, also extends a temperature range in which the device can be used. A compound having the small viscosity as described in (4) decreases a response time of the device.

According to a design of the device, a compound having a suitable optical anisotropy, more specifically, a compound having the large optical anisotropy or the small optical anisotropy is required. When the response time is shortened by decreasing a cell gap of the device, a compound having the large optical anisotropy is suitable. A compound having the large dielectric anisotropy as described in (6) decreases a threshold voltage of the device. Thus, an electric power consumption of the device is reduced. On the other hand, a compound having a small dielectric anisotropy shortens the response time of the device by decreasing a viscosity of the composition. The compound extends the temperature range in which the device can be used by increasing a maximum temperature of the nematic phase.

With regard to (7), a compound having a large elastic constant decreases the response time of the device. A compound having a small elastic constant decreases the threshold voltage of the device. Therefore, the suitable elastic constant is required according to the characteristics that are desirably improved. A compound having the excellent compatibility with other liquid crystal compounds as described in (8) is preferred. The reason is that the physical properties of the composition are adjusted by mixing liquid crystal compounds having different physical properties.

A variety of liquid crystal compounds having a large dielectric anisotropy have so far been prepared. A variety of liquid crystal compounds having a large optical anisotropy have also been prepared. The reason is that excellent physical properties that are not found in a conventional compound are expected from a new compound. The reason is because a suitable balance is expected to be obtained between at least two physical properties in the composition by adding the new compound to a liquid crystal composition. In view of such a situation, with regard to the physical properties (1) to (8) described above, a compound having excellent physical properties and a suitable balance has been desired.

Compound (No. 348) described on page 24 of Patent literature No. 1 is as described below. Here, R is alkyl, alkenyl or alkoxy.

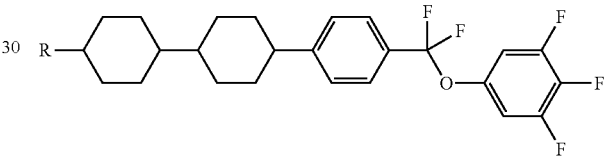

On page 17 of Patent literature No. 3, the following compound is described:

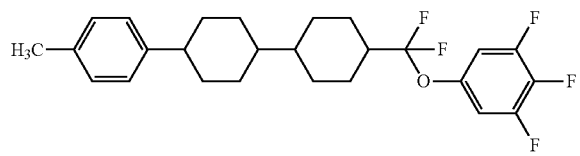

CITATION LIST

Patent Literature

Patent literature No. 1: WO 1996-011897 A.
Patent literature No. 2: JP H10-204016 A.
Patent literature No. 3: CN 10-3333139 A.

SUMMARY OF INVENTION

Technical Problem

A first object is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with other liquid crystal compounds. The object is to provide a compound having an excellent compatibility in comparison with a similar compound. A second object is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The object is to provide a liquid crystal composition having a suitable balance regarding at least two of the physical properties. A third object is to provide a liquid crystal display device including the composition and having a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound and a liquid crystal display device including the composition:

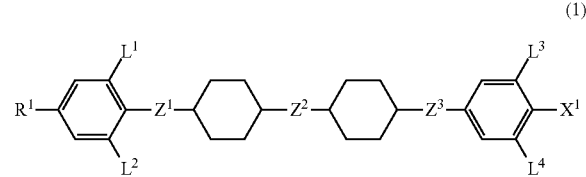

(1)

wherein, in formula (1),
$R^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;
$Z^1$, $Z^2$ and $Z^3$ are independently a single bond, —COO—, —OCH$_2$—, —CF$_2$O—, —CH$_2$CH$_2$—, —CF$_2$CF$_2$—, —CF=CF—, —C≡C—, —(CH$_2$)$_4$— or —CH$_2$CH=CHCH$_2$—, $Z^1$ and $Z^3$ may be independently —CH=CH—, and at least one of $Z^1$, $Z^2$ and $Z^3$ is —CF$_2$O—;
$X^1$ is fluorine, —CF$_3$ or —OCF$_3$;
$L^1$, $L^2$, $L^3$ and $L^4$ are independently hydrogen, fluorine or chlorine; and
when $R^1$ is alkyl, $Z^1$ and $Z^2$ are a single bond, and $Z^3$ is —CF$_2$O—, $R^1$ is alkyl having 3 to 10 carbons.

Advantageous Effects of Invention

A first advantage is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with other liquid crystal compounds. The advantage is to provide the compound having a superior compatibility in comparison with a similar compound (see Comparative Example 1). A second advantage is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The advantage is to provide a liquid crystal composition having a suitable balance regarding at least two of the physical properties. A third advantage is to provide a liquid crystal display device including the composition and having a wide temperature range in which the device can be used, a short response time, a large voltage holding ratio, a low threshold voltage, a large contrast ratio and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but to be added for the purpose of adjusting physical properties of a composition such as a maximum temperature, a minimum temperature, viscosity and a dielectric anisotropy. The compound has a six-membered ring such as 1,4-cyclohexylene and 1,4-phenylene, and has rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. A proportion (content) of the liquid crystal compounds is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer, a dye and an antifoaming agent is added to the composition when necessary. A proportion (amount of addition) of the additive is expressed in terms of weight percent (% by weight) based on the weight of the liquid crystal composition in a manner similar to the proportion of the liquid crystal compounds. Weight parts per million (ppm) may be occasionally used. A proportion of the polymerization initiator or the polymerization inhibitor is exceptionally expressed based on the weight of the polymerizable compound.

"Clearing point" is a transition temperature between a liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as "maximum temperature." "Minimum temperature of the nematic phase" may be occasionally abbreviated as "minimum temperature." An expression "increases the dielectric anisotropy" means that the value positively increases for the composition having a positive dielectric anisotropy, and that the value negatively increases for the composition having a negative dielectric anisotropy.

A compound represented by formula (1) may be occasionally abbreviated as "compound (1)." At least one compound selected from the group of compounds represented by formula (1) may be occasionally abbreviated as "compound (1)." "Compound (1)" means one compound, a mixture of two compounds or a mixture of three or more compounds represented by formula (1). A same rule applies also to any other compound represented by any other formula. In formulas (1) to (15), a symbol $A^1$, $B^1$, $C^1$ or the like surrounded by a hexagonal shape corresponds to ring $A^1$, ring $B^1$, ring $C^1$ or the like, respectively. The hexagonal shape represents a six-membered ring such as cyclohexane or benzene. The hexagonal shape may occasionally represents a condensed ring such as naphthalene or a bridged ring such as adamantane.

A symbol of terminal group $R^1$ is used for a plurality of compounds in chemical formulas of component compounds. In the compounds, two groups represented by two pieces of arbitrary $R^1$ may be identical or different. In one case, for example, $R^1$ of compound (1-1) is ethyl and $R^1$ of compound (1-2) is ethyl. In another case, $R^1$ of compound (1-1) is ethyl and $R^1$ of compound (1-2) is propyl. A same rule applies also to a symbol of $R^1$, $Z^{11}$ or the like. In compound (8), when i is 2, two of rings $D^1$ exists. In the compound, two groups represented by two of rings $D^1$ may be identical or different. A same rule applies also to two of arbitrary rings $D^1$ when i is larger than 2. A same rule applies also to other symbols.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without limitation. A same rule applies also to an expression "at least one piece of 'A' is replaced by 'B'." An expression "at least one piece of 'A' may be replaced by 'B', 'C' or 'D'" includes a case where arbitrary 'A' is replaced by 'B', a case where arbitrary 'A' is replaced by 'C', and a case where arbitrary 'A' is replaced by 'D', and also a case where a plurality of pieces 'A' are replaced by at least two pieces of 'B', 'C' and/or 'D'. For example, "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where replacement of two consecutive pieces of —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Halogen means fluorine, chlorine, bromine and iodine. Preferred halogen is fluorine and chlorine. Further preferred halogen is fluorine. Alkyl of the liquid crystal compound is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule also applies to an asymmetrical divalent group formed by removing two pieces of hydrogen from a ring, such as tetrahydropyran-2,5-diyl.

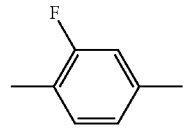

(L)

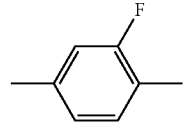

(R)

The invention includes items described below.

Item 1. A compound, represented by formula (1):

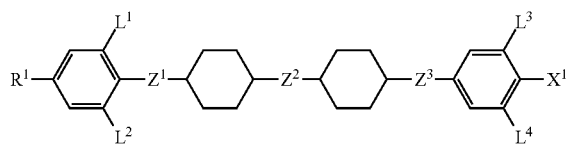

(1)

wherein, in formula (1), $R^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

$Z^1$, $Z^2$ and $Z^3$ are independently a single bond, —COO—, —$OCH_2$—, —$CF_2O$—, —$CH_2CH_2$—, —$CF_2CF_2$—, —CF=CF—, —C≡C—, —$(CH_2)_4$— or —$CH_2CH=CHCH_2$—, $Z^1$ and $Z^3$ may be independently —CH=CH—, and at least one of $Z^1$, $Z^2$ and $Z^3$ is —$CF_2O$—;

$X^1$ is fluorine, —$CF_3$ or —$OCF_3$; and $L^1$, $L^2$, $L^3$ and $L^4$ are independently hydrogen, fluorine or chlorine;

in which, when $R^1$ is alkyl, $Z^1$ and $Z^2$ are a single bond, and $Z^3$ is —$CF_2O$—, $R^1$ is alkyl having 3 to 10 carbons.

Item 2. The compound according to item 1, represented by any one of formulas (1a), (1b) and (1c):

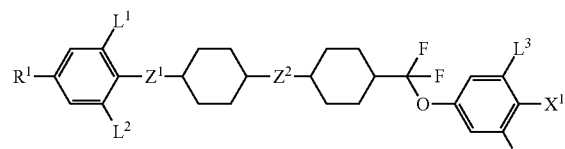

(1a)

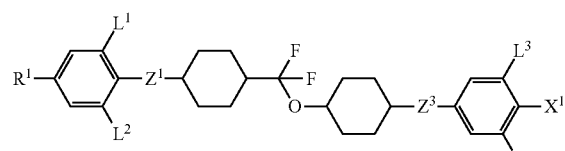

(1b)

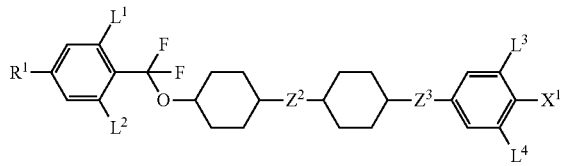
(1c)

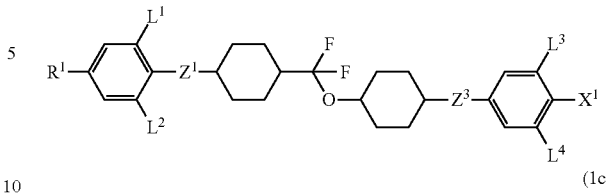
(1b)

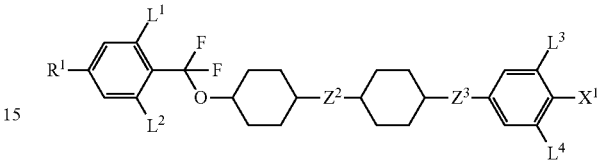
(1c)

wherein, in formulas (1a), (1b) and (1c),

R$^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

Z$^1$, Z$^2$ and Z$^3$ are independently a single bond, —COO—, —OCH$_2$—, —CF$_2$O—, —CH$_2$CH$_2$—, —CF$_2$CF$_2$—, —CF═CF—, —C≡C—, —(CH$_2$)$_4$— or —CH$_2$CH═CHCH$_2$—, and Z$^1$ and Z$^3$ may be independently —CH═CH—;

X$^1$ is fluorine, —CF$_3$ or —OCF$_3$; and

L$^1$, L$^2$, L$^3$ and L$^4$ are independently hydrogen, fluorine or chlorine;

in which, in formula (1a), when Z$^1$ and Z$^2$ are a single bond, R$^1$ is alkoxy having 1 to 10 carbons or alkenyl having 2 to 10 carbons.

Item 3. The compound according to item 2, wherein, in formulas (1a), (1b) and (1c), R$^1$ is alkenyl having 2 to 10 carbons; Z$^1$, Z$^2$ and Z$^3$ are independently a single bond, —COO—, —OCH$_2$— or —CF$_2$O—; X$^1$ is fluorine, —CF$_3$ or —OCF$_3$; and L$^1$, L$^2$, L$^3$ and L$^4$ are independently hydrogen or fluorine.

Item 4. The compound according to item 2, wherein, in formulas (1a), (1b) and (1c), R$^1$ is alkenyl having 2 to 10 carbons; Z$^1$, Z$^2$ and Z$^3$ are a single bond; X$^1$ is fluorine, —CF$_3$ or —OCF$_3$; and L$^1$, L$^2$, L$^3$ and L$^4$ are independently hydrogen or fluorine.

Item 5. The compound according to item 1 or 2, represented by formula (1a):

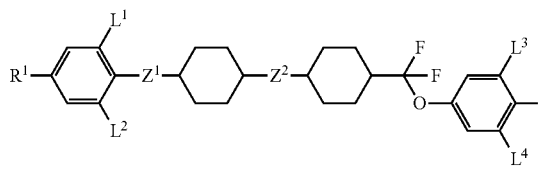
(1a)

wherein, in formula (1a),

R$^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

Z$^1$ is a single bond, —COO—, —OCH$_2$—, —CF$_2$O— or —CH═CH—, and Z$^2$ is a single bond, —COO—, —OCH$_2$— or —CF$_2$O—;

X$^1$ is —CF$_3$ or —OCF$_3$; and

L$^1$, L$^2$, L$^3$ and L$^4$ are independently hydrogen or fluorine.

Item 6. The compound according to item 1 or 2, represented by formula (1b) or (1c):

wherein, in formulas (1b) and (1c),

R$^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

Z$^1$ and Z$^3$ are independently a single bond, —COO—, —OCH$_2$—, —CF$_2$O— or —CH═CH—, and Z$^2$ is a single bond, —COO—, —OCH$_2$— or —CF$_2$O—;

X$^1$ is fluorine, —CF$_3$ or —OCF$_3$; and

L$^1$, L$^2$, L$^3$ and L$^4$ are independently hydrogen or fluorine.

Item 7. The compound according to item 1 or 2, represented by any one of formulas (1d), (1e) and (1f):

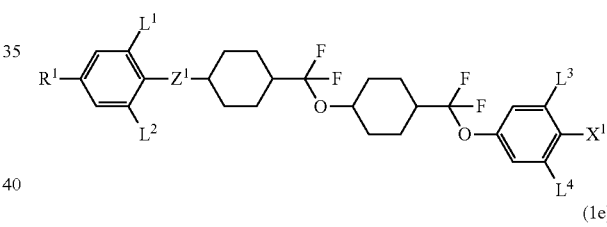
(1d)

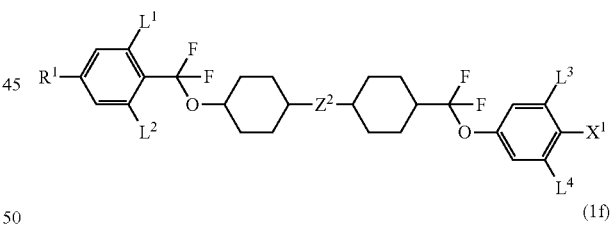
(1e)

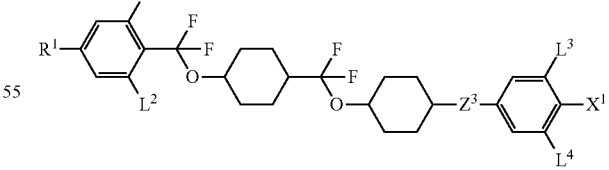
(1f)

wherein, in formulas (1d), (1e) and (1f),

R$^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

Z$^1$ and Z$^3$ are independently a single bond, —COO—, —OCH$_2$—, —CF$_2$O—, —CH$_2$CH$_2$— or —CH═CH—, and Z$^2$ is a single bond, —COO—, —OCH$_2$— or —CH$_2$CH$_2$—;

$X^1$ is fluorine, —$CF_3$ or —$OCF_3$; and $L^1$, $L^2$, $L^3$ and $L^4$ are independently hydrogen, fluorine or chlorine.

Item 8. The compound according to item 1 or 2, represented by any one of formulas (1g), (1h) and (1i):

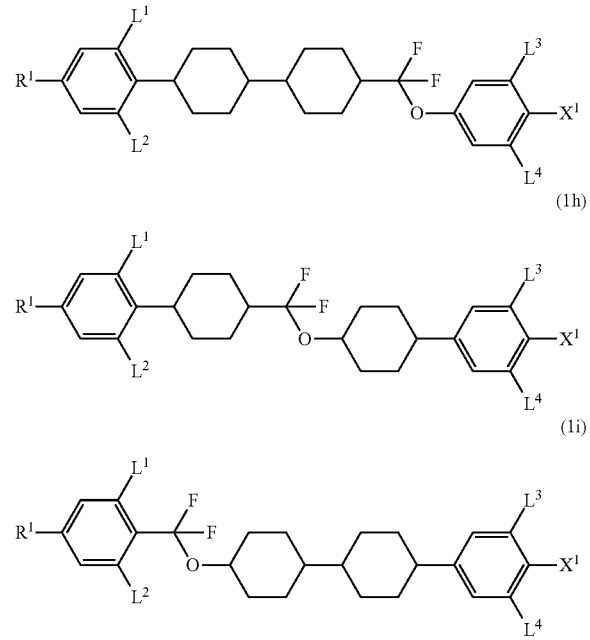

(1g)

(1h)

(1i)

wherein, in formulas (1g), (1h) and (1i), $R^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

$X^1$ is —$CF_3$ or —$OCF_3$;

$L^1$, $L^2$, $L^3$ and $L^4$ are independently hydrogen or fluorine; and in formulas (1h) and (1i), $X^1$ may be fluorine.

Item 9. The compound according to item 8, represented by formula (1g):

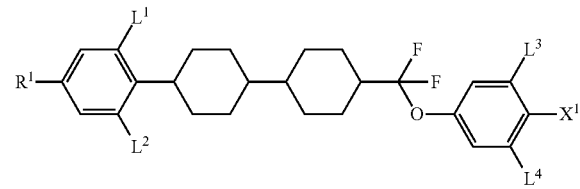

(1g)

wherein, in formula (1g), $R^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

$X^1$ is —$CF_3$ or —$OCF_3$; and $L^1$, $L^2$, $L^3$ and $L^4$ are independently hydrogen or fluorine.

Item 10. The compound according to item 8, represented by formula (1h) or (1i):

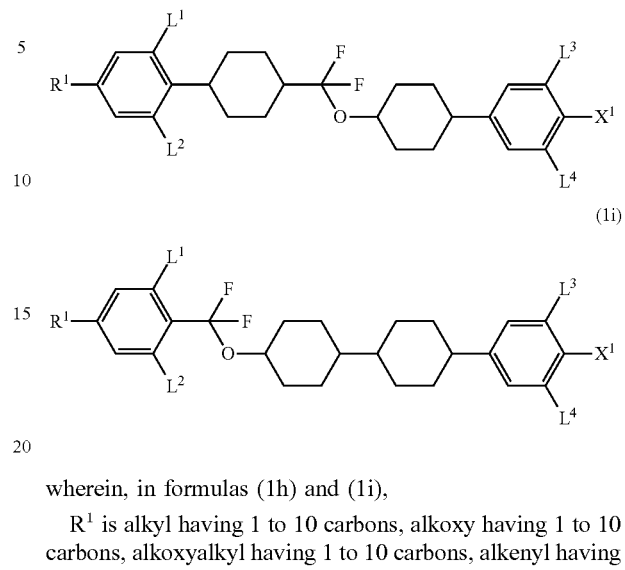

(1h)

(1i)

wherein, in formulas (1h) and (1i), $R^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons;

$X^1$ is fluorine, —$CF_3$ or —$OCF_3$; and $L^1$, $L^2$, $L^3$ and $L^4$ are independently hydrogen or fluorine.

Item 11. A liquid crystal composition, containing at least one compound according to any one of items 1 to 10.

Item 12. The liquid crystal composition according to item 11, further containing at least one compound selected from the group of compounds represented by formulas (2) to (4):

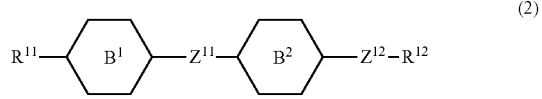

(2)

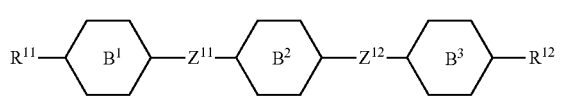

(3)

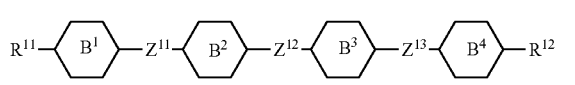

(4)

wherein, in formulas (2) to (4), $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

rings $B^1$, $B^2$, $B^3$ and $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 13. The liquid crystal composition according to item 11 or 12, further containing at least one compound selected from the group of compounds represented by formulas (5) to (7):

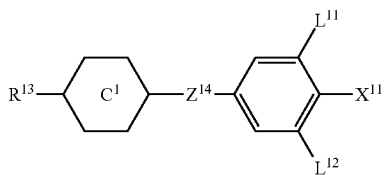
(5)

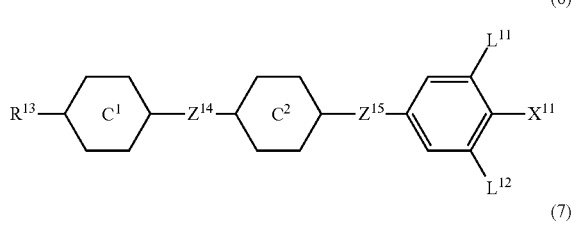
(6)

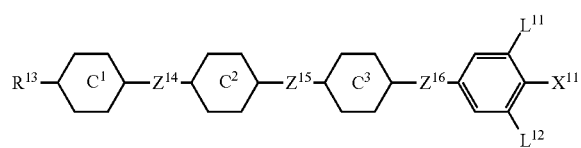
(7)

wherein, in formulas (5) to (7), $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

rings $C^1$, $C^2$ and $C^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine;

in which, when ring $C^3$ is 1,4-cyclohexylene, ring $C^1$ is 1,4-cyclohexylene, tetrahydropyran-2,5-diyl, 1,3-dioxane-2,5-diyl or pyrimidine-2,5-diyl.

Item 14. The liquid crystal composition according to any one of items 11 to 13, further containing at least one compound selected from the group of compounds represented by formula (8):

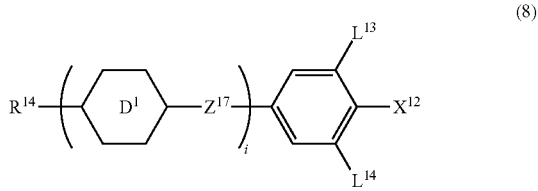
(8)

wherein, in formula (8), $R^{14}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{12}$ is —C≡N or —C≡C—C≡N;

ring $D^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl, and when a plurality of rings $D^1$ exist, rings $D^1$ may be identical or different;

$Z^{17}$ is a single bond, —$CH_2CH_2$—, —C≡C—, —COO—, —$CF_2O$—, —$OCF_2$— or —$CH_2O$—, and when a plurality of pieces $Z^{17}$ exist, $Z^{17}$ may be identical or different;

$L^{13}$ and $L^{14}$ are independently hydrogen or fluorine; and i is 1, 2, 3 or 4.

Item 15. The liquid crystal composition according to any one of items 11 to 14, further containing at least one compound selected from the group of compounds represented by formulas (9) to (15):

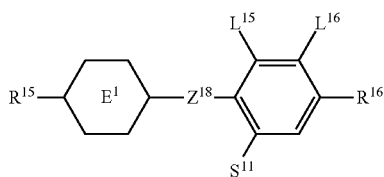
(9)

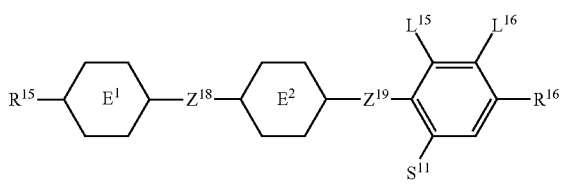
(10)

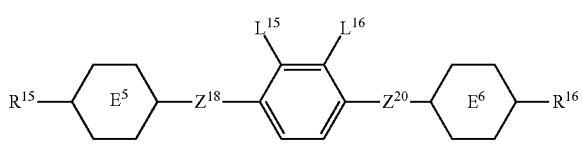
(11)

-continued

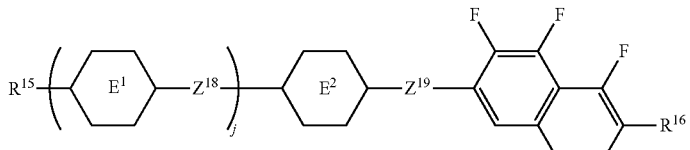

(12)

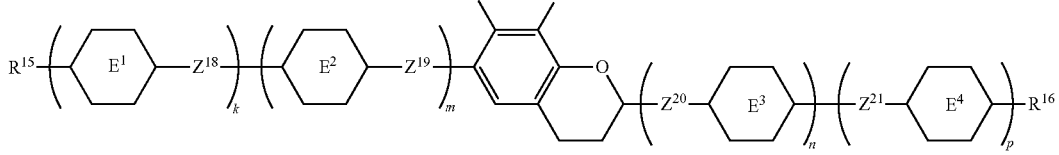

(13)

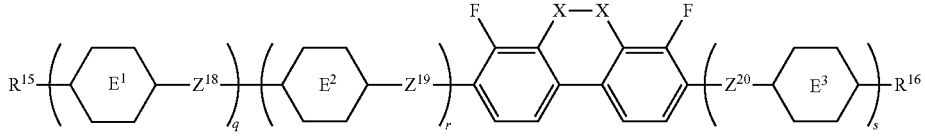

(14)

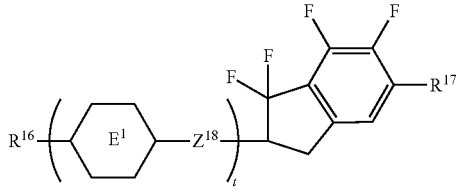

(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$R^{17}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

rings $E^1$, $E^2$, $E^3$ and $E^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl, and when a plurality of rings $E^1$, $E^2$, $E^3$ and $E^4$ exist, rings E, $E^2$, $E^3$ and $E^4$ may be identical or different;

rings $E^5$ and $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—, and when a plurality of $Z^{18}$, $Z^{19}$, $Z^{20}$ and $Z^{21}$ exist, $Z^{18}$, $Z^{19}$, $Z^{20}$ and $Z^{21}$ may be identical or different;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 16. The liquid crystal composition according to any one of items 11 to 15, further containing at least one additive selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent.

Item 17. A liquid crystal display device including the liquid crystal composition according to any one of items 11 to 16.

The invention further includes the following items: (a) the composition, further containing one or more additives selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent; (b) the liquid crystal composition, wherein a maximum temperature of a nematic phase is 70° C. or more, an optical anisotropy (measured at 25° C.) at a wavelength of 589 nanometers is 0.07 or more, and a dielectric anisotropy (measured at 25° C.) at a frequency of 1 kHz is 2 or more; and (c) the liquid crystal display device, wherein an operating mode in the liquid crystal display device includes a TN mode, an ECB mode, an OCB mode, an IPS mode or an FPA mode, and a driving mode in the liquid crystal display device includes an active matrix (AM) mode.

An aspect of compound (1), a synthesis method of compound (1), the liquid crystal composition and the liquid crystal display device will be described in the order.

1. Aspect of Compound (1)

Compound (1) of the invention has a feature of having four six-membered rings, and the six-membered rings are in the order of a benzene ring, a cyclohexane ring, a cyclohexane ring and a benzene ring. Compound (1) has a higher maximum temperature in comparison with a similar compound. Preferred examples of compound (1) will be described. Preferred examples of terminal groups $R^1$ and $X^1$, bonding groups $Z^1$, $Z^2$ and $Z^3$ and substituents $L^1$, $L^2$, $L^3$ and $L^4$ in compound (1) are also applied to a subordinate formula of formula (1) for compound (1). In compound (1), physical properties can be arbitrarily adjusted by suitably combining the groups. Compound (1) may contain an isotope such as $^2H$ (deuterium) and $^{13}C$ in an amount larger than an amount of natural abundance because no significant difference is caused in the physical properties of the compound. In addition, symbols in compound (1) are defined according to item 1.

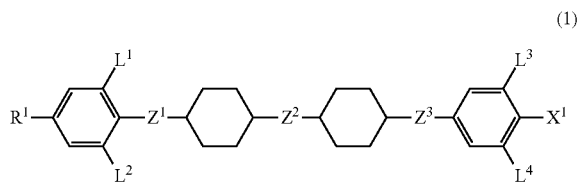
(1)

In formula (1), $R^1$ is alkyl having 1 to 10 carbons, alkoxy having 1 to 10 carbons, alkoxyalkyl having 1 to 10 carbons, alkenyl having 2 to 10 carbons or alkenyloxy having 2 to 10 carbons.

Preferred $R^1$ is alkyl having 3 to 10 carbons, alkoxy having 1 to 10 carbons, alkoxyalkyl having 1 to 10 carbons or alkenyl having 2 to 10 carbons. Further preferred $R^1$ is alkyl having 3 to 10 carbons or alkenyl having 2 to 10 carbons. Particularly preferred $R^1$ is alkenyl having 2 to 10 carbons.

Preferred alkyl is —$C_3H_7$, —$C_4H_9$, —$C_5H_{11}$, —$C_6H_{13}$ or —$C_7H_{15}$. Preferred alkoxy is —$OCH_3$, —$OC_2H_5$, —$OC_3H_7$, —$OC_4H_9$, —$OC_5H_{11}$, —$OC_6H_{13}$ or —$OC_7H_{15}$. Preferred alkoxyalkyl is —$CH_2OCH_3$, —$CH_2OC_2H_5$, —$(CH_2)_2OCH_3$, —$CH_2OC_3H_7$, —$(CH_2)_{20}C_2H_5$, —$(CH_2)_3OCH_3$, —$CH_2OC_4H_9$, —$(CH_2)_{20}C_3H_7$, —$(CH_2)_{30}C_2H_5$ or —$(CH_2)_4OCH_3$.

Preferred alkenyl is —CH=$CH_2$, —CH=$CHCH_3$, —$CH_2$CH=$CH_2$, —CH=$CHC_2H_5$, —$CH_2$CH=$CHCH_3$, —$(CH_2)_2$, —CH=$CH_2$, —CH=$CHC_3H_7$, —$CH_2$CH=$CHC_2H_5$, —$(CH_2)_2$, —CH=$CHCH_3$ or —$(CH_2)_3$, —CH=$CH_2$. Preferred alkenyloxy is —$OCH_2$CH=$CH_2$, —$OCH_2$CH=$CH_2$, —$OCH_2$CH=$CHCH_3$ or —$OCH_2$CH=$CHC_2H_5$.

Preferred $R^1$ is —$C_3H_7$, —$C_4H_9$, —$C_5H_{11}$, —$C_6H_{13}$, —$OCH_3$, —$OC_2H_5$, —$OC_3H_7$, —$OC_4H_9$, —$OC_5H_{11}$, —$CH_2OCH_3$, —$CH_2OC_2H_5$, —$(CH_2)_2OCH_3$, —CH=$CH_2$, —CH=$CHCH_3$, —$(CH_2)_2$, —CH=$CH_2$, —$CH_2$CH=$CHC_2H_5$, —$(CH_2)_2$, —CH=$CHCH_3$, —$OCH_2$CH=$CH_2$, —$OCH_2$CH=$CHCH_3$ or —$OCH_2$CH=$CHC_2H_5$. Further preferred $R^1$ is —$C_3H_7$, —$C_4H_9$, —$C_5H_{11}$, —$C_6H_{13}$, —$(CH_2)_2$—CH=$CH_2$ or —$(CH_2)_2$—CH=$CHCH_3$.

When $R^1$ has the straight chain, a temperature range of the liquid crystal phase is wide and the viscosity is small. When $R^1$ has the branched chain, compatibility with other liquid crystal compounds is good. A compound in which $R^1$ is optically active is useful as a chiral dopant. A reverse twisted domain to be generated in the liquid crystal display device can be prevented by adding the compound to the composition. A compound in which $R^1$ is not optically active is useful as a component of the composition. When $R^1$ is alkenyl, a preferred configuration depends on a position of a double bond. An alkenyl compound having the preferred configuration has the small viscosity, the high maximum temperature or the wide temperature range of the liquid crystal phase.

A preferred configuration of —CH=CH— in the alkenyl depends on a position of a double bond. A trans configuration is preferred in alkenyl having the double bond in an odd-numbered position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$. A cis configuration is preferred in alkenyl having the double bond in an even-numbered position, such as —$CH_2$CH=$CHCH_3$, —$CH_2$CH=$CHC_2H_5$ and —$CH_2$CH=$CHC_3H_7$. The alkenyl compound having a preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

In formula (1), $Z^1$, $Z^2$ and $Z^3$ are independently a single bond, —COO—, —$OCH_2$—, —$CF_2O$—, —$CH_2CH_2$—, —$CF_2CF_2$—, —CF=CF—, —C≡C—, —$(CH_2)_4$— or —$CH_2$CH=$CHCH_2$—, $Z^1$ and $Z^3$ may be independently —CH=CH—, and at least one of $Z^1$, $Z^2$ and $Z^3$ is —$CF_2O$—.

Preferred $Z^1$ or $Z^3$ is a single bond, —COO—, —$OCH_2$—, —$CF_2O$—, —$CH_2CH_2$— or —CH=CH— and preferred $Z^2$ is a single bond, —COO—, —$OCH_2$—, —$CF_2O$— or —$CH_2CH_2$—. Further preferred $Z^1$ or $Z^3$ is a single bond, —COO—, —$OCH_2$—, —$CF_2O$— or —CH=CH—, and further preferred $Z^2$ is a single bond, —COO—, —$OCH_2$— or —$CF_2O$—. Particularly preferred $Z^1$, $Z^2$ or $Z^3$ is a single bond or —$CF_2O$—. Most preferred $Z^1$, $Z^2$ or $Z^3$ is a single bond.

When $Z^1$, $Z^2$ or $Z^3$ is a single bond, compound (1) has a high chemical stability and a small viscosity. When two of $Z^1$, $Z^2$ and $Z^3$ are —$CF_2O$—, compound (1) has a small viscosity, a large dielectric anisotropy and a high maximum temperature.

In formula (1), $X^1$ is fluorine, —$CF_3$ or —$OCF_3$. Further preferred $X^1$ is fluorine or —$OCF_3$. Particularly preferred $X^1$ is fluorine. Particularly preferred $X^1$ is also —$OCF_3$. When $X^1$ is fluorine, compound (1) has a small viscosity. When $X^1$ is —$CF_3$, compound (1) has a large dielectric anisotropy. When $X^1$ is —$OCF_3$, compound (1) has an excellent compatibility with other liquid crystal compounds.

In formula (1), $L^1$, $L^2$, $L^3$ and $L^4$ are independently hydrogen, fluorine or chlorine. At least one of L to $L^4$ is preferably fluorine. At least two of L to $L^4$ are further preferably fluorine. At least one of $L^1$ and $L^2$ is preferably fluorine from a viewpoint of a large dielectric anisotropy. $L^1$ and $L^2$ are further preferably fluorine from a viewpoint of the large dielectric anisotropy.

In formula (1), when $R^1$ is alkyl, $Z^1$ and $Z^2$ are a single bond, and $Z^3$ is —$CF_2O$—, $R^1$ is alkyl having 3 to 10 carbons.

Preferred compound (1) is as described in items 2 to 9. In the compound according to item 2, compound (1a) is preferred from a viewpoint of a balance of physical properties. Compound (1b) is preferred from a viewpoint of a small viscosity. Compound (1c) is preferred from a viewpoint of a high maximum temperature.

2. Synthesis of Compound (1)

The synthesis method of compound (1) will be described. Compound (1) can be prepared by suitably combining methods in synthetic organic chemistry. A methods for introducing an objective terminal group, ring and bonding group into a starting material is described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Group Z

First, a scheme is shown with regard to a method for forming bonding groups $Z^1$ to $Z^3$. Next, reactions described in the scheme in methods (1) to (11) are described. In the scheme, $MSG^1$ (or $MSG^2$) is a monovalent organic group having at least one ring. The monovalent organic groups represented by a plurality of $MSG^1$ (or $MSG^2$) used in the scheme may be identical or different. Compounds (1A) to (1J) correspond to compound (1).

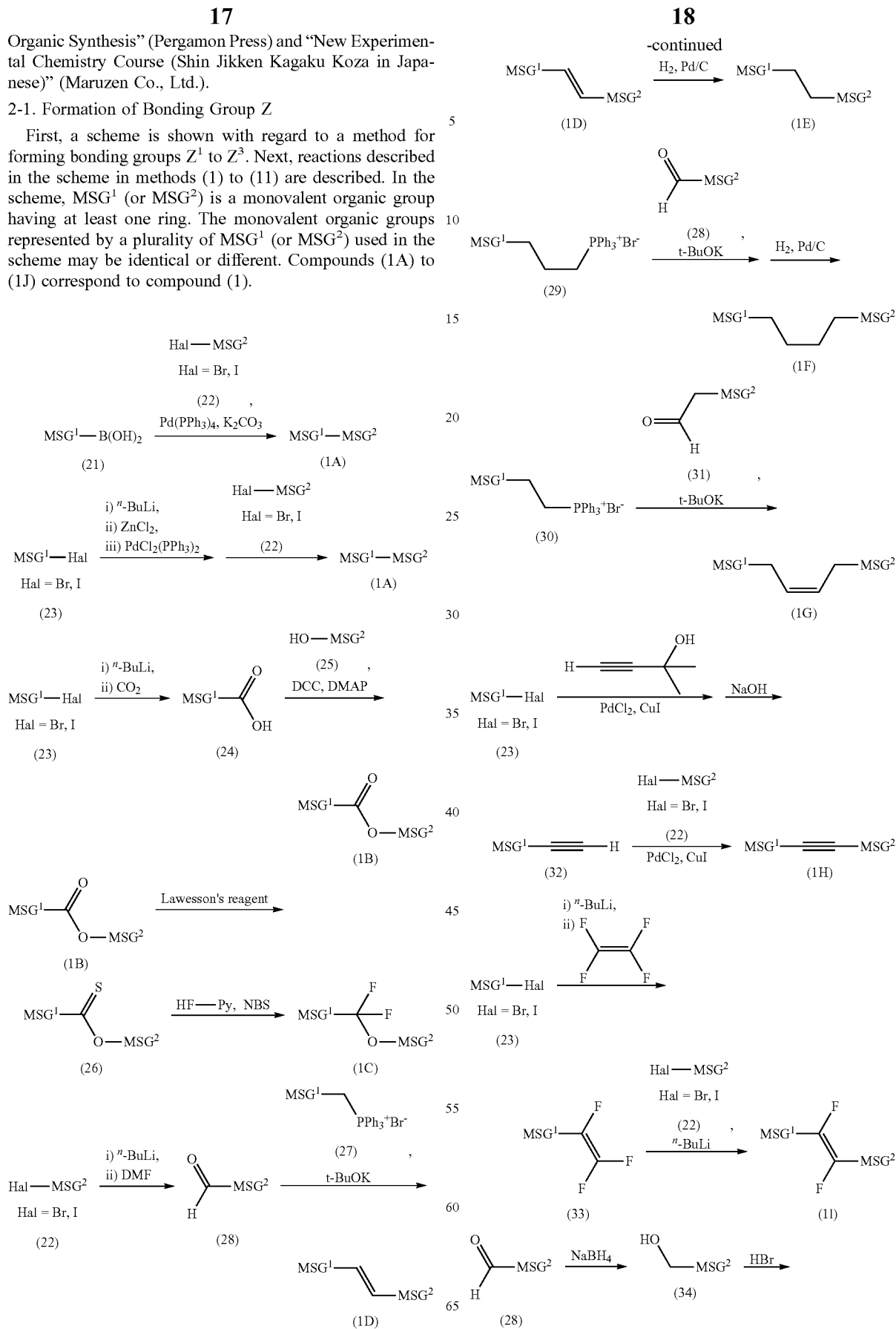

-continued

MSG¹—OH

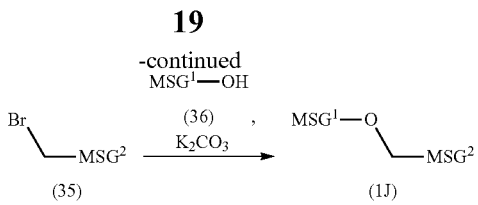

(1) Formation of a Single Bond

Compound (1A) is prepared by allowing aryl boronic acid (21) prepared according to a known method to react with halide (22), in the presence of carbonate and a catalyst such as tetrakis(triphenylphosphine)palladium. Compound (1A) is also prepared by allowing halide (23) prepared according to a known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydration of compound (25) prepared according to a known method and carboxylic acid (24) in the presence of 1,3-dicyclohexylcarbodiimide (DCC) and 4-dimethylaminopyridine (DMAP).

(3) Formation of —CF$_2$O—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with (diethylamino) sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH=CH—

Aldehyde (28) is obtained by treating halide (22) with n-butyllithium and then allowing the treated halide to react with formamide such as N,N-dimethylformamide (DMF). Phosphorus ylide is generated by treating phosphonium salt (27) prepared according to a known method with a base such as potassium t-butoxide. Compound (1D) is prepared by allowing the phosphorus ylide to react with aldehyde (28). A cis isomer may be generated depending on reaction conditions, and the cis isomer is isomerized into a trans isomer according to a known method when necessary.

(5) Formation of —CH$_2$CH$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH=CH— is obtained by using phosphonium salt (29) in place of phosphonium salt (27) according to the method in method (4). Compound (1F) is prepared by performing catalytic hydrogenation of the compound obtained.

(7) Formation of —CH$_2$CH=CHCH$_2$—

Compound (1G) is prepared by using phosphonium salt (30) in place of phosphonium salt (27) and aldehyde (31) in place of aldehyde (28) according to the method of the method (4). A trans isomer may be generated depending on reaction conditions, and the trans isomer is isomerized to a cis isomer according to a known method when necessary.

(8) Formation of —C≡C—

Compound (32) is obtained by allowing halide (23) to react with 2-methyl-3-butyn-2-ol in the presence of a catalyst including dichloropalladium and copper halide, and then performing deprotection under basic conditions. Compound (1H) is prepared by allowing compound (32) to react with halide (22) in the presence of the catalyst including dichloropalladium and copper halide.

(9) Formation of —CF=CF—

Compound (33) is obtained by treating halide (23) with n-butyllithium and then allowing the treated halide to react with tetrafluoroethylene. Compound (1I) is prepared by treating halide (22) with n-butyllithium, and then allowing the treated halide to react with compound (33).

(10) Formation of —OCH$_2$—

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of —CF$_2$CF$_2$—

A compound having —(CF$_2$)$_2$— is obtained by fluorinating diketone (—COCO—) with sulfur tetrafluoride, in the presence of a hydrogen fluoride catalyst, according to the method described in J. Am. Chem. Soc., 2001, 123, 5414.

3. Liquid Crystal Composition 3-1. Component Compound

A liquid crystal composition of the invention is described. The composition contains at least one compound (1) as component A. The composition may contain two, three or more compounds (1). A component in the composition may be only compound (1). In order to develop excellent physical properties, the composition preferably contains at least one of compounds (1) in the range of approximately 1% by weight to approximately 99% by weight. In a composition having a positive dielectric anisotropy, a preferred content of compound (1) is in the range of approximately 5% by weight to approximately 60% by weight. In a composition having a negative dielectric anisotropy, a preferred content of compound (1) is approximately 30% by weight or less. The composition may contain compound (1) and liquid crystal compounds that are not described herein.

The composition contains compound (1) as component A, and preferably further contains a liquid crystal compound selected from components B, C, D and E described below. Component B includes compounds (2) to (4). Component C includes compounds (5) to (7) Component D includes compound (8). Component E includes compounds (9) to (15). The composition may contain any other liquid crystal compound different from compounds (2) to (15). The composition may not contain any other liquid crystal compound. When the composition is prepared, components B, C, D and E are preferably selected by taking into account a positive or negative dielectric anisotropy and magnitude of the dielectric anisotropy. A composition in which the components are suitably selected has a high stability to heat and light, a high maximum temperature, a low minimum temperature, a small viscosity, a suitable optical anisotropy (namely, a large optical anisotropy or a small optical anisotropy), a large dielectric anisotropy, a large specific resistance and a suitable elastic constant (namely, a large elastic constant or a small elastic constant).

Component B includes a compound in which two terminal groups are alkyl or the like. Preferred examples of component B include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine.
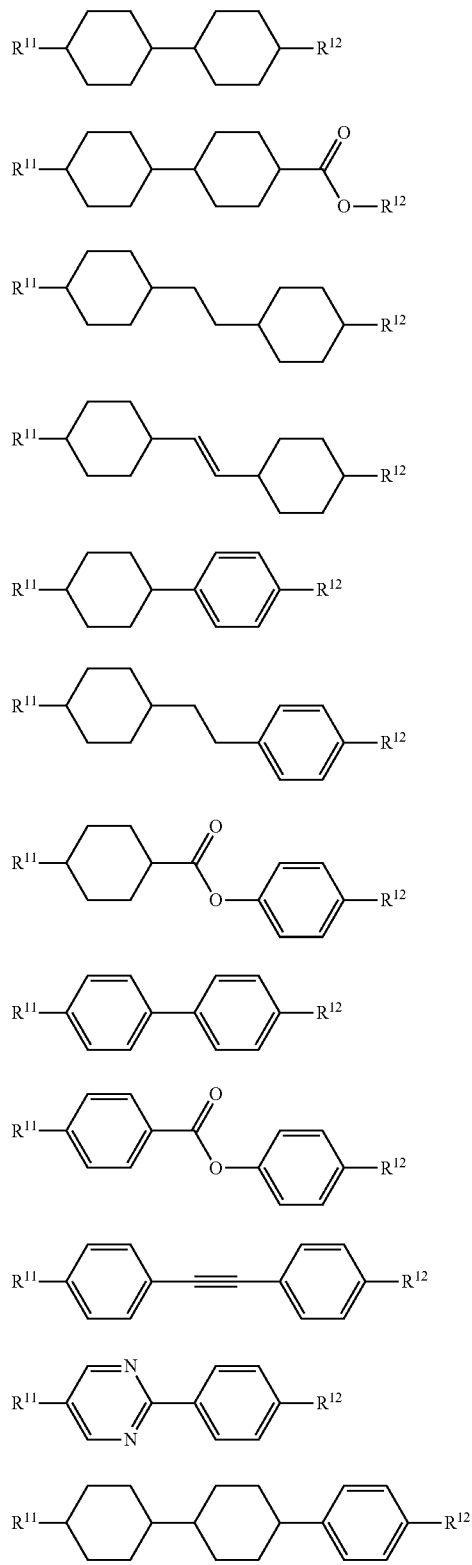
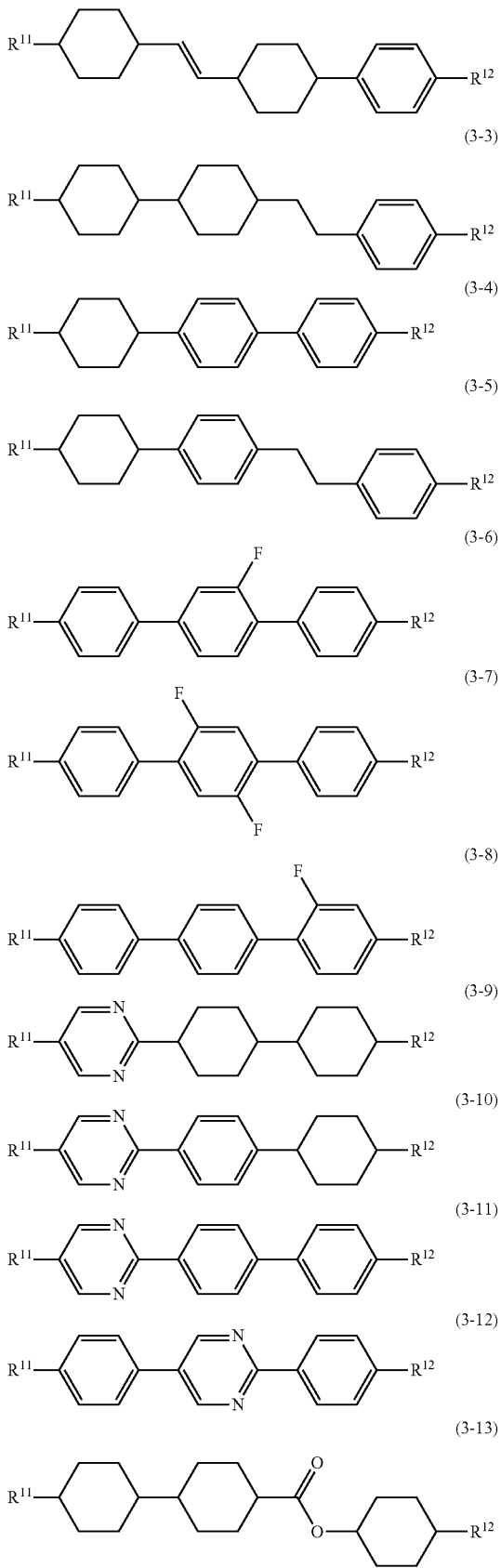

(3-14)
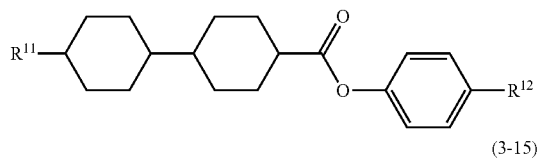

(3-15)
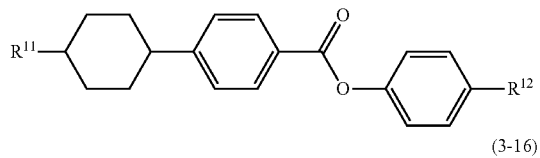

(3-16)
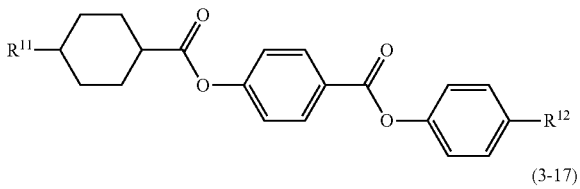

(3-17)
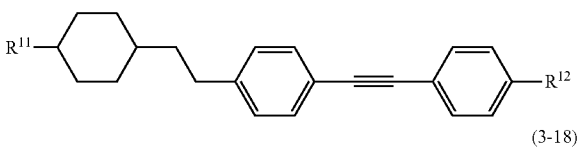

(3-18)
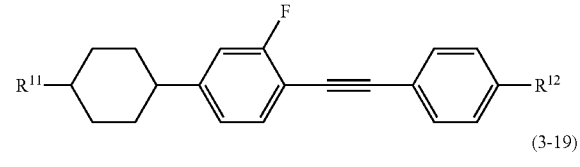

(3-19)
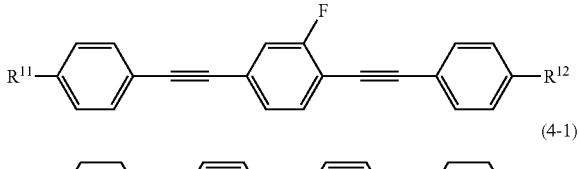

(4-1)
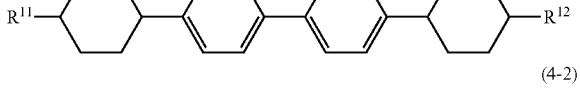

(4-2)
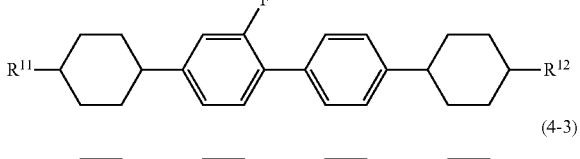

(4-3)
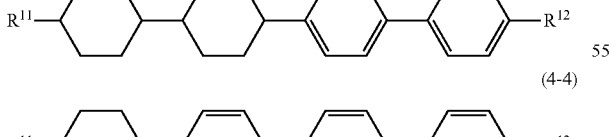

(4-4)

(4-5)
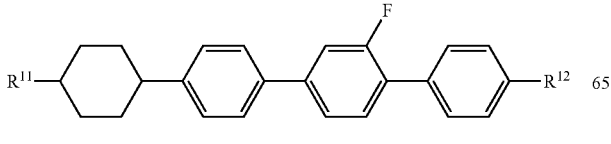

(4-6)
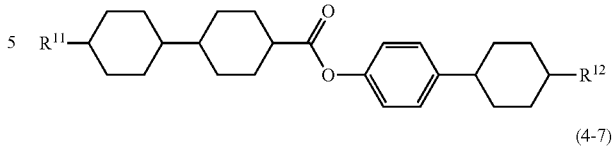

(4-7)
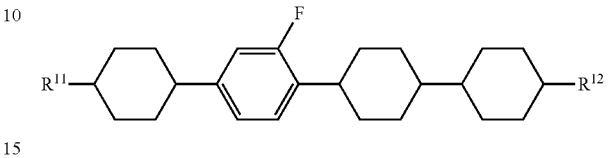

Component B has a small dielectric anisotropy. Component B is close to neutrality. Compound (2) is effective in decreasing viscosity or adjusting optical anisotropy. Compounds (3) and (4) are effective in extending the temperature range of the nematic phase by increasing the maximum temperature, or in adjusting the optical anisotropy.

As a content of component B is increased, the viscosity of the composition is decreased, and the dielectric anisotropy is decreased. Thus, as long as a desired value of threshold voltage of the device is met, the content is preferably as large as possible. When a composition for the IPS mode, the VA mode or the like is prepared, the content of component B is preferably approximately 30% by weight or more, and further preferably approximately 40% by weight or more, based on the weight of the liquid crystal composition.

Component C is a compound having a halogen-containing group or a fluorine-containing group at a right terminal. Preferred examples of component C include compounds (5-1) to (5-16), compounds (6-1) to (6-113) and compounds (7-1) to (7-57). In the compounds, $R^{13}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

(5-1)
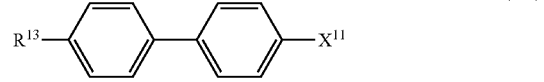

(5-2)
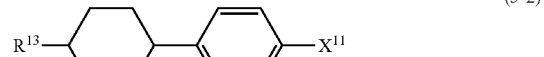

(5-3)
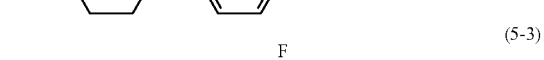

(5-4)
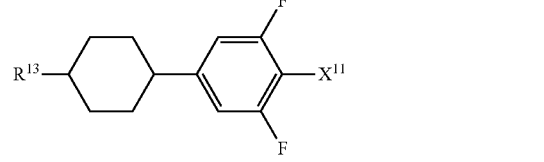

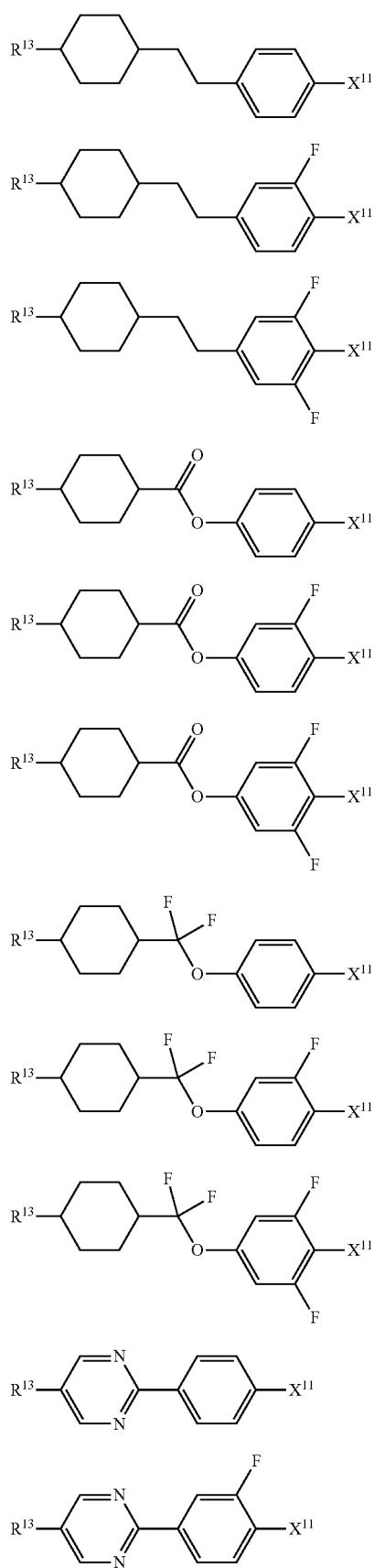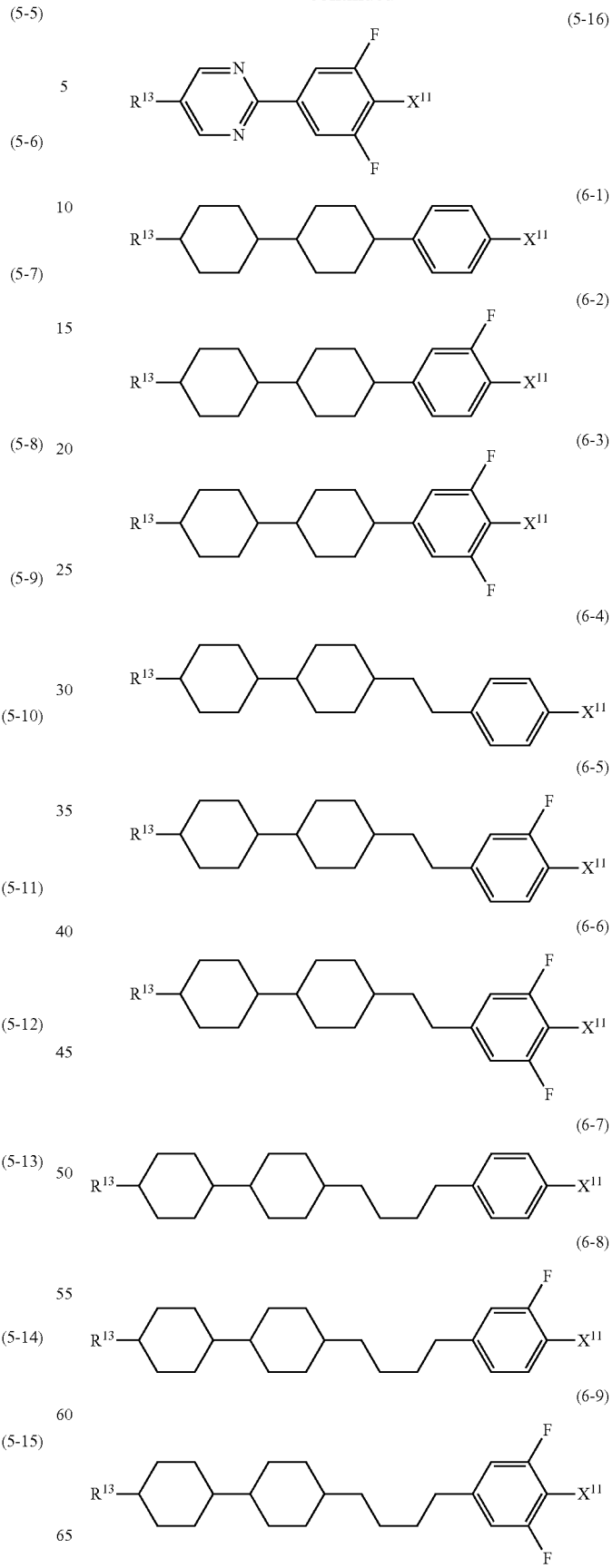

(6-10)
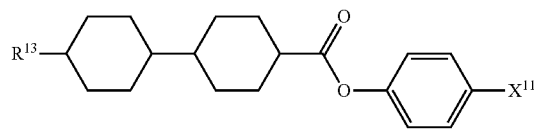
(6-11)
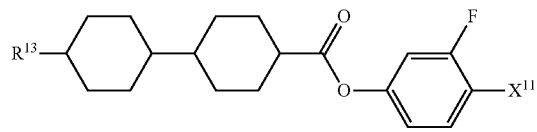
(6-12)
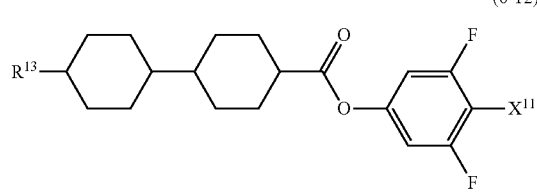
(6-13)
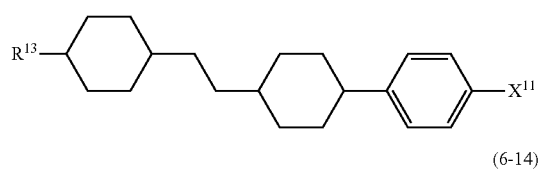
(6-14)
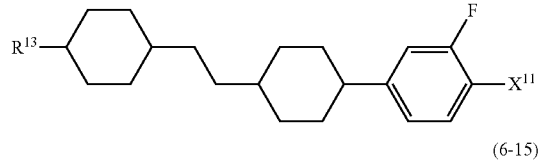
(6-15)
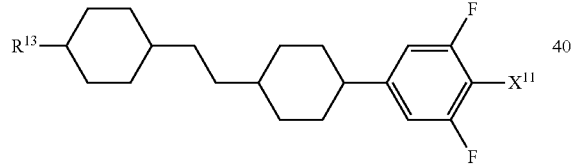
(6-16)
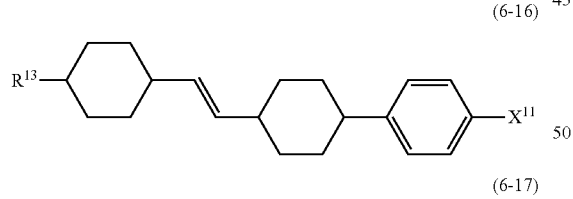
(6-17)
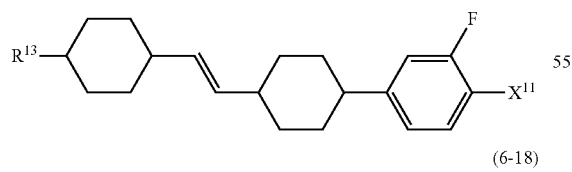
(6-18)
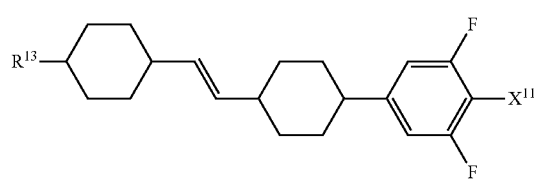
(6-19)
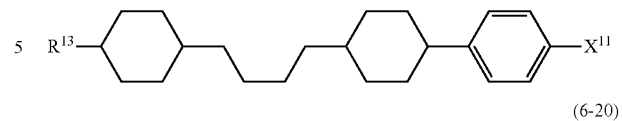
(6-20)
(6-21)
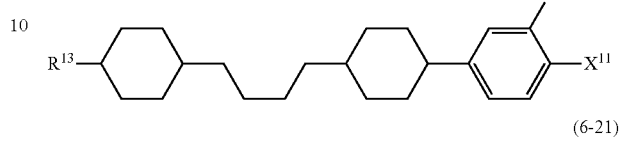
(6-22)
(6-23)
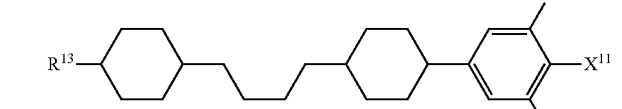
(6-24)
(6-25)
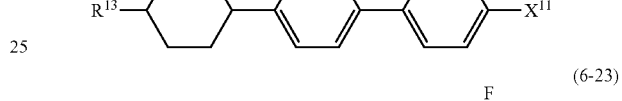
(6-26)
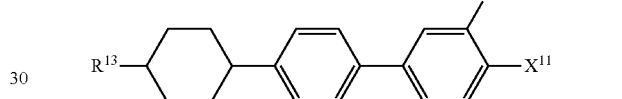
(6-27)
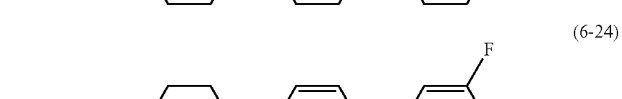
(6-28)

(6-29)
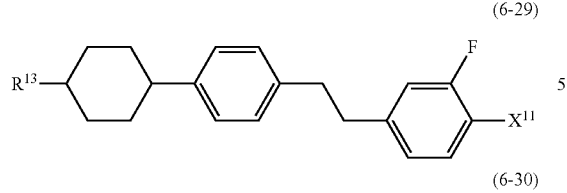
(6-30)
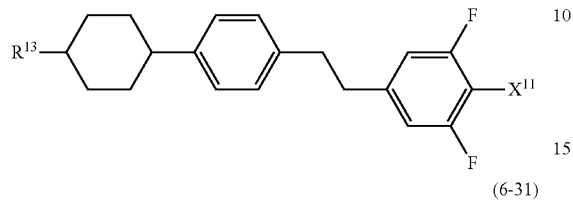
(6-31)
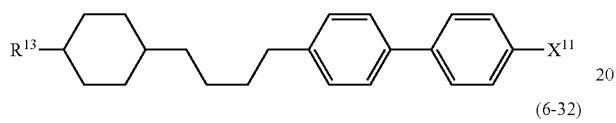
(6-32)
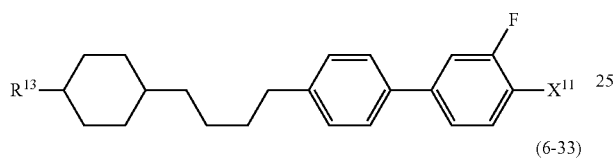
(6-33)
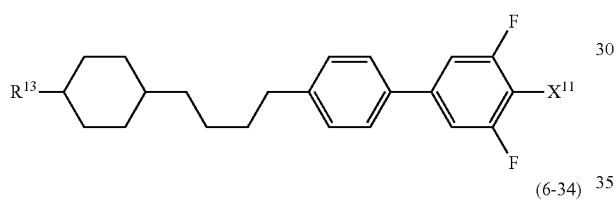
(6-34)
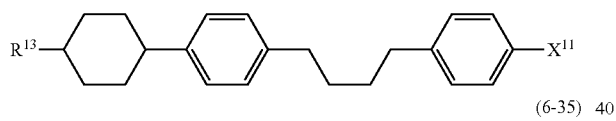
(6-35)
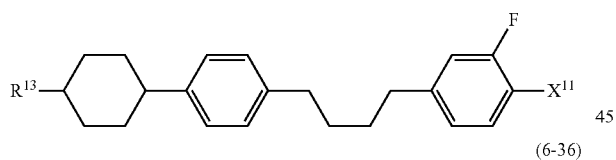
(6-36)
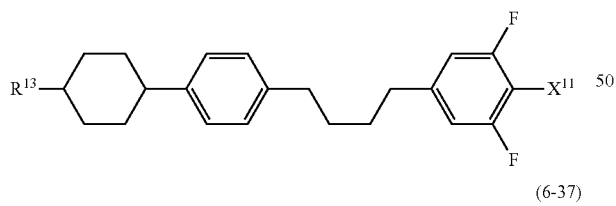
(6-37)
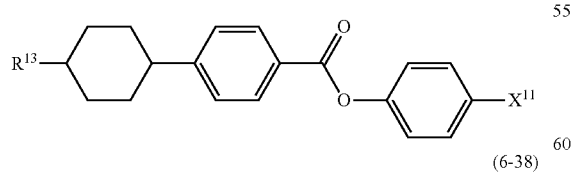
(6-38)
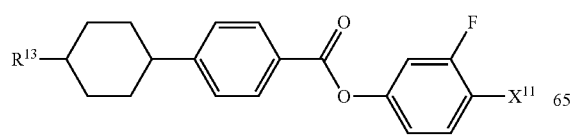
(6-39)
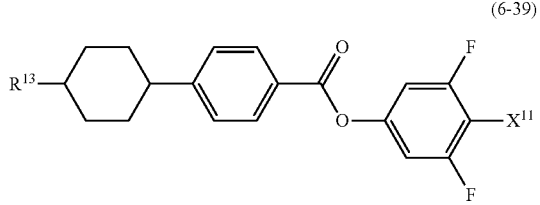
(6-40)
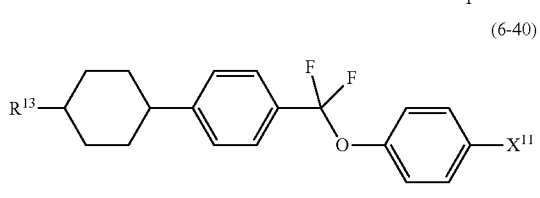
(6-41)
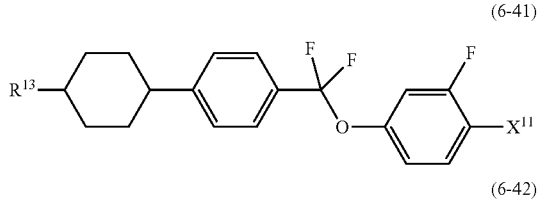
(6-42)
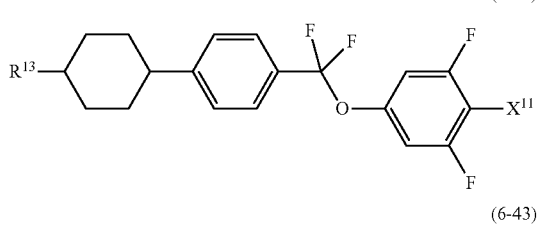
(6-43)
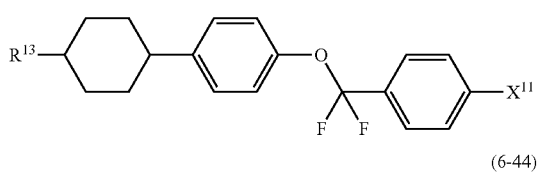
(6-44)
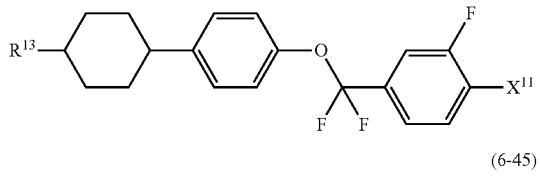
(6-45)
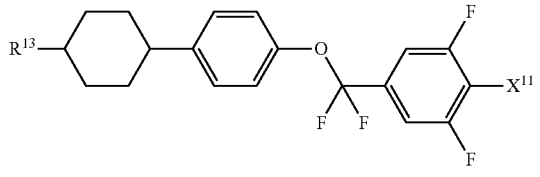
(6-46)
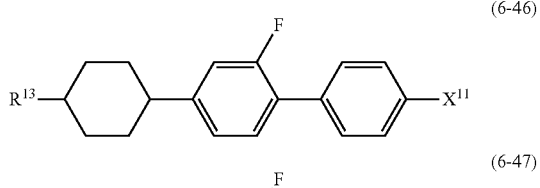
(6-47)

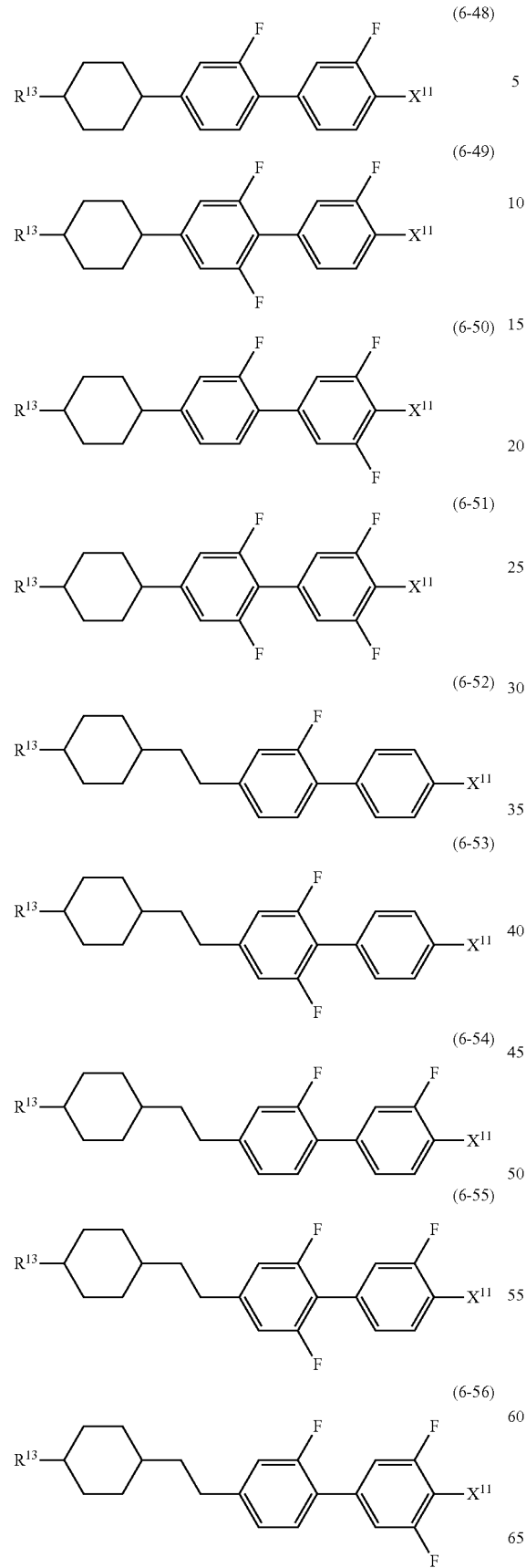
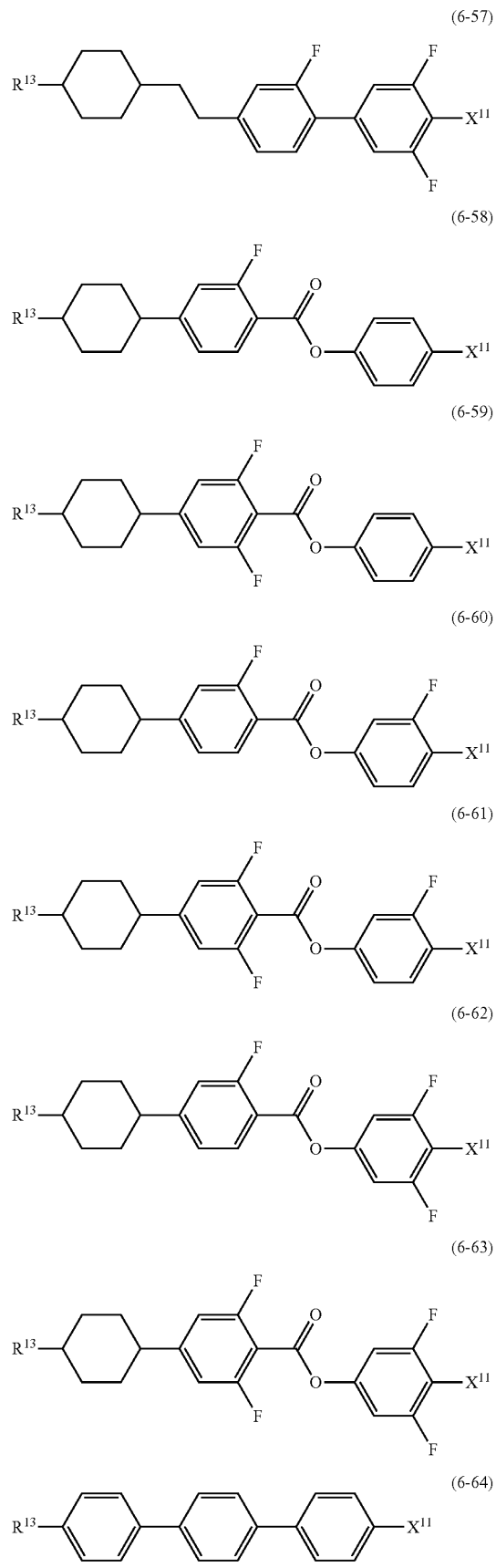

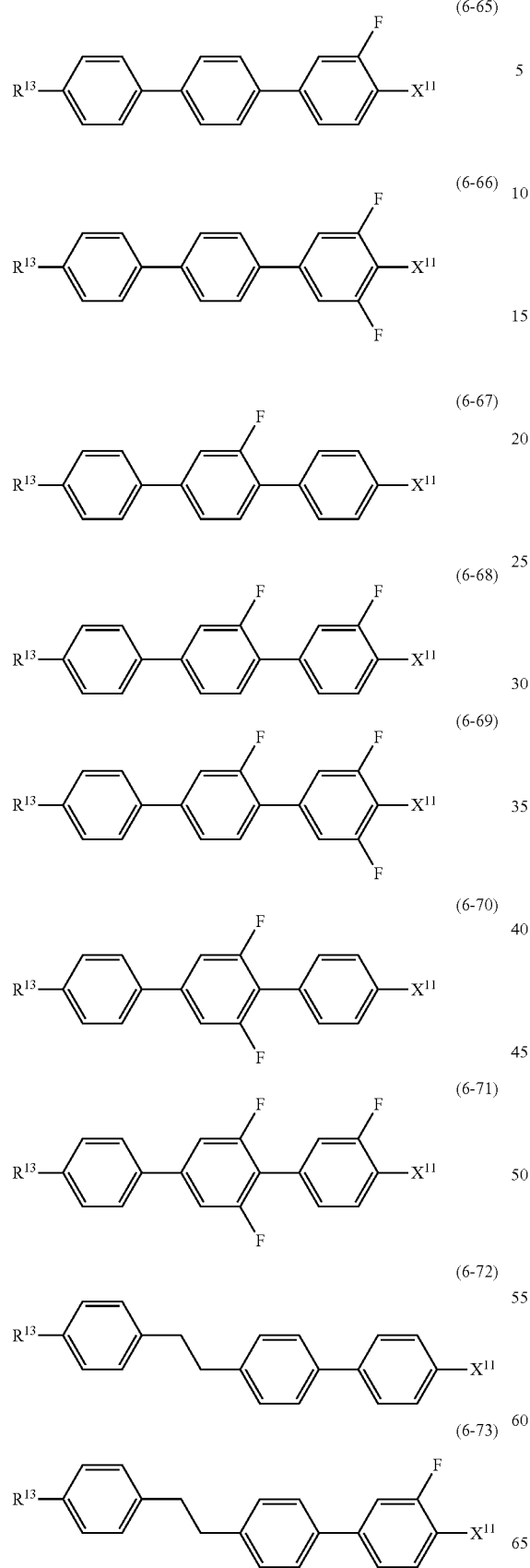
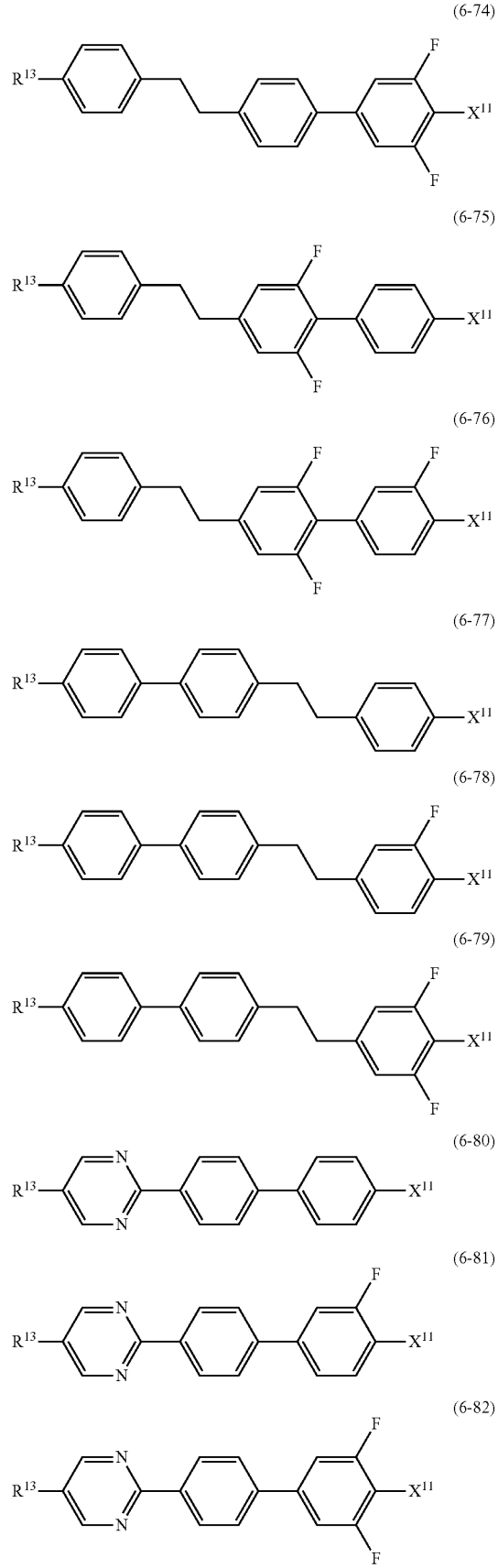

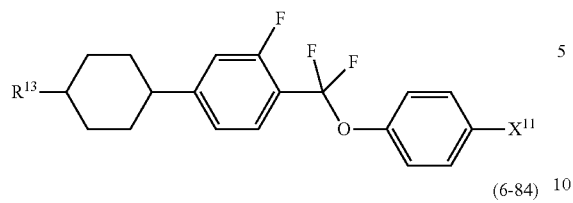 (6-83)
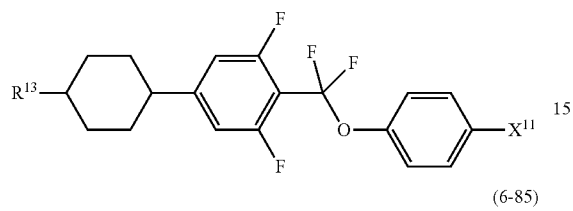 (6-84)
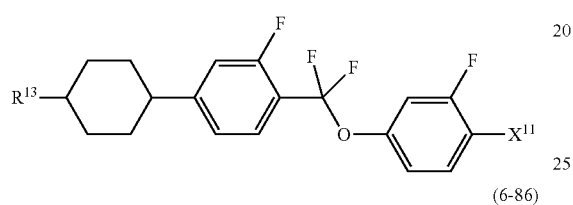 (6-85)
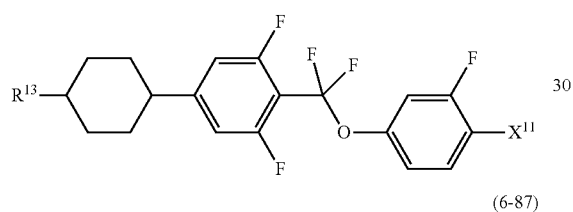 (6-86)
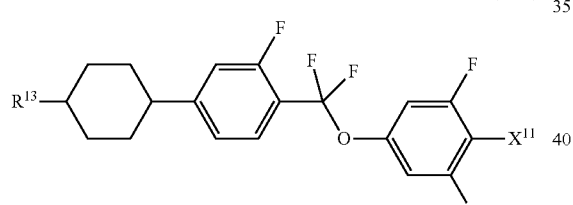 (6-87)
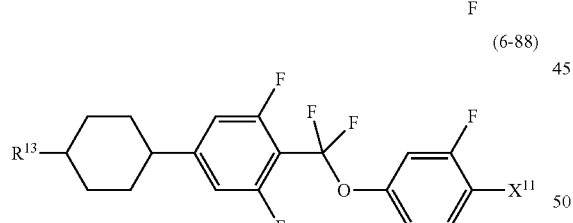 (6-88)
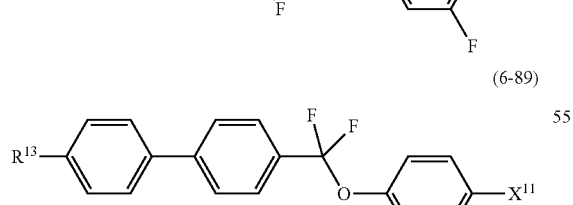 (6-89)
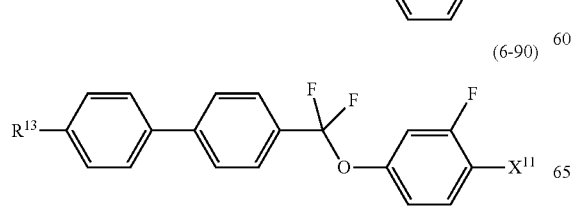 (6-90)
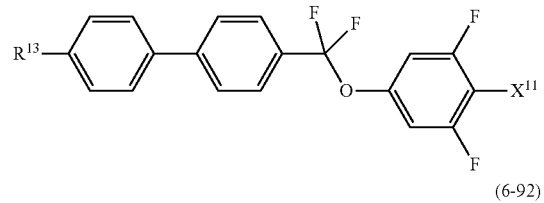 (6-91)
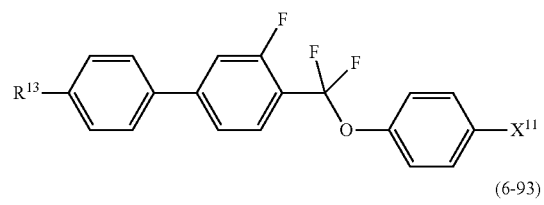 (6-92)
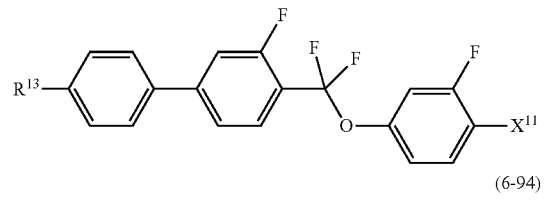 (6-93)
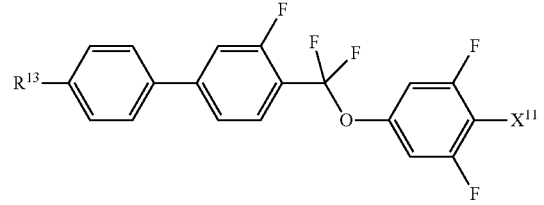 (6-94)
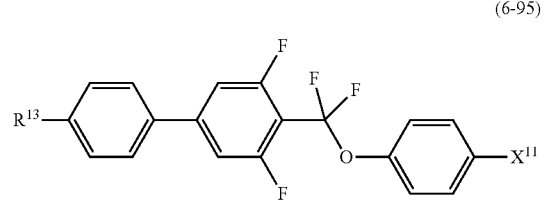 (6-95)
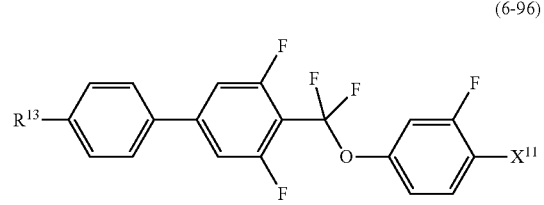 (6-96)
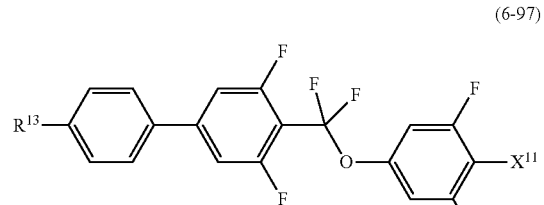 (6-97)
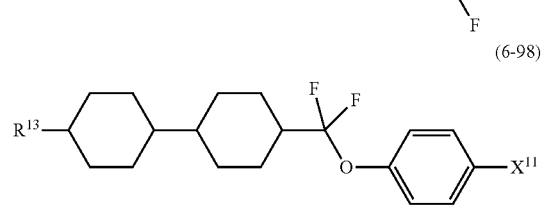 (6-98)

-continued
(6-99)
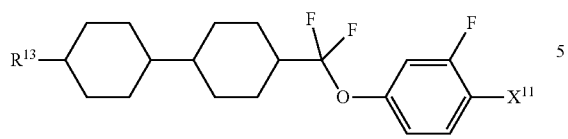
(6-100)
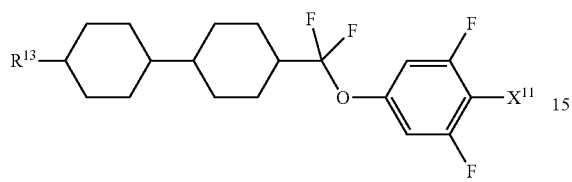
(6-101)
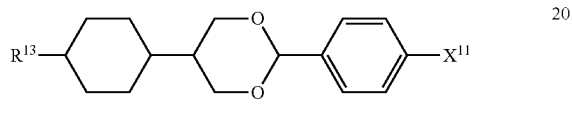
(6-102)
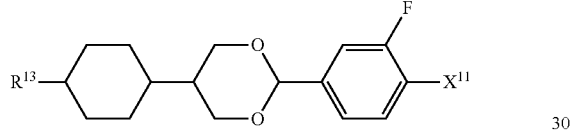
(6-103)
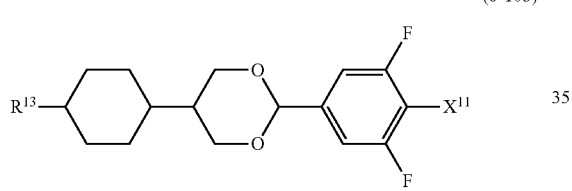
(6-104)
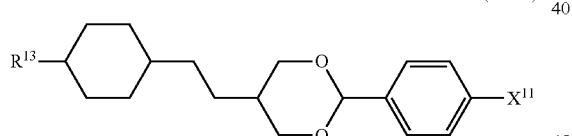
(6-105)
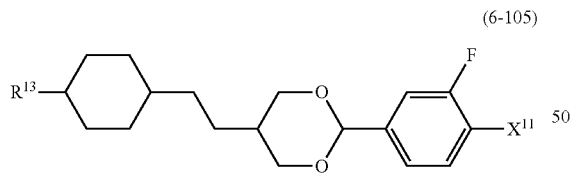
(6-106)
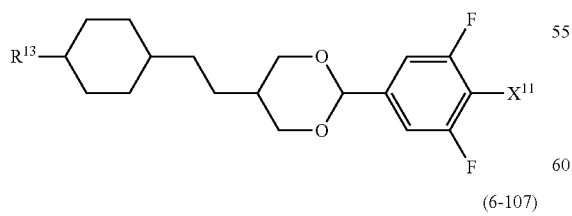
(6-107)
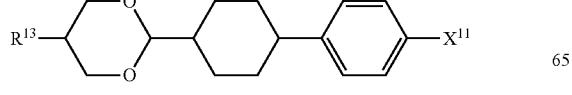
-continued
(6-108)
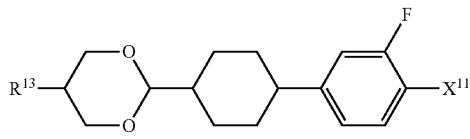
(6-109)
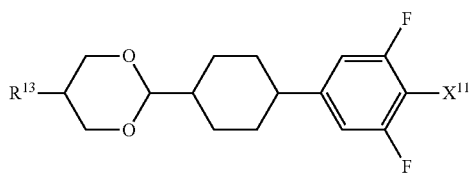
(6-110)
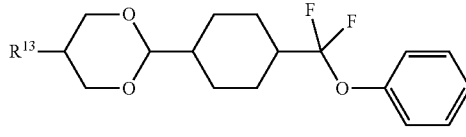
(6-111)
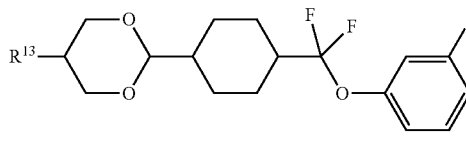
(6-112)
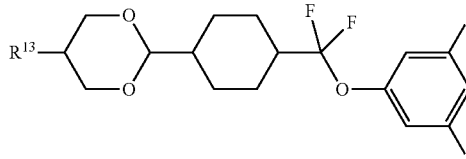
(6-113)
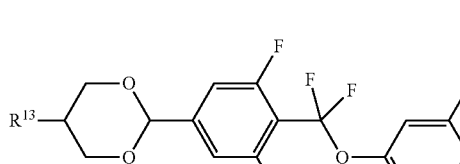
(7-1)
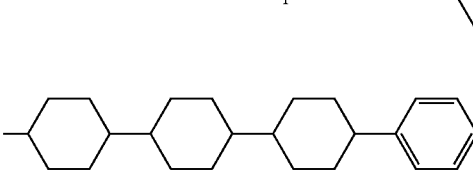
(7-2)
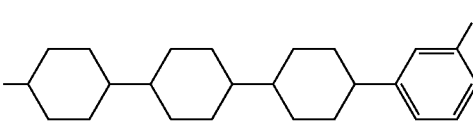
(7-3)
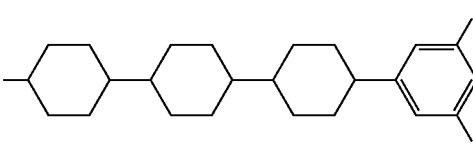

(7-4) 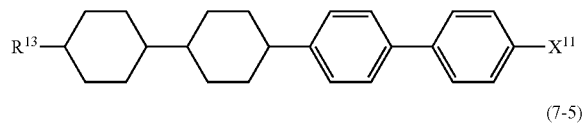
(7-5) 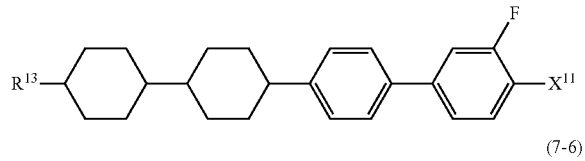
(7-6) 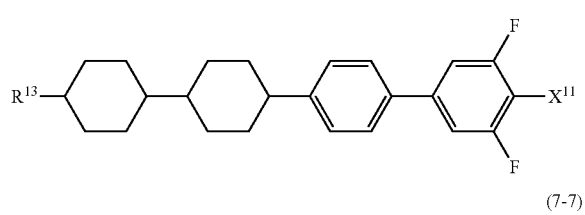
(7-7) 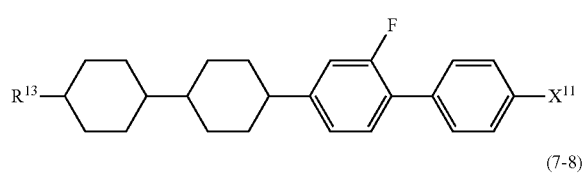
(7-8) 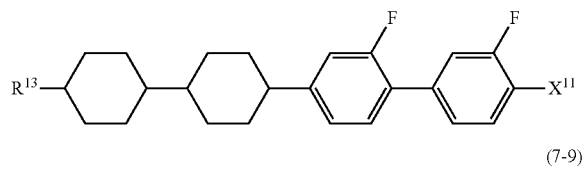
(7-9) 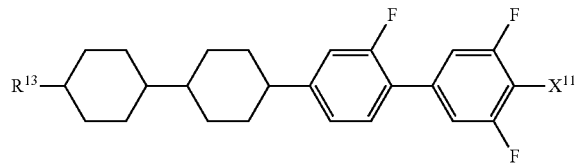
(7-10) 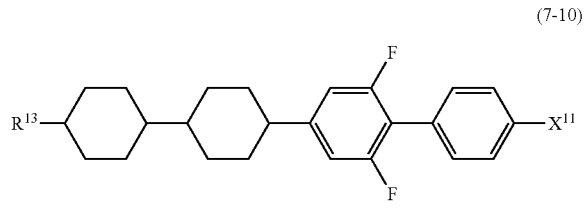
(7-11) 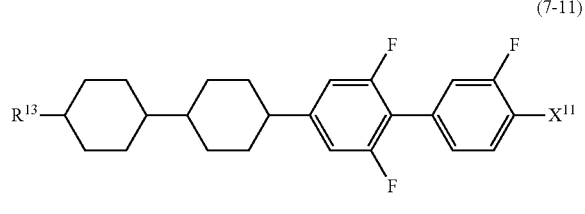
(7-12) 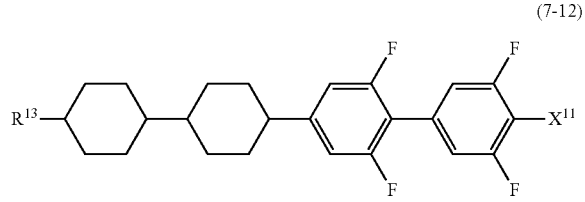
(7-13) 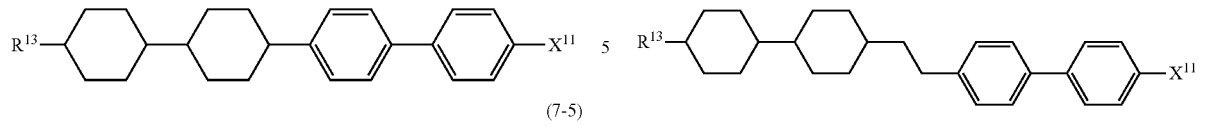
(7-14) 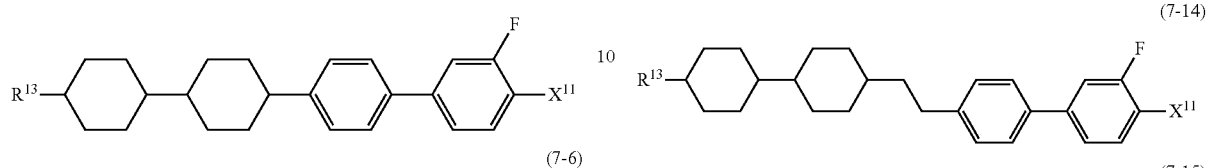
(7-15) 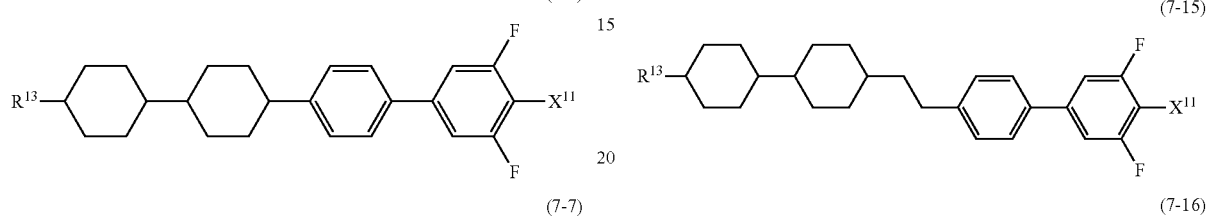
(7-16) 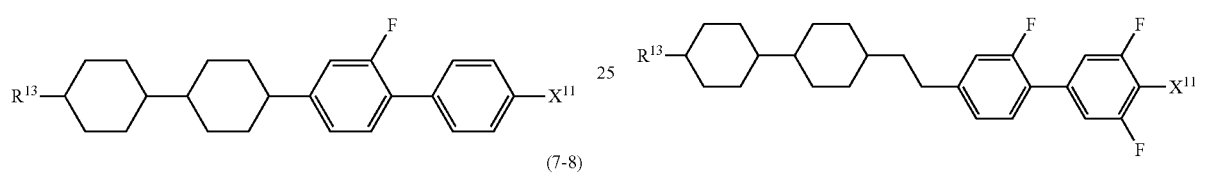
(7-17) 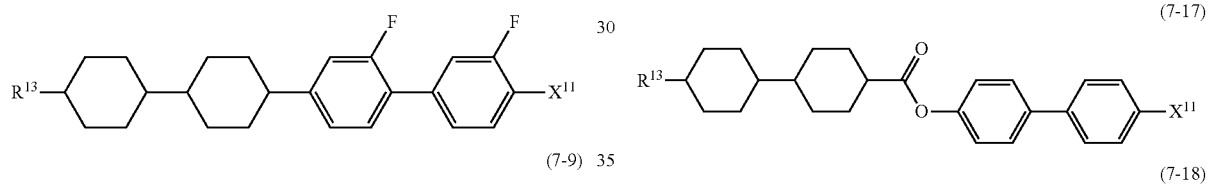
(7-18) 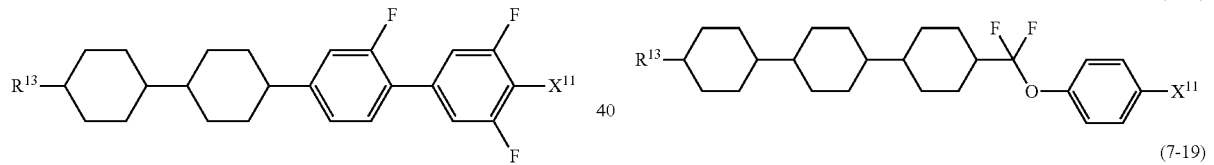
(7-19) 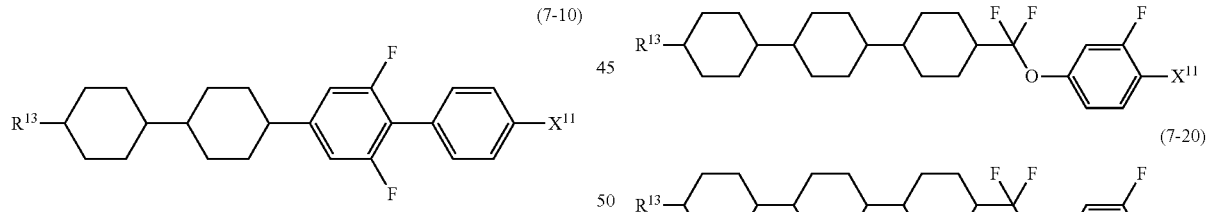
(7-20) 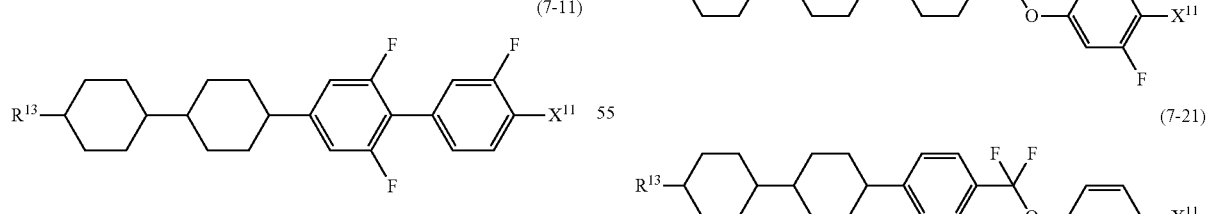
(7-21) 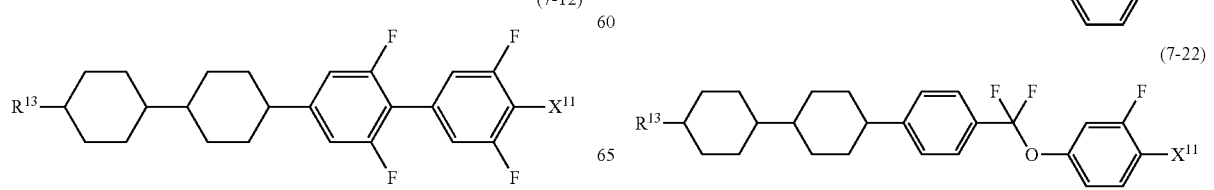
(7-22)

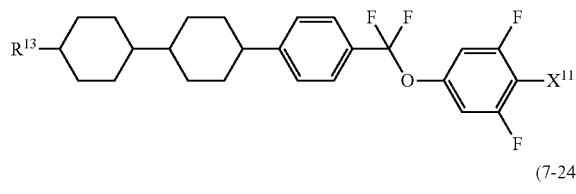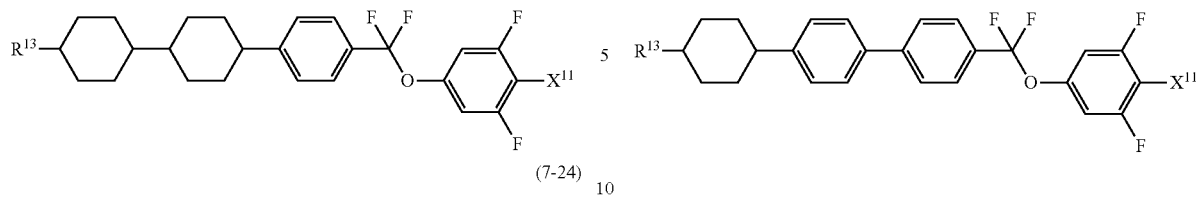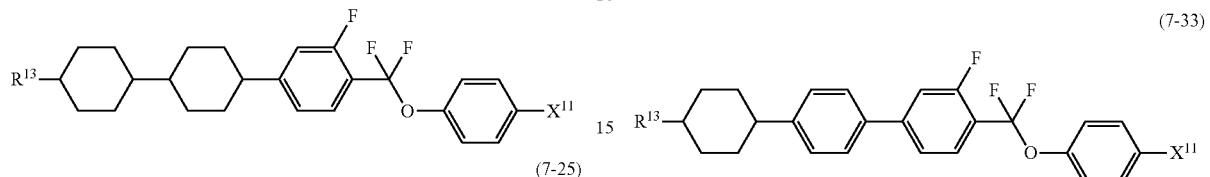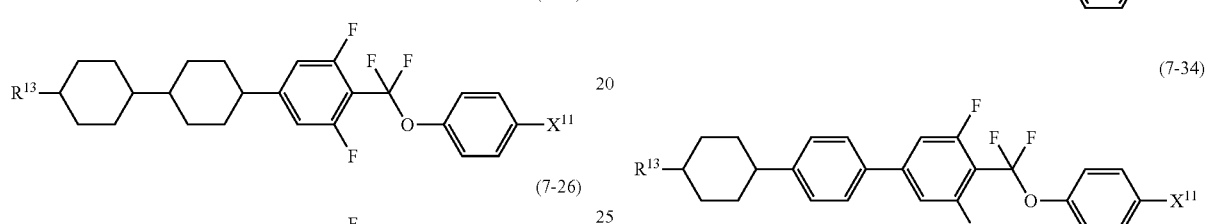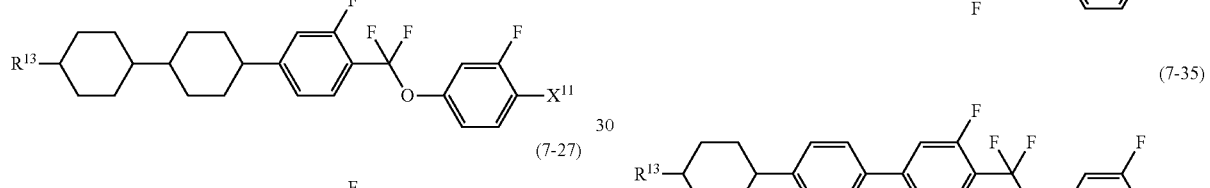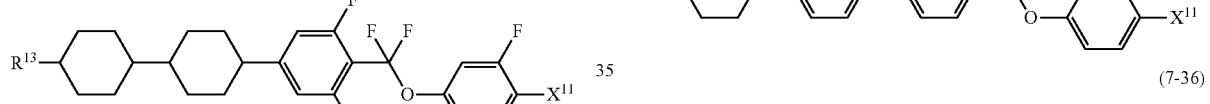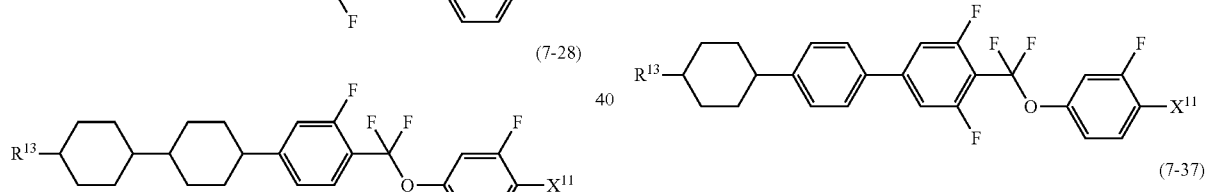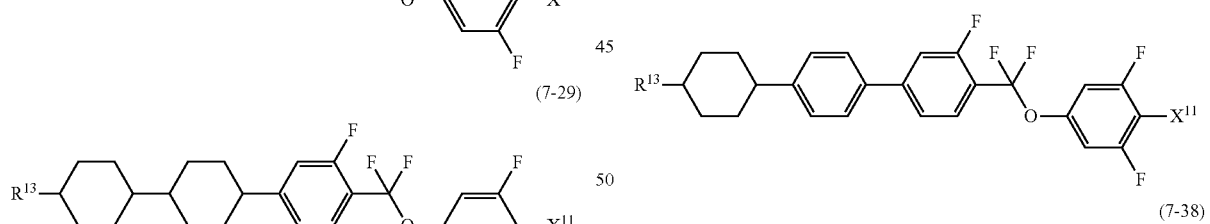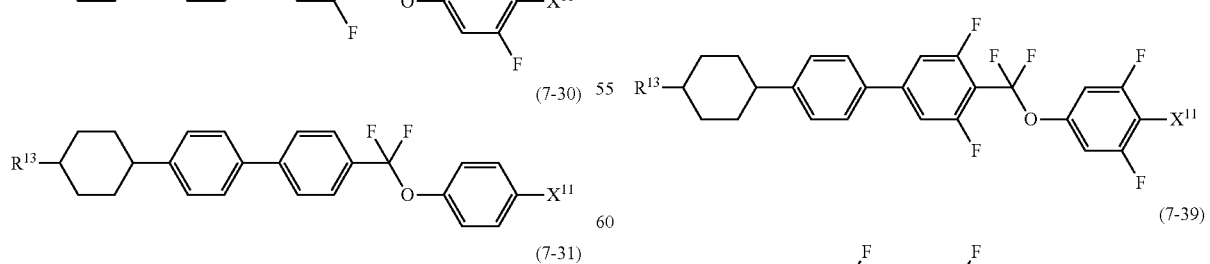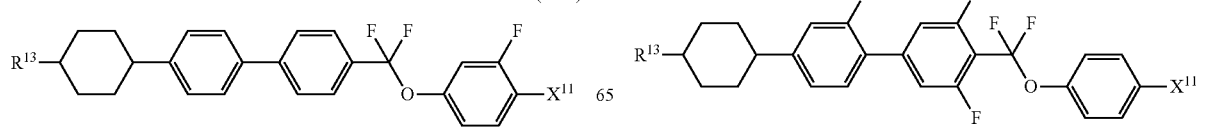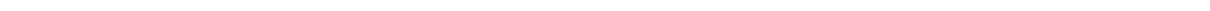

(7-40)
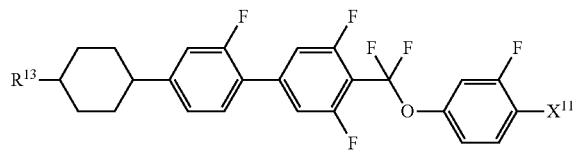
(7-41)
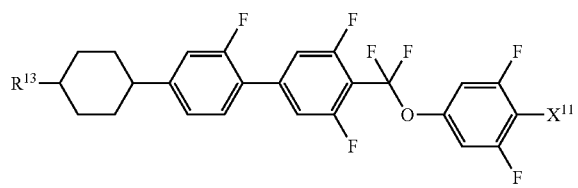
(7-42)
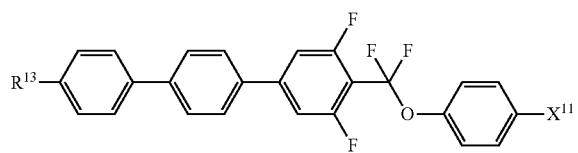
(7-43)
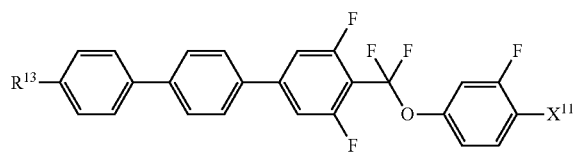
(7-44)
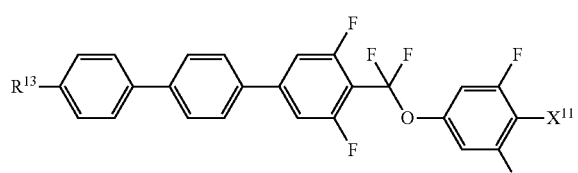
(7-45)
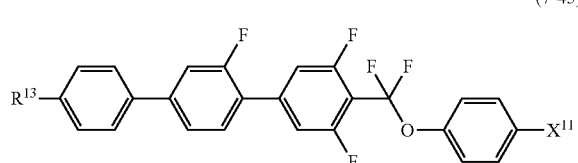
(7-46)
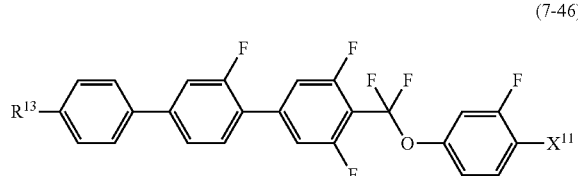
(7-47)
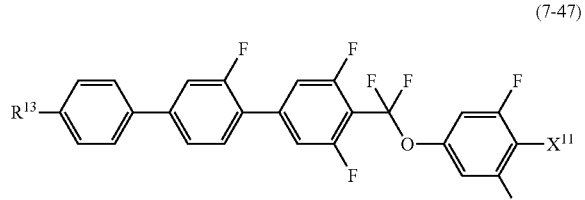
(7-48)
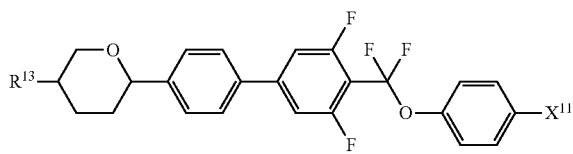
(7-49)
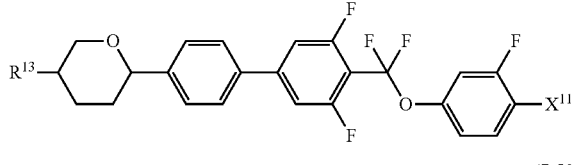
(7-50)
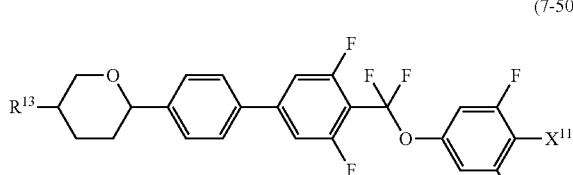
(7-51)
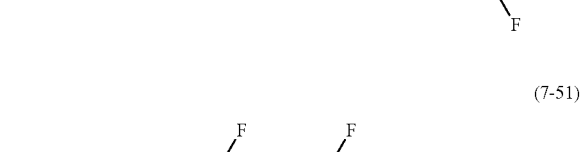
(7-52)
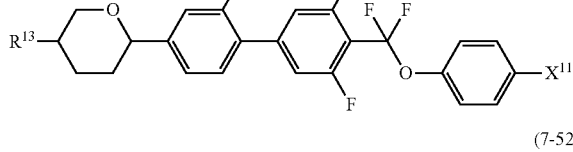
(7-53)
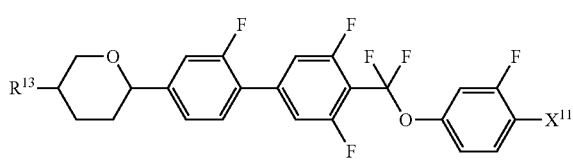
(7-54)
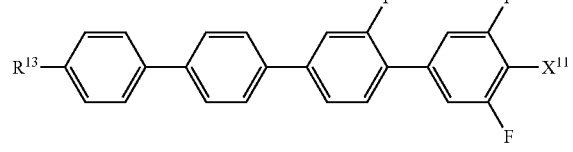
(7-55)
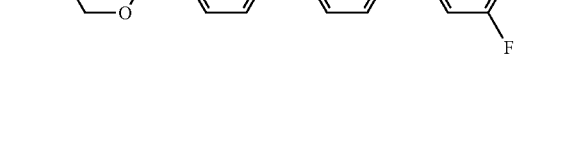

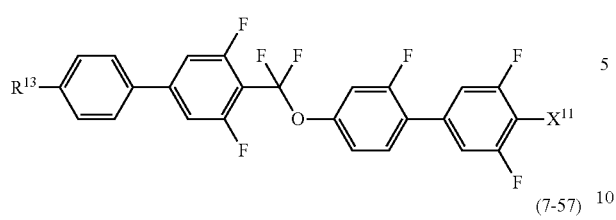 (7-56)

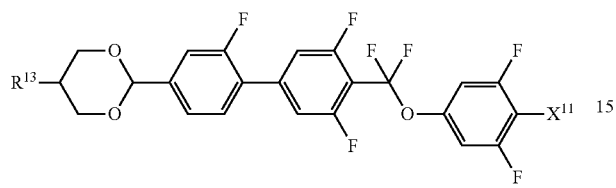 (7-57)

Component C has the positive dielectric anisotropy, and superb stability to heat and light, and therefore is used when a composition for the IPS mode, the FFS mode, the OCB mode or the like is prepared. A content of component C is suitably in the range of approximately 1% by weight to approximately 99% by weight, preferably in the range of approximately 10% by weight to approximately 97% by weight, and further preferably in the range of approximately 40% by weight to approximately 95% by weight, based on the weight of the liquid crystal composition. When component C is added to a composition having the negative dielectric anisotropy, the content of component C is preferably approximately 30% by weight or less. Addition of component C allows adjustment of the elastic constant of the composition and adjustment of a voltage-transmittance curve of the device.

Component D is compound (8) in which a right-terminal group is —C≡N or —C≡C—C≡N. Preferred examples of component D include compounds (8-1) to (8-64). In the compounds, $R^{14}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and $X^{12}$ is —C≡N or —C≡C—C≡N.

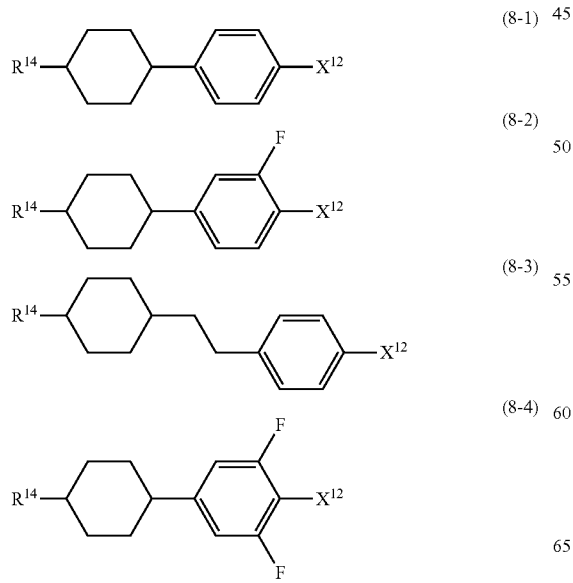

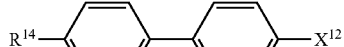 (8-5)

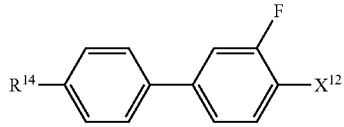 (8-6)

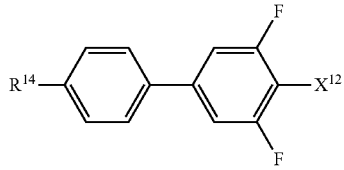 (8-7)

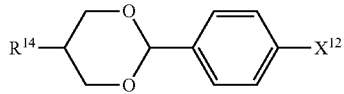 (8-8)

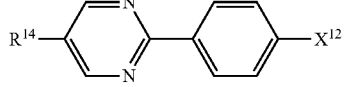 (8-9)

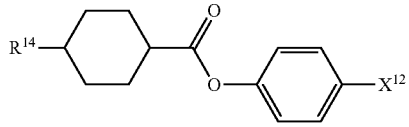 (8-10)

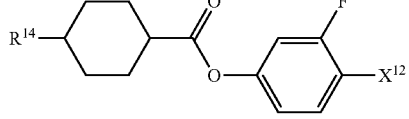 (8-11)

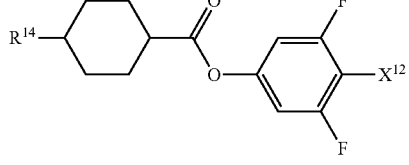 (8-12)

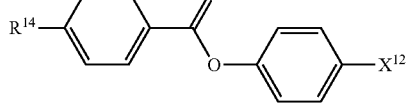 (8-13)

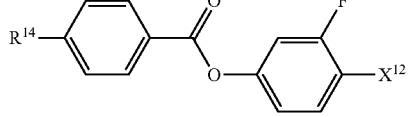 (8-14)

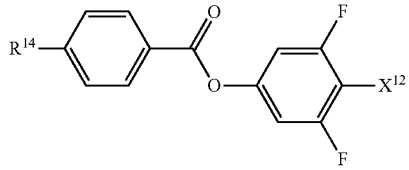 (8-15)

(8-16) 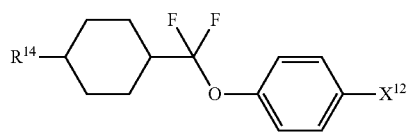
(8-17) 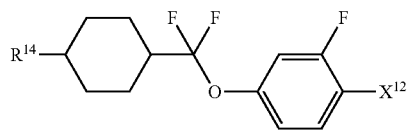
(8-18) 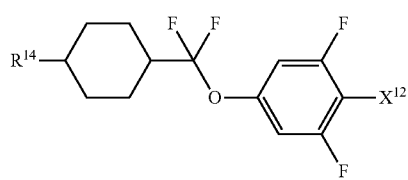
(8-19) 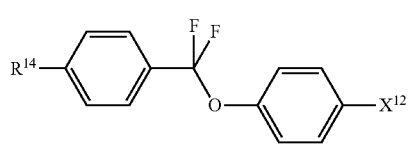
(8-20) 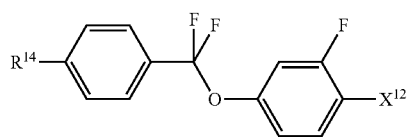
(8-21) 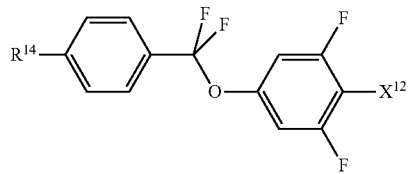
(8-22) 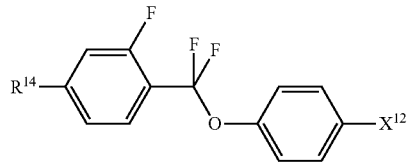
(8-23) 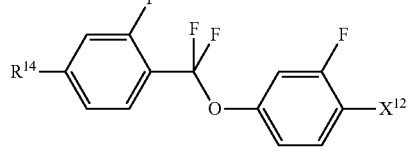
(8-24) 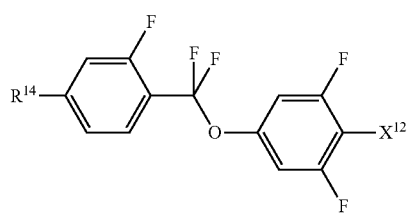
(8-25) 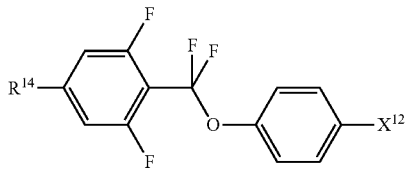
(8-26) 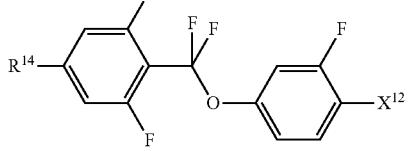
(8-27) 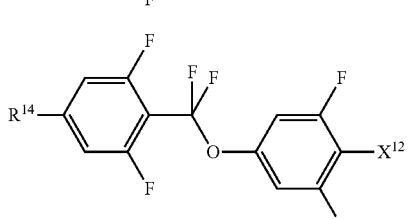
(8-28) 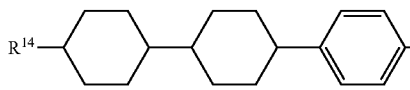
(8-29) 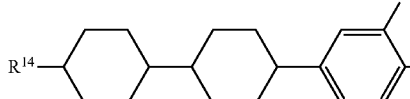
(8-30) 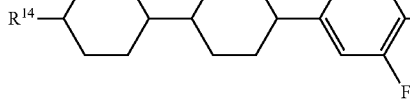
(8-31) 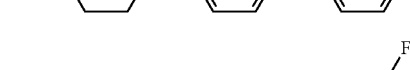
(8-32) 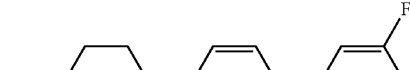
(8-33) 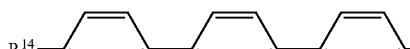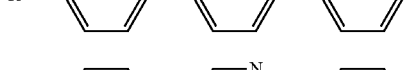
(8-34) 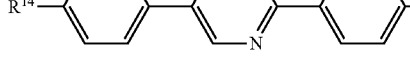
(8-35) 

(8-36)
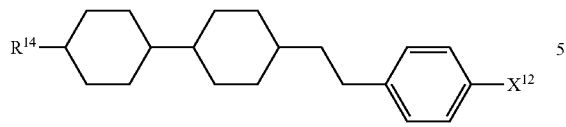
(8-37)
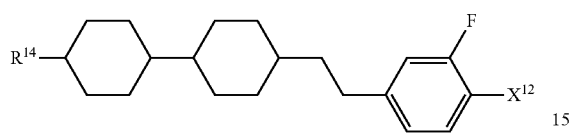
(8-38)
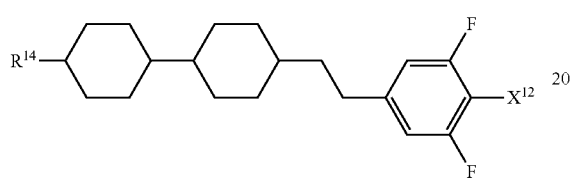
(8-39)
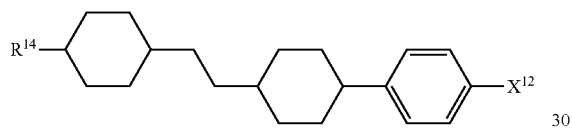
(8-40)
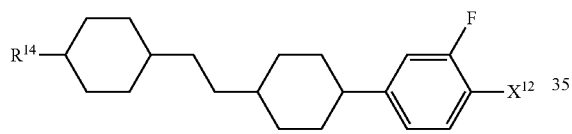
(8-41)
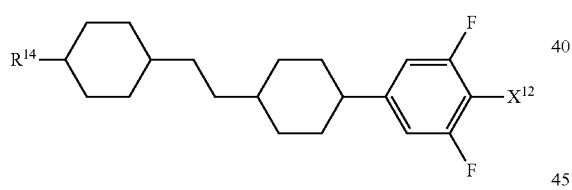
(8-42)
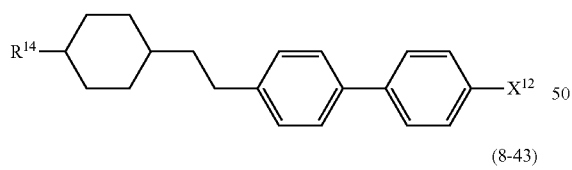
(8-43)
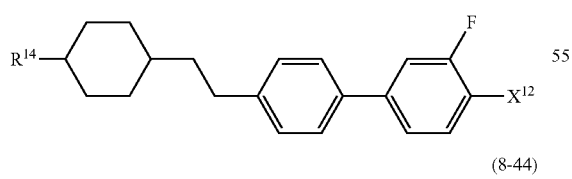
(8-44)
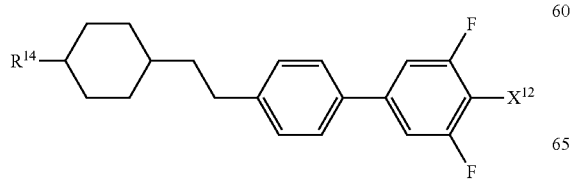
(8-45)
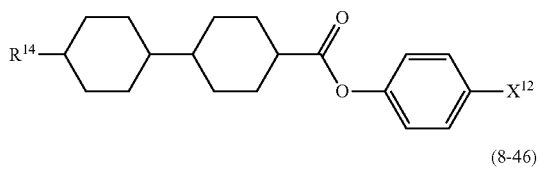
(8-46)
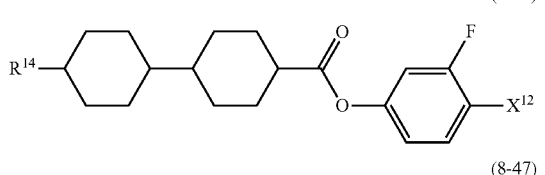
(8-47)
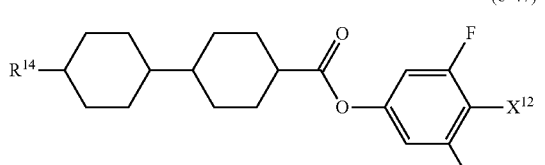
(8-48)
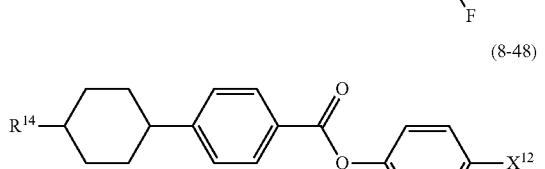
(8-49)
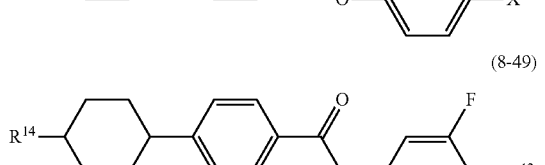
(8-50)
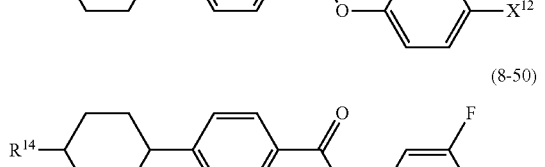
(8-51)
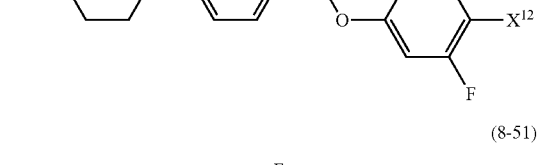
(8-52)
(8-53)
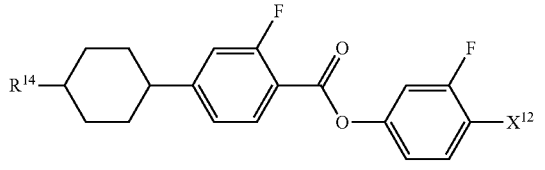

(8-54)
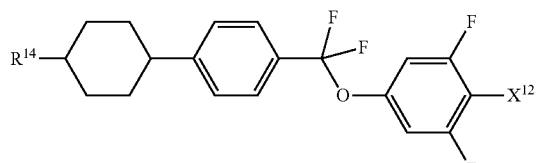

(8-55)
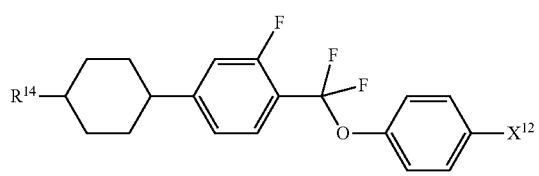

(8-56)
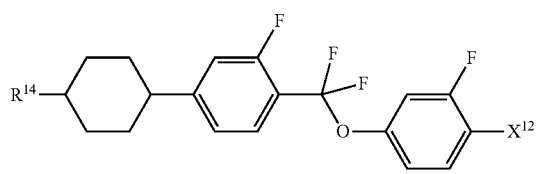

(8-57)
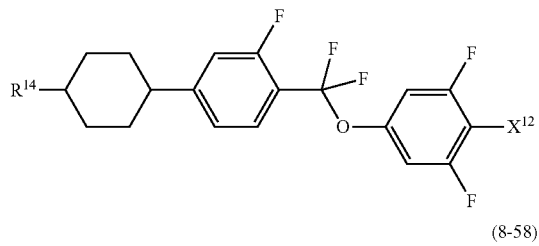

(8-58)

(8-59)
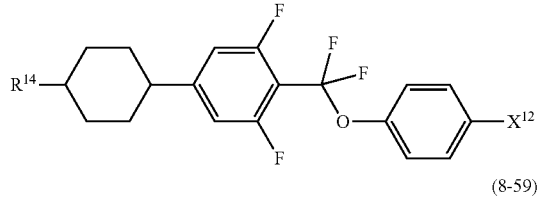

(8-60)
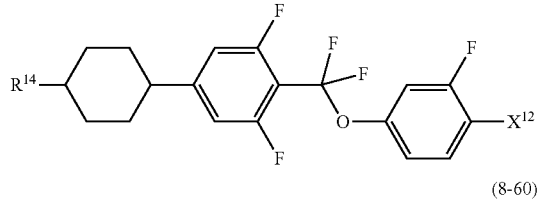

(8-61)
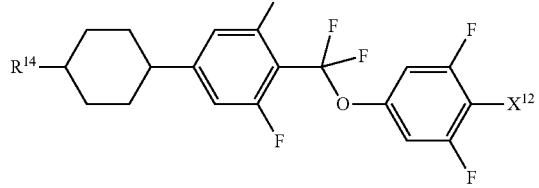

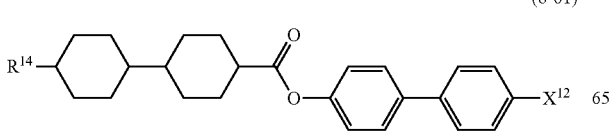

(8-62)
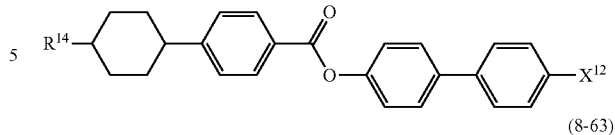

(8-63)
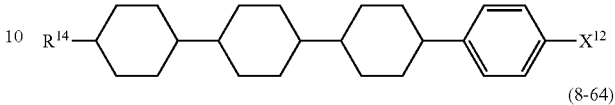

(8-64)
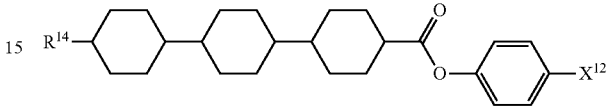

Component D has the positive dielectric anisotropy and a value thereof is large, and therefore is used when a composition for the TN mode or the like is prepared. Addition of component D can increase the dielectric anisotropy of the composition. Component D is effective in extending the temperature range of the liquid crystal phase, adjusting the viscosity or adjusting the optical anisotropy. Component D is also useful for adjustment of the voltage-transmittance curve of the device.

When a composition for the TN mode or the like is prepared, a content of component D is suitably in the range of approximately 1% by weight to approximately 99% by weight, preferably in the range of approximately 10% by weight to approximately 97% by weight, and further preferably in the range of approximately 40% by weight to approximately 95% by weight, based on the weight of the liquid crystal composition. When component D is added to a composition having the negative dielectric anisotropy, the content of component D is preferably approximately 30% by weight or less. Addition of component D allows adjustment of the elastic constant of the composition and adjustment of the voltage-transmittance curve of the device.

Component E includes compounds (9) to (15). The compounds have phenylene in which hydrogen in lateral positions are replaced by two pieces of halogen, such as 2,3-difluoro-1,4-phenylene. Preferred examples of component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$ and $R^{16}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and $R^{17}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine.

(9-1)
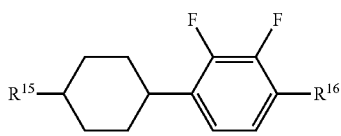

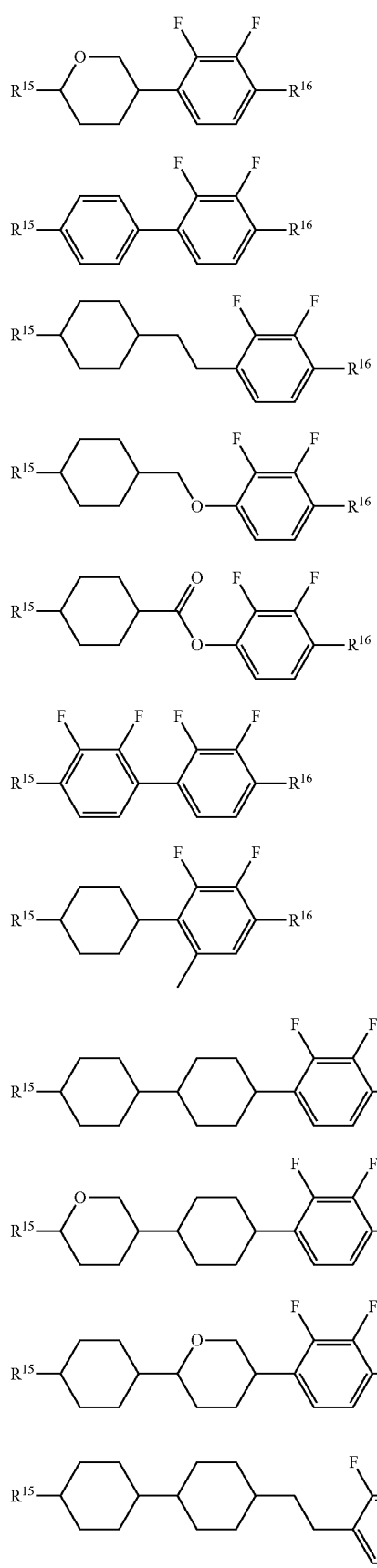
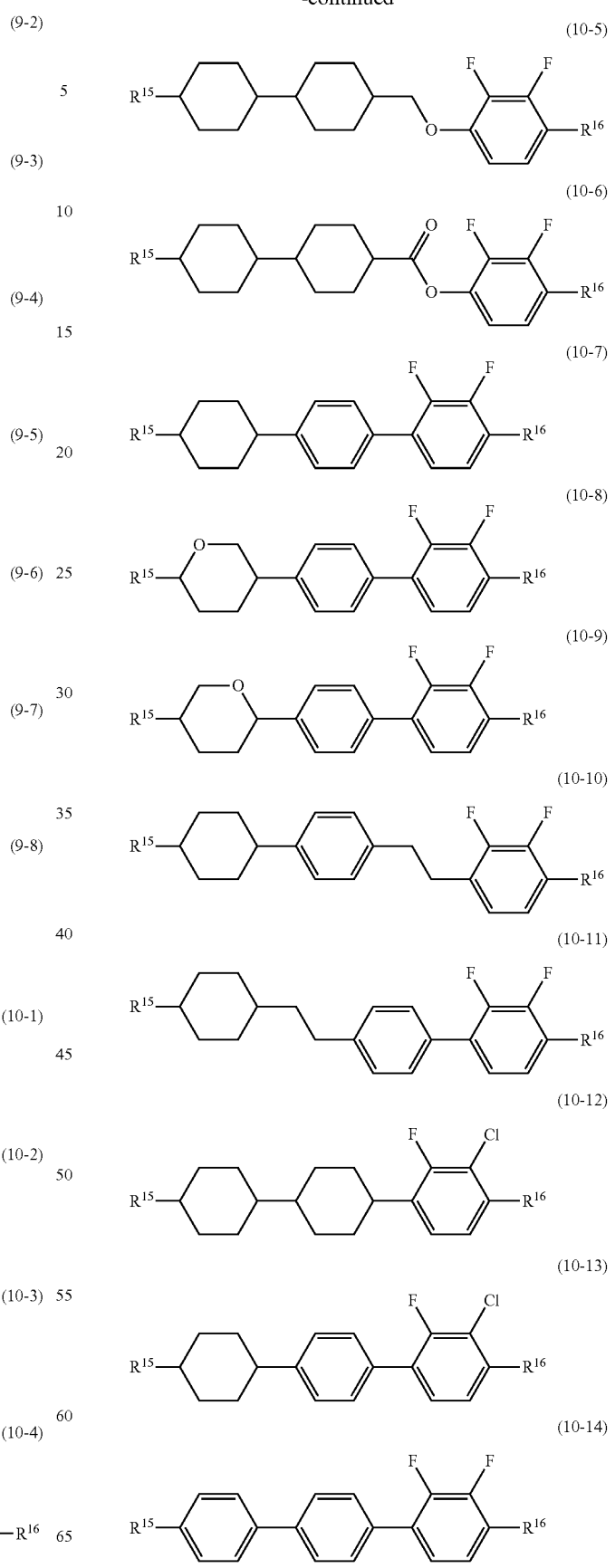

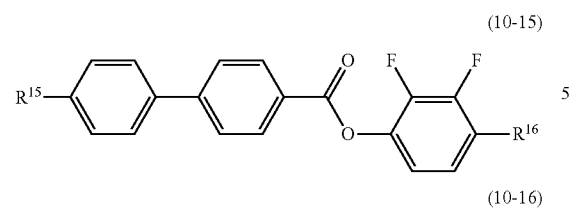
(10-15)
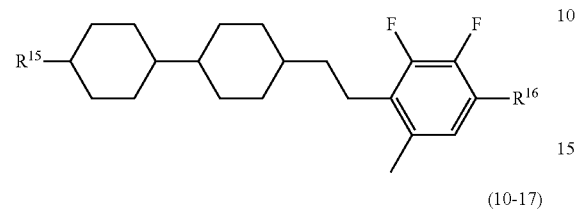
(10-16)
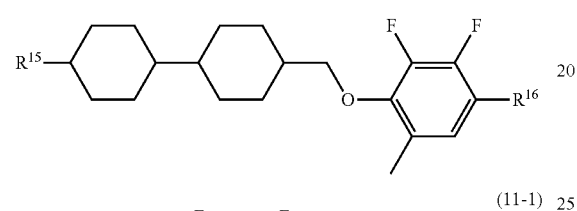
(10-17)
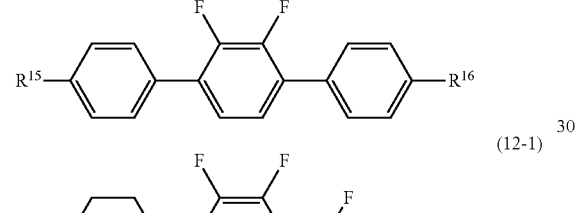
(11-1)
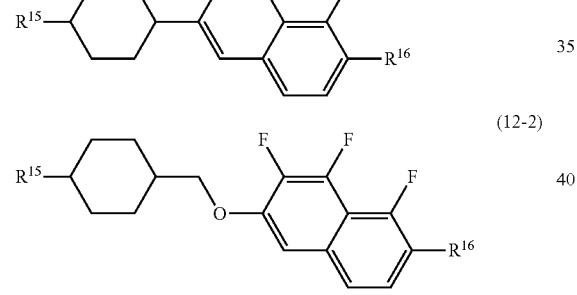
(12-1)
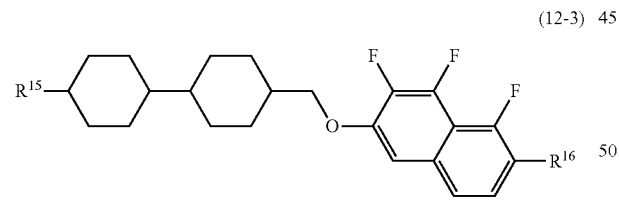
(12-2)
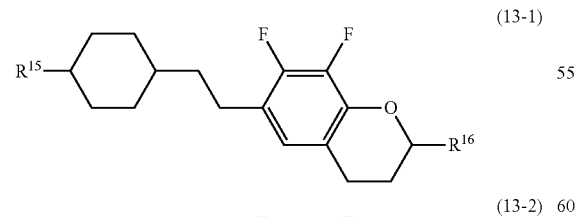
(12-3)
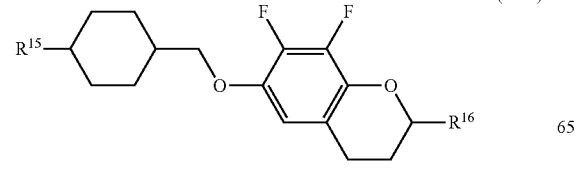
(13-1)
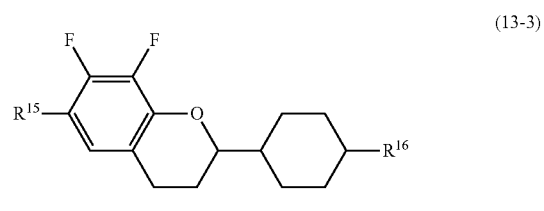
(13-2)
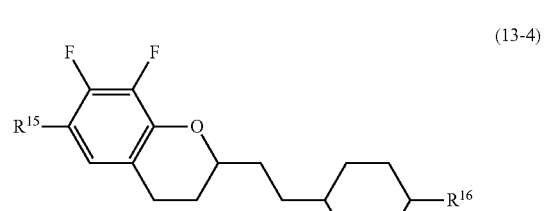
(13-3)
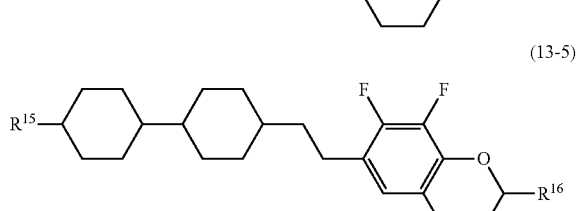
(13-4)
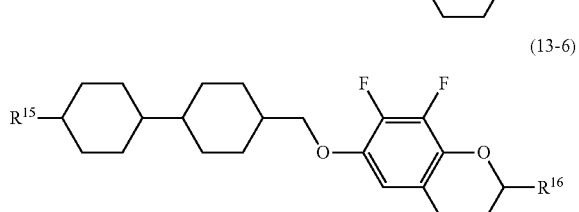
(13-5)
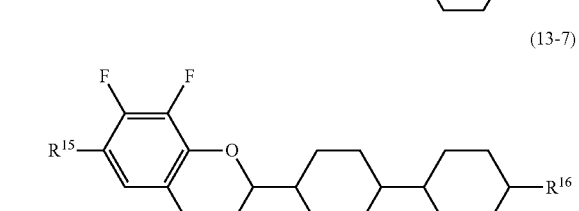
(13-6)
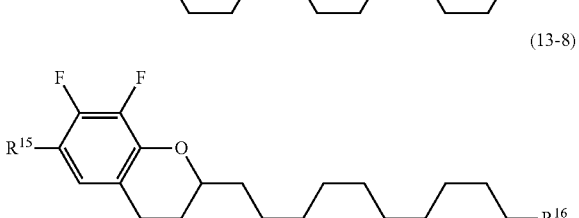
(13-7)
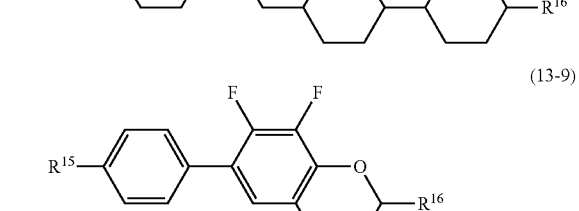
(13-8)
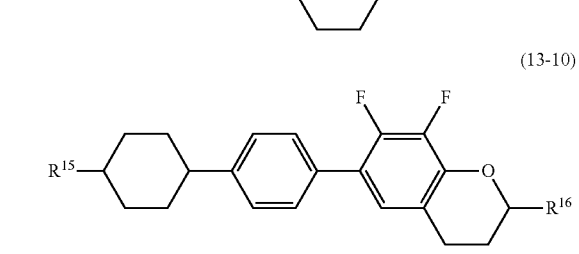
(13-9)
(13-10)

(13-11)
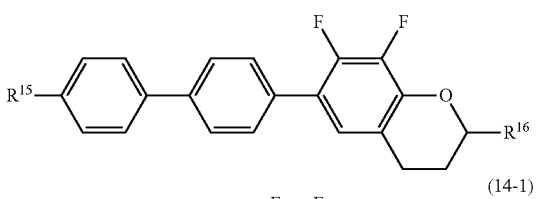

(14-1)
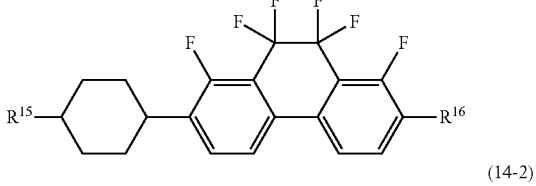

(14-2)
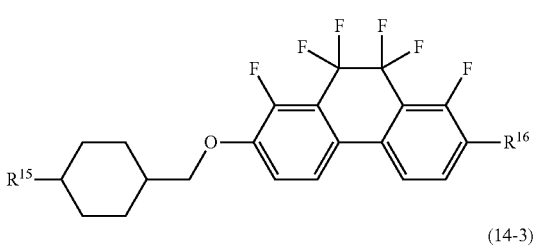

(14-3)
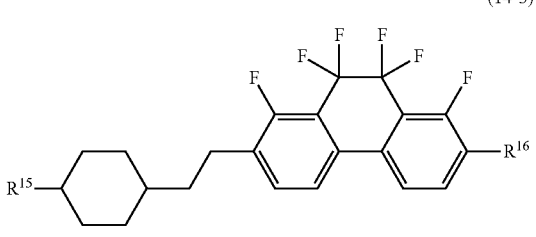

(15-1)
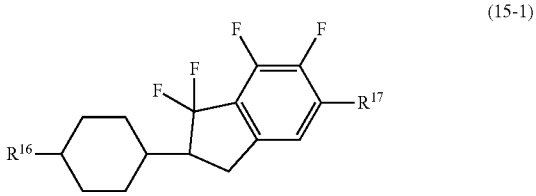

(15-2)

(15-3)
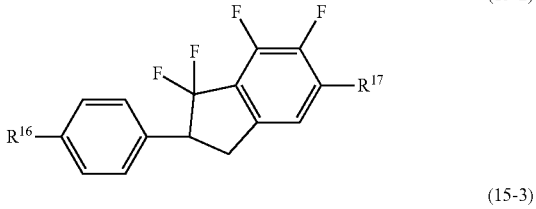

Component E has a negatively large dielectric anisotropy. Component E is used when a composition for the IPS mode, the VA mode, the PSA mode or the like is prepared. As a content of component E is increased, the dielectric anisotropy of the composition is negatively increased, but the viscosity is increased. Thus, as long as a desired value of threshold voltage of the device is met, the content is preferably as small as possible. When the dielectric anisotropy at a degree of −5 is taken into account, the content is preferably approximately 40% by weight or more in order to allow a sufficient voltage driving.

Among types of component E, compound (9) is a bicyclic compound, and therefore is effective in decreasing the viscosity, adjusting the optical anisotropy or increasing the dielectric anisotropy. Compounds (10) and (11) are a tricyclic compound, and therefore are effective in increasing the maximum temperature, the optical anisotropy or the dielectric anisotropy. Compounds (12) to (15) are effective in increasing the dielectric anisotropy.

When a composition for the IPS mode, the VA mode or the PSA mode is prepared, the content of component E is preferably approximately 40% by weight or more, and further preferably in the range of approximately 50% by weight to approximately 95% by weight, based on the weight of the liquid crystal composition. When component E is added to a composition having the positive dielectric anisotropy, the content of component E is preferably approximately 30% by weight or less. Addition of component E allows adjustment of the elastic constant of the composition and adjustment of the voltage-transmittance curve of the device.

The liquid crystal composition satisfying at least one of physical properties such as the high stability to heat and light, the high maximum temperature, the low minimum temperature, the small viscosity, the suitable optical anisotropy, the large dielectric anisotropy, the large specific resistance and the suitable elastic constant can be prepared by suitably combining components B, C, D and E described above. A liquid crystal compound different from components B, C, D and E may be added, when necessary.

3-2. Additive

A liquid crystal composition is prepared according to a known method. For example, the component compounds are mixed and dissolved in each other by heating. According to an application, an additive may be added to the composition. Specific examples of the additive include the polymerizable compound, the polymerization initiator, the polymerization inhibitor, the optically active compound, the antioxidant, the ultraviolet light absorber, the light stabilizer, the heat stabilizer, the dye and the antifoaming agent. Such additives are well known to those skilled in the art, and described in literature.

In a liquid crystal display device having the polymer sustained alignment (PSA) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which response time is shortened and image persistence is improved is prepared.

Preferred examples of the polymerizable compound include an acrylate, a methacrylate, a vinyl compound, a vinyloxy compound, a propenyl ether compound, an epoxy compound (oxirane, oxetane) and a vinyl ketone. Further preferred examples include a compound having at least one acryloyloxy, and a compound having at least one methacryloyloxy. Still further preferred examples also include a compound having both acryloyloxy and methacryloyloxy.

Still further preferred examples include compounds (M-1) to (M-17) In the compounds, $R^{25}$ to $R^{31}$ are independently hydrogen or methyl; s, v and x are independently 0 or 1; t and u are independently an integer from 1 to 10. $L^{21}$ to $L^{26}$ are independently hydrogen or fluorine; and $L^{27}$ and $L^{28}$ are independently hydrogen, fluorine or methyl.

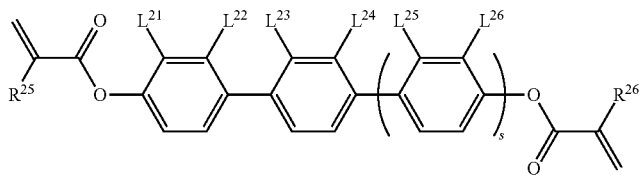
(M-1)
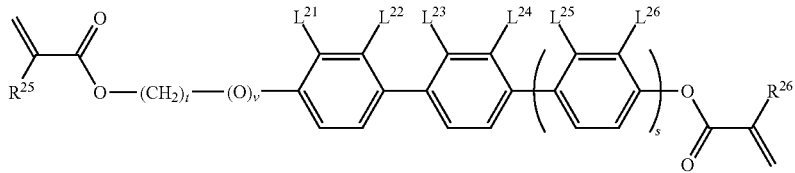
(M-2)
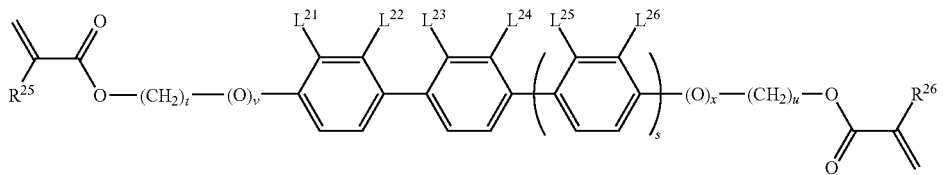
(M-3)
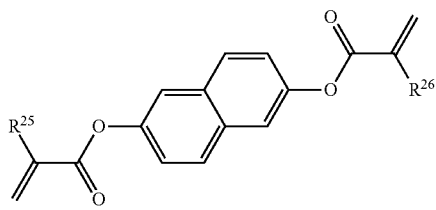
(M-4)
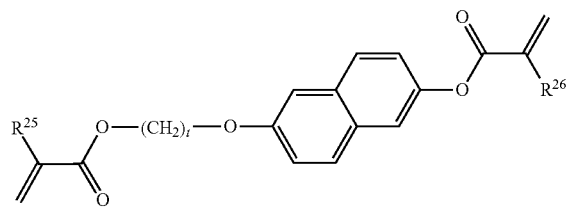
(M-5)
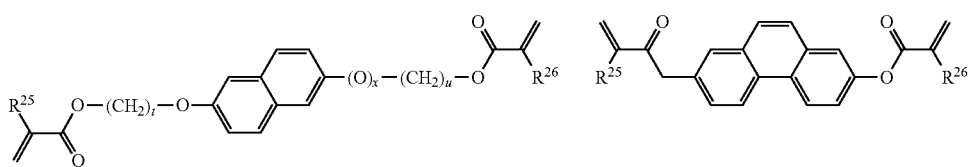
(M-6)
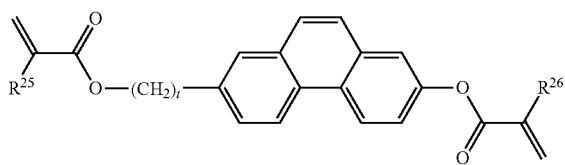
(M-7)
(M-8)
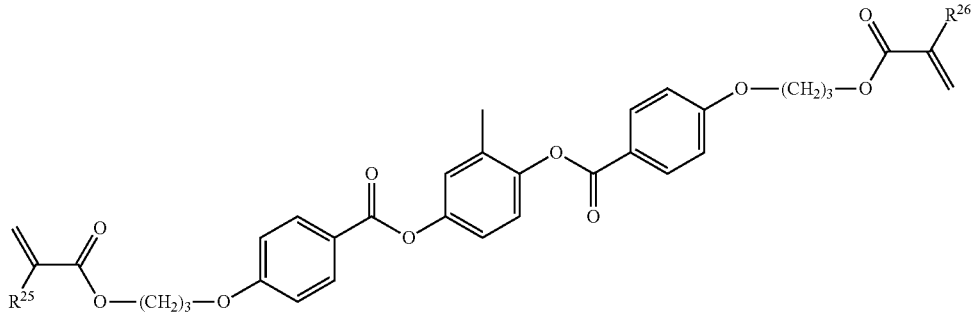
(M-9)

-continued
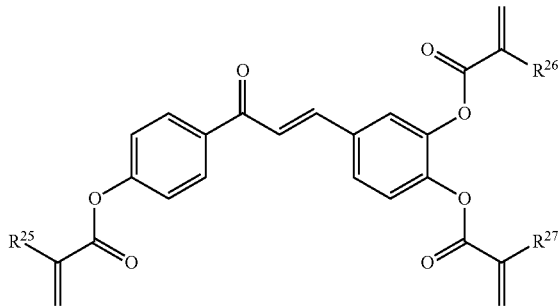
(M-10)
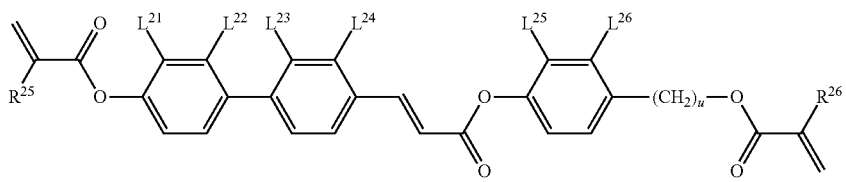
(M-11)
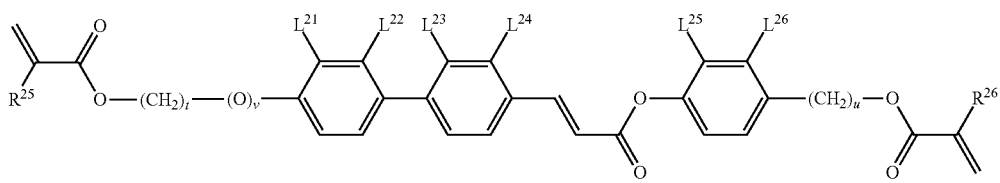
(M-12)
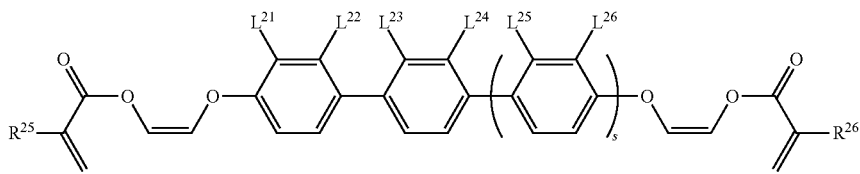
(M-13)
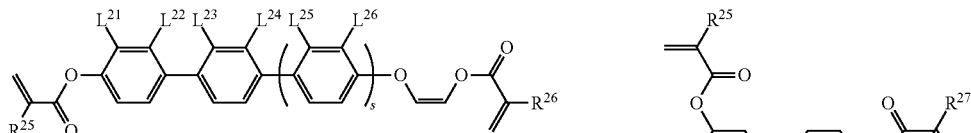
(M-14)
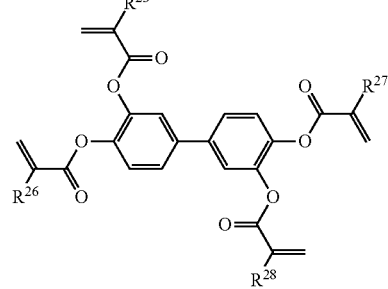
(M-15)
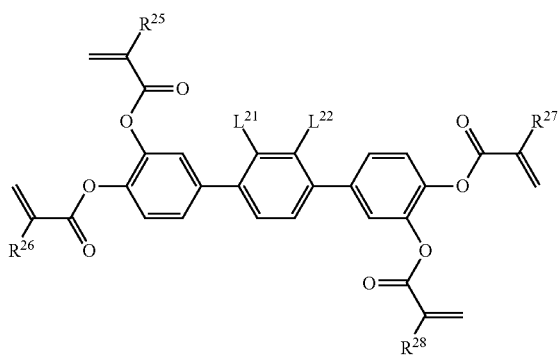
(M-16)
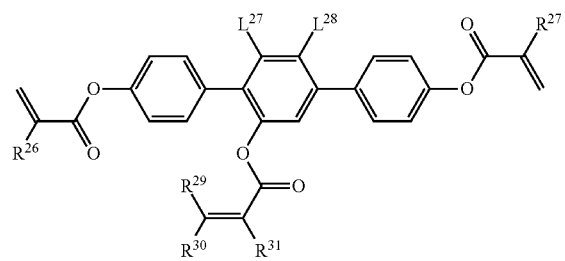
(M-17)

The polymerizable compound can be rapidly polymerized by adding the polymerization initiator. An amount of a remaining polymerizable compound can be decreased by optimizing reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed without addition of the polymerization initiator. A preferred wavelength of irradiation light is in the range of approximately 150 nanometers to approximately 500 nanometers. A further preferred wavelength is in the range of approximately 250 nanometers to approximately 450 nanometers, and a most preferred wavelength is in the range of approximately 300 nanometers to approximately 400 nanometers.

Upon storing the polymerizable compound, the polymerization inhibitor may be added thereto in order to prevent polymerization. The polymerizable compound is ordinarily added to the composition without removing the polymerization inhibitor. Examples of the polymerization inhibitor include hydroquinone, a hydroquinone derivative such as methylhydroquinone, 4-t-butylcatechol, 4-methoxyphenol and phenothiazine.

The optically active compound is effective in inducing a helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

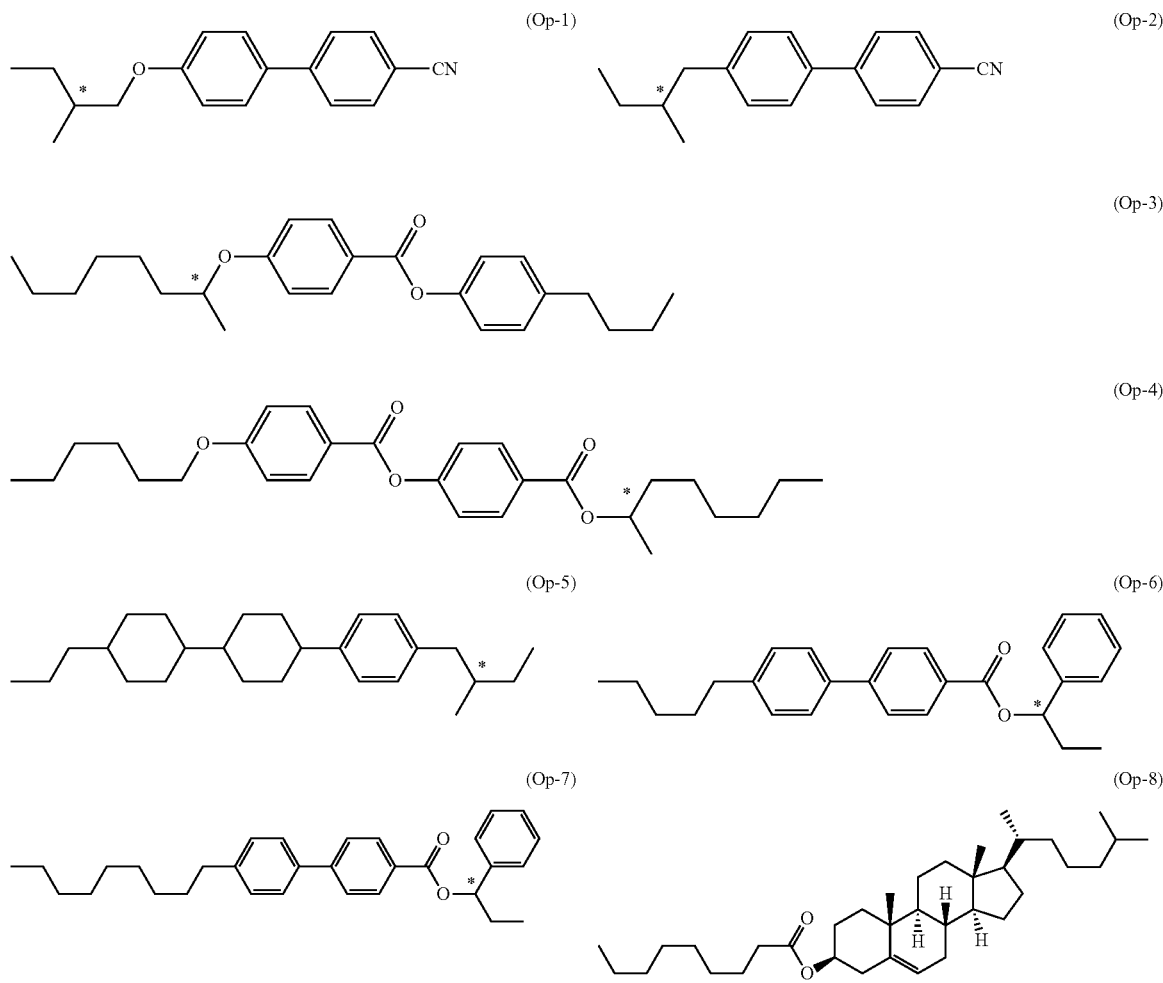

-continued
(Op-9)
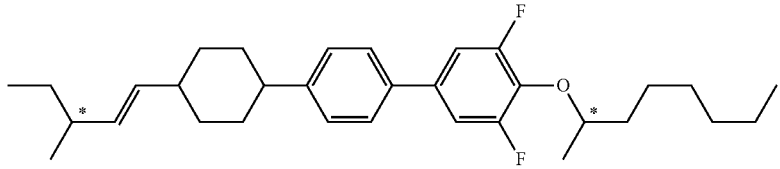
(Op-10)
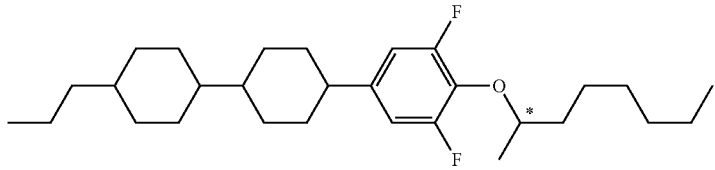
(Op-11)
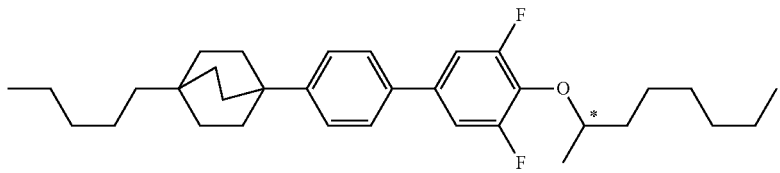
(Op-12)
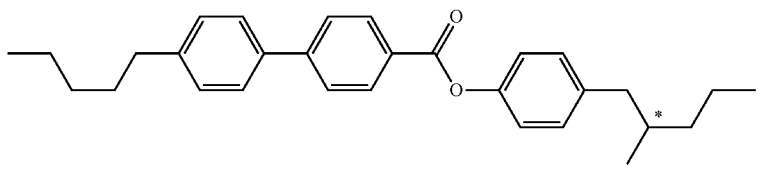
(Op-13)
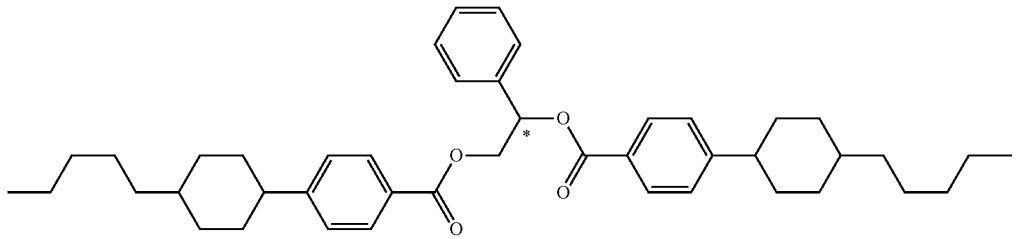
(Op-14)
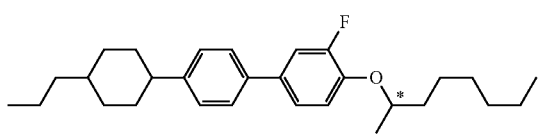
(Op-15)
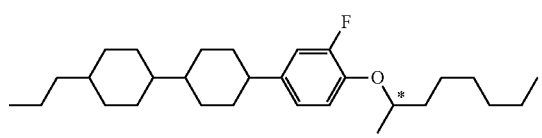
(Op-16)
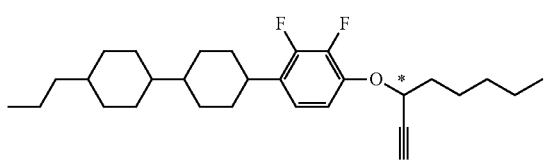
(Op-17)
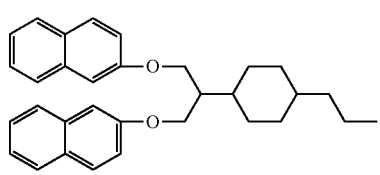

(Op-18)

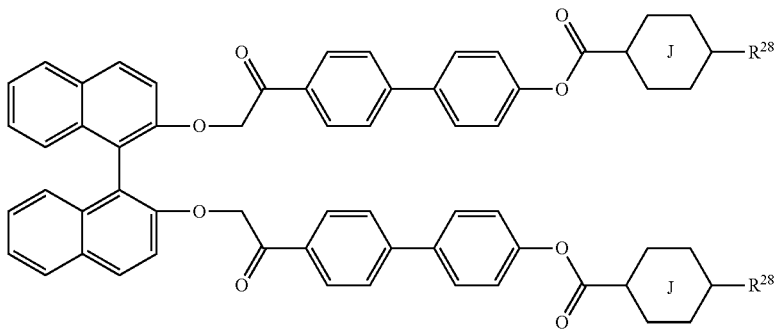

The antioxidant is effective for maintaining a large voltage holding ratio. Preferred examples of the antioxidant include compounds (AO-1) and (AO-2) described below; and IRGANOX 415, IRGANOX 565, IRGANOX 1010, IRGANOX 1035, IRGANOX 3114 and IRGANOX 1098 (trade names: BASF SE). The ultraviolet light absorber is effective in preventing a decrease of the maximum temperature. Preferred examples of the ultraviolet light absorber include a benzophenone derivative, a benzoate derivative and a triazole derivative. Specific examples include compounds (AO-3) and (AO-4) described below; TINUVIN 329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Preferred examples of the light stabilizer include compounds (AO-5) and (AO-6) described below; and TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). A dichroic dye such as an azo dye or an anthraquinone dye is added to the composition to be adapted for a device having a guest host (GH) mode. The antifoaming agent is effective in preventing foam formation. Preferred examples of the antifoaming agent include dimethyl silicone oil and methylphenyl silicone oil.

(AO-1)

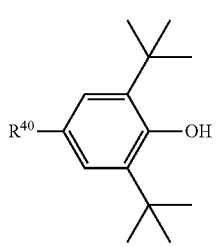

(AO-2)

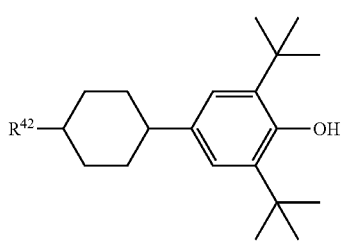

(AO-3)

(AO-4)

(AO-5)

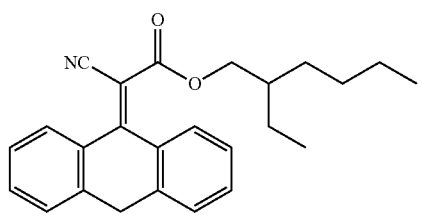

(AO-6)

In compound (AO-1), $R^{40}$ is alkyl having 1 to 20 carbons, alkoxy having 1 to 20 carbons, $-COOR^{41}$ or $-CH_2CH_2COOR^{41}$, in which, $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O (oxygen radical); ring G is 1,4-cyclohexylene or 1,4-phenylene; and z is 1, 2 or 3.

4. Liquid Crystal Display Device

The liquid crystal composition can be used for the liquid crystal display device having an operating mode such as the PC mode, the TN mode, the STN mode, the OCB mode and the PSA mode, and driven by an active matrix. The composition can also be used for the liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated herein. The composition can also be used for a polymer dispersed liquid crystal display device (PDLCD) and a polymer network liquid crystal display device (PNLCD). In the compositions, a lot of polymerizable compounds are added. On the other hand, when an amount of adding the polymerizable compound is approximately 10% by weight or less based on the weight of the liquid crystal composition, the liquid crystal display device having the PSA mode can be prepared. A preferred proportion is in the range of approximately 0.1% by weight to approximately 2% by weight. A further preferred proportion is in the range of approximately 0.2% by weight to approximately 1.0% by weight. The device having the PSA mode can be driven by the driving mode such as an active matrix mode and a passive matrix mode. Such devices can be applied to any of the reflective type, the transmissive type and the transflective type.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples (including Synthesis Examples and Use Examples). The invention is not limited by the Examples. The invention includes a mixture of a composition in Use Example 1 and a composition in Use Example 2. The invention also includes a composition prepared by mixing at least two of compositions in Use Examples.

1. Example of Compound (1)

Compound (1) was prepared according to procedures described below. A compound prepared was identified by a method such as an NMR analysis. Physical properties of the compound and the composition and characteristics of a device were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In the explanation of a nuclear magnetic resonance spectrum, s, d, t, q, quin, sex and m stand for a singlet, a doublet, a triplet, a quartet, a quintet, a sextet and a multiplet, and br being broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a detector (FID) part were set to 300° C. and 300° C., respectively. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

HPLC Analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight % solution, and then 1 microliter of the solution was injected into a sample chamber. As a recorder, C-R7Aplus made by Shimadzu Corporation was used.

Ultraviolet-Visible Spectrophotometry: For measurement, PharmaSpec UV-1700 made by Shimadzu Corporation was used. A detection wavelength was adjusted in the range of 190 nanometers to 700 nanometers. A sample was dissolved in acetonitrile, and prepared to be a solution of 0.01 millimole per liter, and measurement was carried out by putting the solution in a quartz cell (optical path length 1 cm).

Sample for measurement: Upon measuring phase structure and a transition temperature (a clearing point, a melting point, a polymerization starting temperature or the like), a compound itself was used as a sample. Upon measuring physical properties such as a maximum temperature of a nematic phase, viscosity, optical anisotropy and dielectric anisotropy, a mixture of a compound and a base liquid crystal was used as a sample.

When the sample prepared by mixing the compound with the base liquid crystal was used, an extrapolated value was calculated according to the following formula and the calculated value was described: [extrapolated value]=(100×[measured value of a sample]−[% by weight of a base liquid crystal]×[measured value of the base liquid crystal])/[% by weight of a compound].

Base liquid crystal (A): When the dielectric anisotropy of the compound was zero or positive, base liquid crystal (A) described below was used. A proportion of each component was expressed in terms of % by weight.

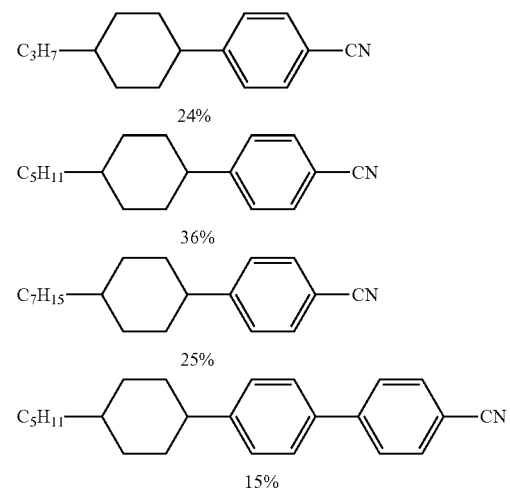

A ratio of the compound to base liquid crystal (A) was adjusted to (15% by weight:85% by weight). When crystals (or a smectic phase) precipitated at 25° C. at the ratio, a ratio of the compound to base liquid crystal (A) was changed in the order of (10% by weight:90% by weight), (5% by weight:95% by weight) and (1% by weight:99% by weight), and the sample was measured at a ratio at which no crystal (or no smectic phase) precipitated at 25° C. In addition, unless otherwise noted, the ratio of the compound to base liquid crystal (A) was (15% by weight: 85% by weight).

Base liquid crystal (B): In Comparative Example 1, base liquid crystal (B) having a fluorine-based compound described below as a component was used to compare compatibility at a low temperature. A proportion of a component of base liquid crystal (B) was expressed in terms of % by weight.

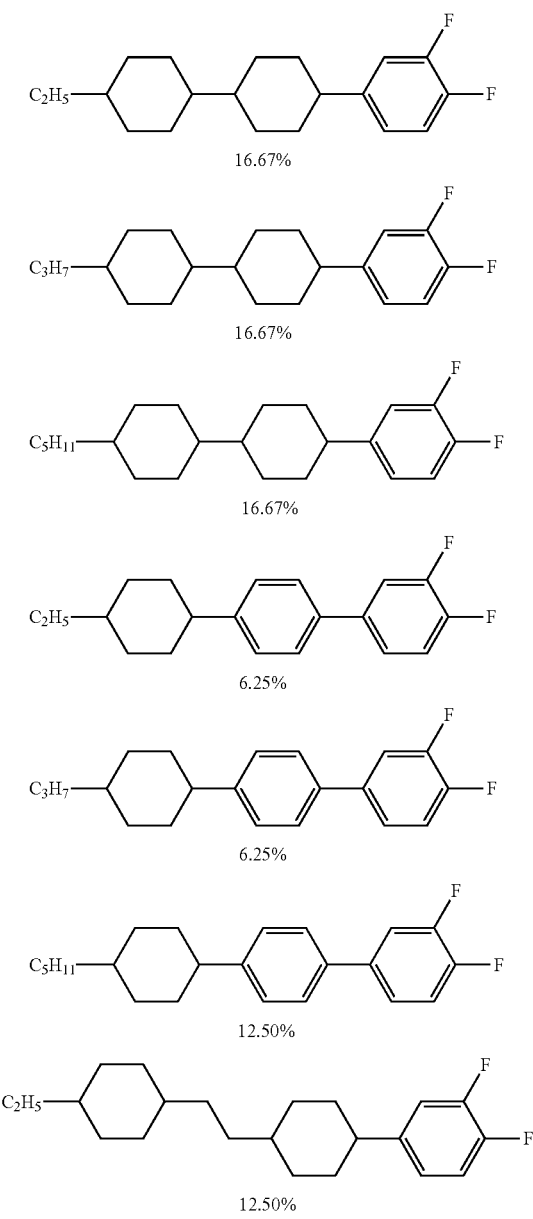

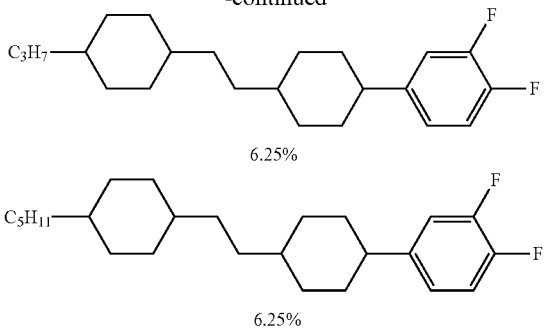

Measuring method: Measurement of physical properties was carried out by the methods described below. Most of the methods are described in the Standard of Japan Electronics and Information Technology Industries Association (hereinafter, abbreviated as JEITA) discussed and established in JEITA (JEITA ED-2521B). A modification of the methods were also used. No thin film transistor (TFT) was attached to a TN device used for measurement.

(1) Phase structure: A sample was placed on a hot plate of a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. The smectic phase and a nematic phase were expressed as S and N, respectively. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at low temperature: Samples in which the base liquid crystal and the compound were mixed for proportions of the compounds to be 20% by weight, 15% by weight, 10% by weight, 5% by weight, 3% by weight and 1% by weight were prepared, and put in glass vials. After the glass vials were kept in freezers at −10° C. or −20° C. for a predetermined period of time, whether or not crystals or a smectic phase precipitated was observed.

(4) Maximum temperature of nematic phase ($T_{NI}$ or NI; ° C.): A sample was placed on a hot plate of a melting point apparatus equipped with a polarizing microscope, and was heated at a rate of 1° C. per minute. Temperature when part of the sample began to change from a nematic phase to an isotropic liquid was measured. When the sample was a mixture of compound (1) and the base liquid crystal, the maximum temperature was expressed as a symbol $T_{NI}$. When the sample was a mixture of compound (1) and a compound such as components B, C and D, the maximum temperature was expressed as a symbol NI. A higher limit of a temperature range of the nematic phase may be occasionally abbreviated as "maximum temperature."

(5) Minimum temperature of nematic phase ($T_c$; ° C.): Samples each having a nematic phase were put in glass vials and kept in freezers at temperatures of 0° C., –10° C., –20° C., –30° C. and –40° C. for 10 days, and then liquid crystal phases were observed. For example, when the sample maintained the nematic phase at –20° C. and changed to crystals or a smectic phase at –30° C., $T_c$ was expressed as $T_c$<–20° C. A lower limit of the temperature range of the nematic phase may be occasionally abbreviated as "minimum temperature."

(6) Viscosity (bulk viscosity; η; measured at 20° C.; mPa·s): A cone-plate (E type) rotational viscometer made by Tokyo Keiki Inc. was used for measurement.

(7) Viscosity (rotational viscosity; γ1; measured at 25° C.; mPa·s): Measurement was carried out according to a method described in M. Imai et al., Molecular Crystals and Liquid Crystals, Vol. 259, 37 (1995). A sample was put in a TN device in which a twist angle was 0 degrees and a distance between two glass substrates (cell gap) was 5 micrometers. Voltage was applied stepwise to the device in the range of 16 V to 19.5 V at an increment of 0.5V. After 0.2 second without voltage application, voltage was applied repeatedly under conditions of only one rectangular wave (rectangular pulse; 0.2 second) and no voltage application (2 seconds). A peak current and a peak time of a transient current generated by the applied voltage were measured. A value of rotational viscosity was obtained from the measured values according to calculating equation (8) on page 40 of the paper presented by M. Imai et al. A value of a dielectric anisotropy required for the calculation was determined using the device in which the rotational viscosity was measured and by a method described below.

(8) Optical anisotropy (refractive index anisotropy; measured at 25° C.; Δn): Measurement was carried out by an Abbe refractometer having a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when a direction of polarized light was perpendicular to a direction of rubbing. A value of optical anisotropy (Δn) was calculated from an equation: Δn=n∥–n⊥.

(9) Dielectric anisotropy (Δ∈; measured at 25° C.): A sample was put in a TN device in which a distance between two glass substrates (cell gap) was 9 micrometers and a twist angle was 80 degrees. Sine waves (10 V, 1 kHz) were applied to the device, and after 2 seconds, a dielectric constant (∈∥) of liquid crystal molecules in a major axis direction was measured. Sine waves (0.5 V, 1 kHz) were applied to the device, and after 2 seconds, a dielectric constant (∈⊥) of the liquid crystal molecules in a minor axis direction was measured. A value of dielectric anisotropy was calculated from an equation: Δ∈=∈∥–∈⊥.

(10) Elastic constant (K; measured at 25° C.; pN): For measurement, HP4284A LCR Meter made by Yokogawa-Hewlett-Packard Co. was used. A sample was put in a horizontal alignment device in which a distance between two glass substrates (cell gap) was 20 micrometers. An electric charge of 0 V to 20 V was applied to the device, and electrostatic capacity and applied voltage were measured. Measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed using a mean value of the thus determined $K_{11}$, $K_{22}$ and $K_{33}$.

(11) Threshold voltage (Vth; measured at 25° C.; V): For measurement, an LCD-5100 luminance meter made by Otsuka Electronics Co., Ltd. was used. A light source was a halogen lamp. A sample was put in a normally white mode TN device in which a distance between two glass substrates (cell gap) was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of voltage at 90% transmittance.

(12) Voltage holding ratio (VHR-1; measured at 25° C.; %): A TN device used for measurement had a polyimide alignment film and a distance between two glass substrates (cell gap) was 5 micrometers. A sample was put in the device, and then the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(13) Voltage holding ratio (VHR-2; measured at 80° C.; %): A voltage holding ratio was measured by a method described above except that the voltage holding ratio was measured at 80° C. in place of 25° C. The thus obtained value was expressed in terms of VHR-2.

(14) Specific resistance (ρ; measured at 25° C.; Ωcm): Into a vessel equipped with electrodes, 1.0 milliliter of a sample was injected. A DC voltage (10 V) was applied to the vessel, and a DC current after 10 seconds was measured. A specific resistance was calculated from the following equation: (specific resistance)={(voltage)×(electric capacity of a vessel)}/{(direct current)×(dielectric constant of vacuum)}.

(15) Response time (i; measured at 25° C.; ms): For measurement, an LCD-5100 luminance meter made by Otsuka Electronics Co., Ltd. was used. A light source was a halogen lamp. A low-pass filter was set to 5 kHz. A sample was put in a normally white mode TN device in which a distance between two glass substrates (cell gap) was 5.0 micrometers and a twist angle was 80 degrees. Rectangular waves (60 Hz, 5 V, 0.5 second) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr: rise time; millisecond) was a period of time required for a change in transmittance from 90% to 10%. A fall time (τf: fall time; millisecond) was a period of time required for a change in transmittance from 10% to 90%. A response time was expressed by a sum of the rise time and the fall time thus obtained.

Raw material: Solmix (registered trade name) A-11 is a mixture of ethanol (85.5%), methanol (13.4%) and 2-propanol (IPA; 1.1%), and was purchased from Japan Alcohol Trading Co., Ltd. Tetrahydrofuran may be occasionally abbreviated as THF. Tetrabutylammonium bromide may be occasionally abbreviated as TBAB. N,N-dimethylformamide may be occasionally abbreviated as DMF.

Synthesis Example 1

Synthesis of Compound (No. 10)

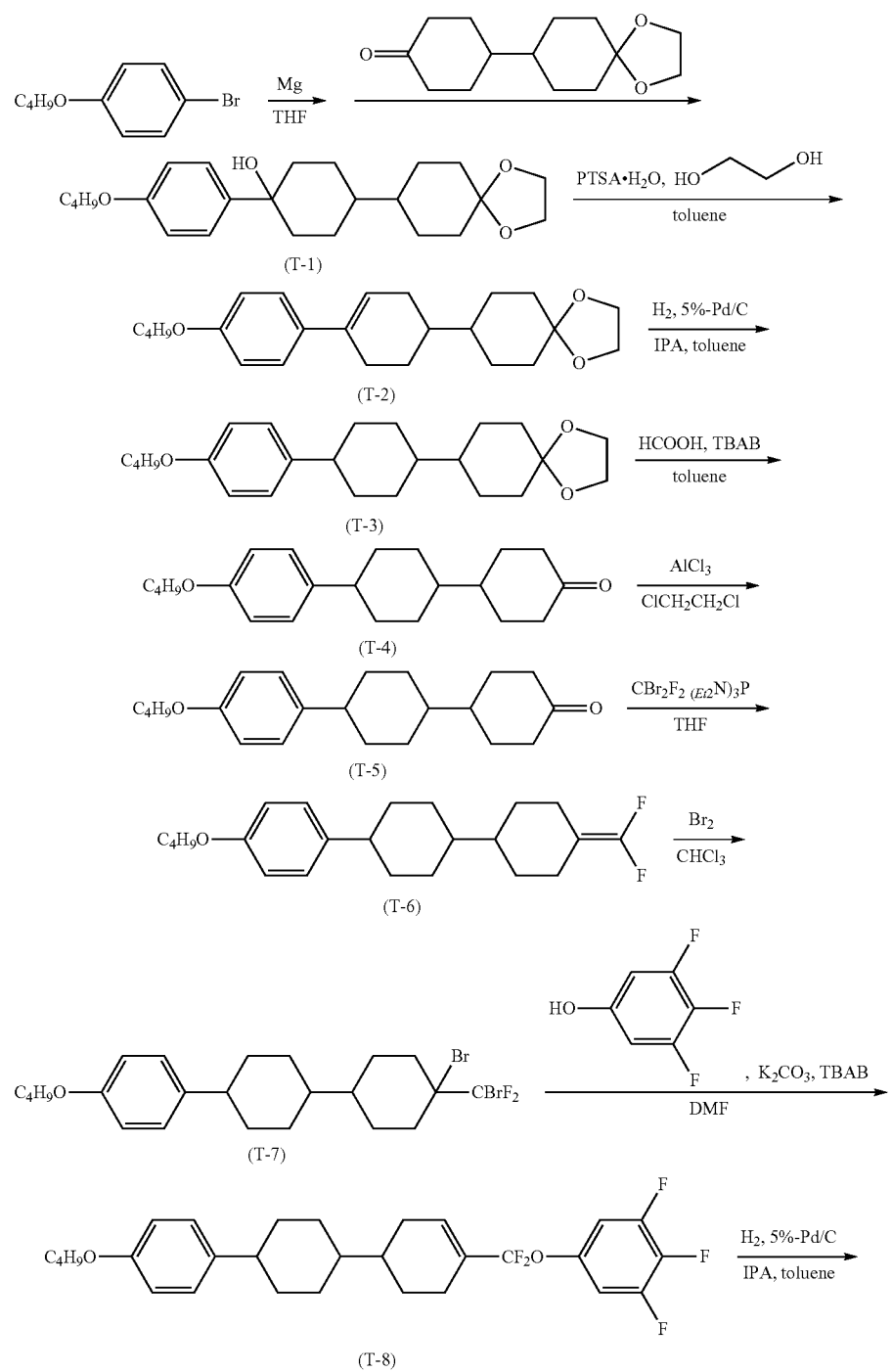

-continued

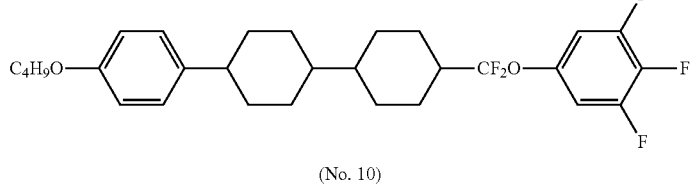

(No. 10)

First Step:

Under a nitrogen atmosphere, well-dried magnesium (2.77 g, 114.08 mmol) and THF (10 mL) were put in a reaction vessel, and the resulting mixture was heated to 40° C. Thereto, 1-bromo-4-butoxybenzene (25.00 g, 109.12 mmol) dissolved in THF (120 mL) was slowly added dropwise in the temperature range of 30° C. to 45° C., and the resulting mixture was further stirred for 30 minutes. A THF (120 mL) solution of 4-(1,4-dioxaspiro[4.5]decane-8-yl)cyclohexanone (23.64 g, 99.20 mmol) was slowly added dropwise in the temperature range of 30° C. to 50° C., and the resulting mixture was further stirred for 60 minutes. The resulting reaction mixture was cooled down to 25° C., and then poured into a saturated aqueous solution of ammonium chloride. The resulting mixture was subjected to extraction with toluene, and the resulting extract was washed with saturated sodium bicarbonate water and water, and then dried over anhydrous magnesium sulfate. The solvent was distilled off under reduced pressure to obtain a residue. The residue was purified by silica gel column chromatography (toluene/ethyl acetate=3/1, volume ratio) to obtain compound (T-1) (35.05 g, yield: 90.9%).

Second Step:

Under a nitrogen atmosphere, compound (T-1) (33.05 g, 85.06 mmol), 1,3-propanediol (5.28 g, 85.06 mmol), p-toluenesulfonic acid (0.49 g, 2.56 mmol) and toluene (330 mL) were put in a reaction vessel, and the resulting mixture was stirred for 3 hours under heating reflux while distilled water was removed. The resulting reaction mixture was cooled down to 25° C., and then poured into water. The resulting mixture was subjected to extraction with toluene, and the resulting extract was washed with saturated sodium bicarbonate water and water, and then dried over anhydrous magnesium sulfate. The solvent was distilled off under reduced pressure to obtain a residue. The residue was purified by silica gel column chromatography (toluene/ethyl acetate=19/1, volume ratio) to obtain compound (T-2) (29.16 g, yield: 92.5%).

Third Step:

Under a nitrogen atmosphere, toluene (150 mL), 2-propanol (150 mL) and compound (T-2) (29.16 g, 78.70 mmol) were put in a reaction vessel and then mixed. In the resulting solution, 5% Pd on carbon (1.46 g) was added, and under a hydrogen atmosphere, the resulting mixture was stirred at room temperature until no hydrogen was absorbed any more. After reaction completion, the Pd on carbon was removed and the solvent was further distilled off. The residue was purified by silica gel column chromatography (toluene/ethyl acetate=19/1, volume ratio) to obtain compound (T-3) (26.80 g, yield: 91.4%).

Fourth Step:

Under a nitrogen atmosphere, toluene (260 mL), compound (T-3) (26.00 g, 69 mmol), an 88% formic acid aqueous solution (78 mL) and TBAB (4.45 g, 13.96 mmol) were put in a reaction vessel, and the resulting mixture was stirred at room temperature for 3 hours. The resulting reaction mixture was poured into water and subjected to extraction with toluene. The resulting extract was washed with saturated sodium bicarbonate water and water, and then dried over anhydrous magnesium sulfate. The solvent was distilled off under reduced pressure to obtain compound (T-4) (22.00 g, yield: 96.0%).

Fifth Step:

Under a nitrogen atmosphere, compound (T-4) (22.00 g, 66.97 mmol) and 1,2-dichloroethane (550 mL) were put in a reaction vessel, and the resulting mixture was cooled down to 0° C. Aluminum chloride (11.61 g, 87.07 mmol) was added thereto, and the resulting mixture was stirred for 1 hour while being maintained at 0° C. The resulting reaction mixture was poured into water and subjected to extraction with toluene. The resulting extract was washed with water, and then dried over anhydrous magnesium sulfate. The solvent was distilled off under reduced pressure to obtain a residue. The residue was purified by silica gel column chromatography (toluene/ethyl acetate=19/1, volume ratio), and further purified by recrystallization (heptane) to obtain compound (T-5) (17.95 g, yield: 81.6%).

Sixth Step:

Under a nitrogen atmosphere, dibromodifluoromethane (17.20 g, 81.97 mmol) and THF (35 mL) were put in a reaction vessel, and the resulting mixture was cooled down to 0° C. A THF (85 mL) solution of tris(diethylamino)phosphine (41.90 g, 169.40 mmol) was slowly added dropwise thereto. After the solution was added dropwise, the resulting mixture was stirred for 1 hour while being maintained at 0° C. Next, a THF (45 mL) solution of compound (T-5) (17.95 g, 54.64 mmol) was slowly added dropwise thereto. After the solution was added dropwise, the resulting mixture was returned to room temperature, and further stirred at room temperature for 12 hours. The resulting reaction mixture was poured into water, and subjected to extraction with ethyl acetate. The resulting extract was washed with water, and then dried over anhydrous magnesium sulfate. The solvent was distilled off under reduced pressure to obtain a residue. The residue was purified by silica gel column chromatography (heptane/toluene=9/1, volume ratio), and further purified by recrystallization (heptane) to obtain compound (T-6) (14.96 g, yield: 75.5%).

Seventh Step:

Under a nitrogen atmosphere, compound (T-6) (14.96 g, 41.27 mmol) and chloroform (150 mL) were put in a reaction vessel, and the resulting mixture was cooled down to −60° C. A chloroform (100 mL) solution of bromine (6.93 g, 43.33 mmol) was slowly added dropwise thereto. After the solution was added dropwise, the resulting mixture was stirred for 3 hours while being maintained at −60° C. The resulting reaction mixture was poured into a saturated aqueous solution of sodium thiosulfate, and the resulting aqueous layer was subjected to extraction with toluene. A combined organic layer was washed with a saturated aqueous solution of sodium thiosulfate and water, and dried over anhydrous magnesium sulfate. The solvent was distilled off under reduced pressure to obtain a residue. The residue was purified by silica gel column chromatography (heptane/toluene=9/1, volume ratio), and further purified by recrystallization (heptane) to obtain compound (T-7) (13.04 g, yield: 57.9%).

Eighth Step:

Under a nitrogen atmosphere, 3,4,5-trifluorophenol (3.70 g, 24.97 mmol), potassium carbonate (7.25 g, 52.43 mmol), TBAB (2.41 g, 7.49 mmol) and DMF (100 mL) were put in a reaction vessel, and the resulting mixture was heated at 70° C. for 1 hour while the resulting mixture was stirred. ADMF (30 mL) solution of compound (T-7) (13.04 g, 24.97 mmol) was slowly added dropwise thereto. After the solution was added dropwise, the resulting mixture was stirred for 10 hours while being maintained at 70° C. The resulting reaction mixture was poured into water and subjected to extraction with toluene. Organic layers combined were washed with water, and dried over anhydrous magnesium sulfate. The solvent was distilled off under reduced pressure to obtain a residue. The residue was purified by silica gel column chromatography (heptane/toluene=9/1, volume ratio), and further purified by recrystallization (heptane) to obtain compound (T-8) (3.30 g, yield: 26.0%).

Ninth Step:

Compound (T-8) (3.30 g, 6.49 mmol), 5% Pd/C (0.19 g), 2-propanol (17 mL) and toluene (17 mL) were put in an autoclave, and the resulting mixture was heated at 40° C. under a hydrogen pressure, and then stirred for 7 days. The 5% Pd/C was removed, the filtrate was concentrated, and the residue was purified by silica gel column chromatography (heptane/toluene=4/1, volume ratio), and further purified by recrystallization (heptane) to obtain compound (No. 10) (1.63 g, yield: 48.6%).

$^1$H-NMR (CDCl$_3$; δ ppm): 7.10 (dd, 2H), 6.85-6.82 (m, 4H), 3.93 (t, 2H), 2.40 (tt, 1H), 2.45-2.24 (m, 9H), 1.75 (quin, 2H), 1.48 (sep, 2H), 1.42-1.31 (m, 4H), 1.13-1.02 (m, 6H), 0.97 (t, 3H).

Transition temperature: C, 82.2; S$_B$ 121.7; N, 226.6; I.

Maximum temperature (T$_{NI}$)=168.7° C.; dielectric anisotropy (Δ∈)=14.1; optical anisotropy (Δn)=0.127; viscosity (η)=63 mPa·s.

Synthesis Example 2

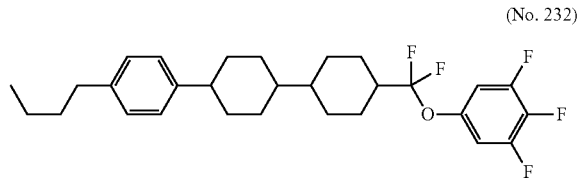 [SMILES: CCCCc1ccc(C2CCC(C3CCC(C(F)(F)Oc4cc(F)c(F)c(F)c4)CC3)CC2)cc1]
(No. 232)

Compound (No. 232) was prepared according to a method in Synthesis Example 1.

$^1$H-NMR (CDCl$_3$; δ ppm): 7.11 (dd, 2H), 6.85-6.82 (m, 4H), 2.57 (t, 2H), 2.43 (tt, 1H), 2.05-1.84 (m, 9H), 1.58 (quin, 2H), 1.47-1.32 (m, 6H), 1.13-1.02 (m, 6H), 0.92 (t, 3H).

Transition temperature: C, 63.1; S$_B$ 93.2; N, 192.2; I.

Maximum temperature (T$_{NI}$)=139.7° C.; dielectric anisotropy (Δ∈)=13.5; optical anisotropy (Δn)=0.104; viscosity (η)=59 mPa·s.

Synthesis Example 3

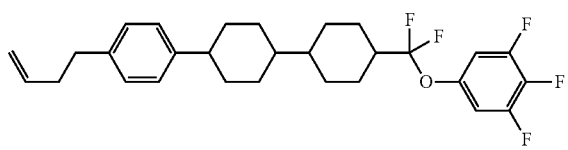 [SMILES: CCCCc1ccc(C2CCC(C3CCC(C(F)(F)Oc4cc(F)c(F)c(F)c4)CC3)CC2)cc1]
(No. 15)

Compound (No. 15) was prepared according to the method in Synthesis Example 1.

$^1$H-NMR (CDCl$_3$; δ ppm): 7.12 (s, 4H), 6.86-6.83 (dd, 2H), 5.87 (tq, 1H), 5.05 (dd, 1H), 4.98 (dd, 1H), 2.67 (t, 2H), 2.43 (tt, 1H), 2.37 (dq, 2H), 2.05-1.84 (m, 9H), 1.45-1.34 (m, 4H), 1.17-1.05 (m, 6H).

Transition temperature: C, 68.1; N, 216.0; I.

Maximum temperature (T$_{NI}$)=155.7° C.; dielectric anisotropy (Δ∈)=14.6; optical anisotropy (Δn)=0.124; viscosity (η)=50 mPa·s.

Comparative Example 1

For comparison with compound (No. 232), compound (A) and compound (B) were selected. In compound (No. 348) described in Patent literature No. 1, compound (A) includes a compound in which a substituent is butyl. The reason of selecting compound (A) is that compound (A) has the same number of phenylene rings and cyclohexylene rings as compound (No. 232) in the invention has. Three samples was examined by storing the samples for 30 days in a freezer at −20° C. according to "(3) Compatibility at low temperature" described above. Results described above were summarized in Table 1. In compound (No. 232), no crystal (or no smectic phase) precipitated at a ratio of 20%/80%. On the other hand, in compound (A) and compound (B), crystals precipitated. When a proportion of the compound (A) was decreased, no crystal precipitated at a ratio of 5%/95%. Moreover, when a proportion of the compound (B) was decreased, no crystal precipitated at the ratio of 5%/95%. Accordingly, compound (No. 232) has been found to have a superior compatibility in comparison with compound (A) and compound (B).

TABLE 1
Comparison of compatibility at −20° C.
| Compound | Structure formula | Compatibility Compound/Base liquid crystal (B) |
|---|---|---|
| Compound (No. 232) | | 20%/80% |
| Compound (A) | | 5%/95% |
| Compound (B) | | 5%/95% |
Compound (1) was prepared according to the synthesis methods and the Synthesis Examples described above. Specific examples of compound (1) include compounds (No. 1) to (No. 240) shown below.
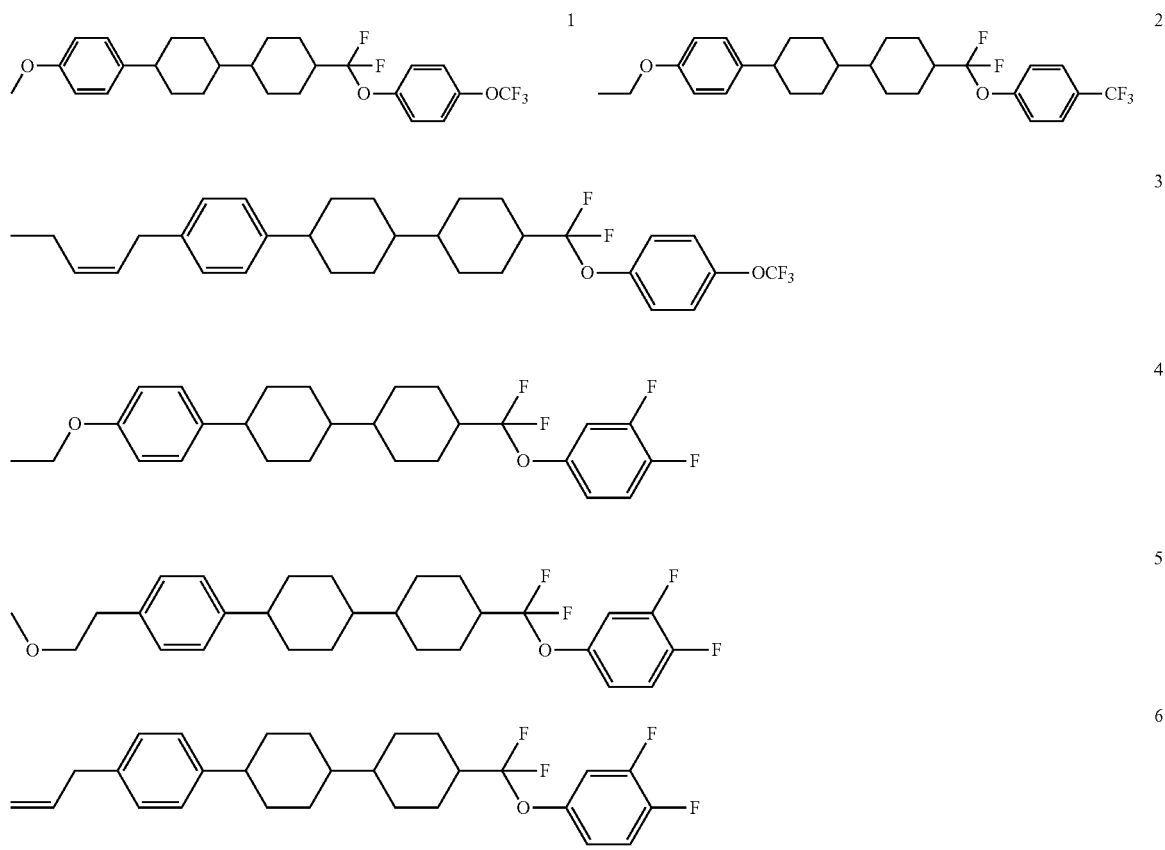

7
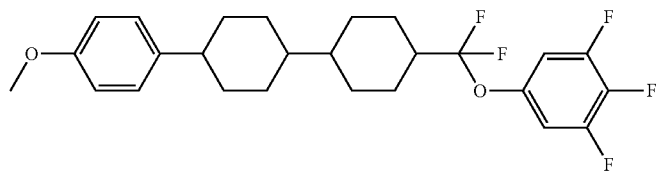
8
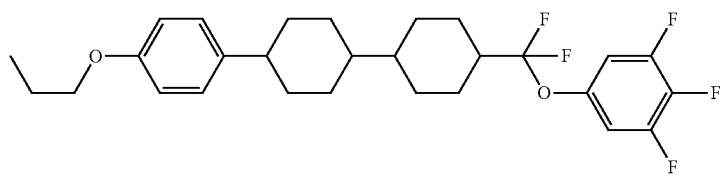
9
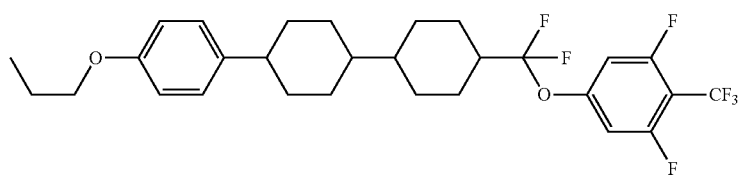
10
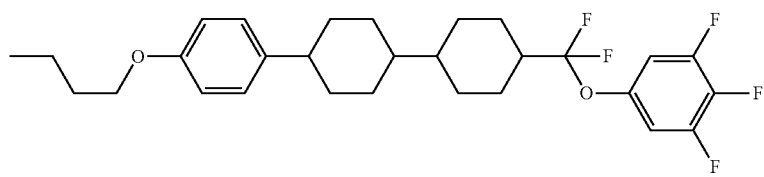
C 82.2 SB 121.7 N 226.6 I NI = 168.7°;
Δε = 14.1; Δn = 0.127; η = 63 mPa/s.
11
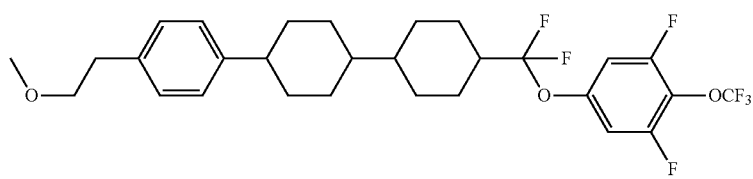
12
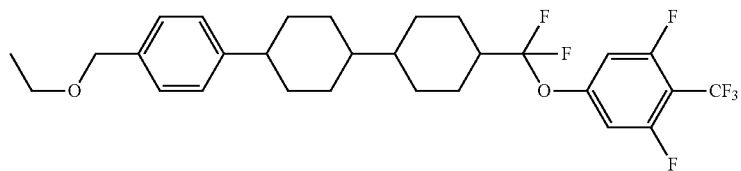
13
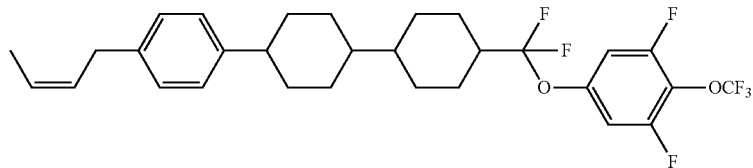
14
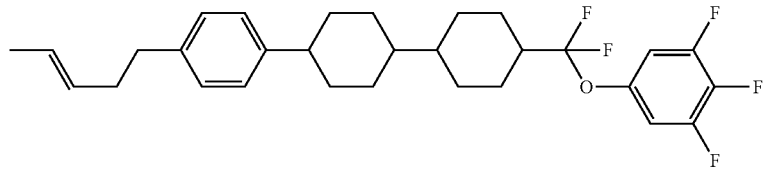

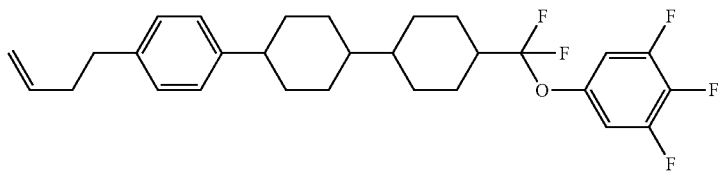
C 68.1 N 216.0 I NI = 155.7 ;
Δε = 14.6; Δn = 0.124; η = 50 mPa/s.
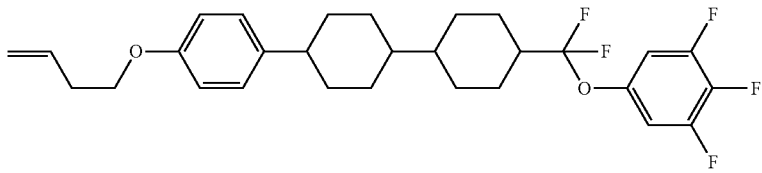
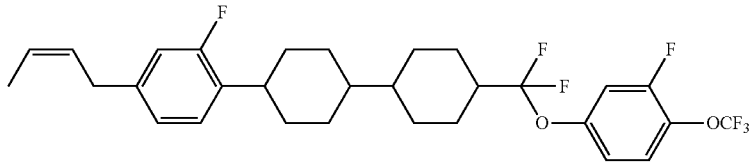
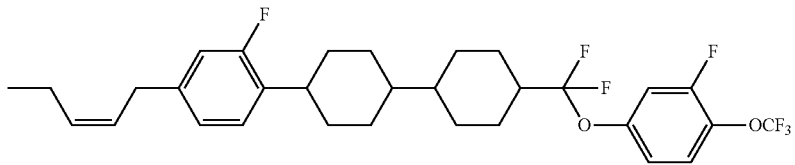
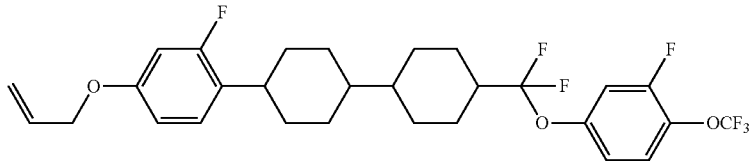
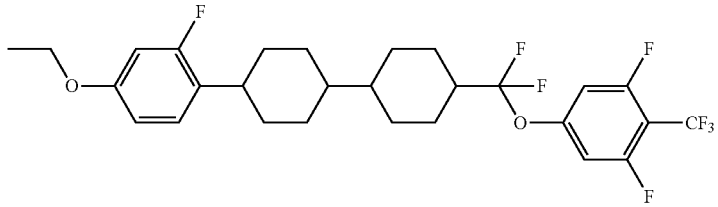
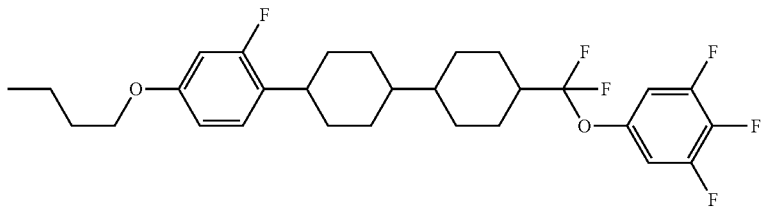
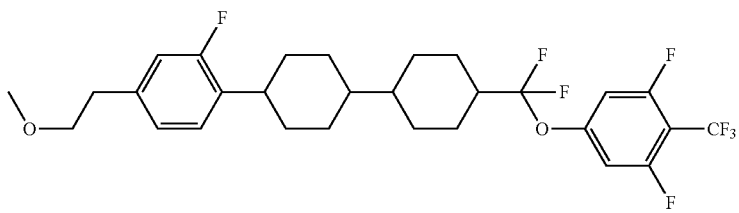

-continued
23
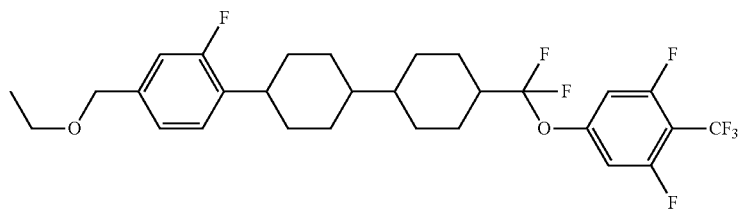
24
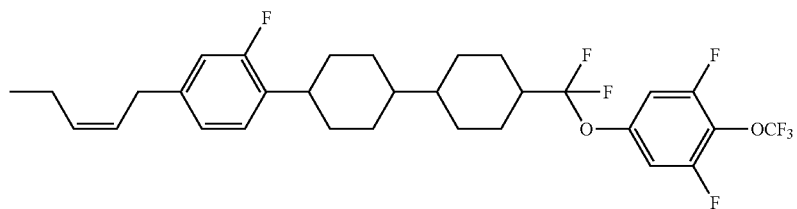
25 26
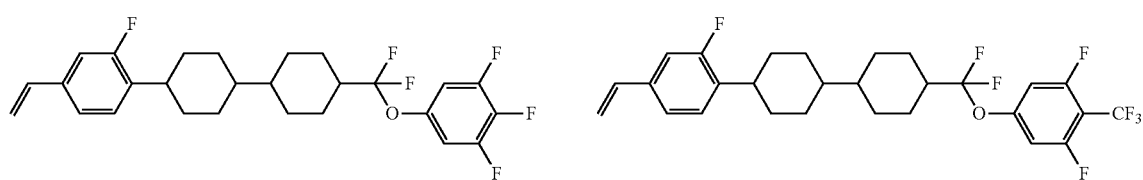
27
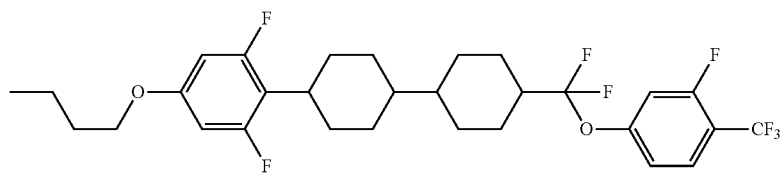
28
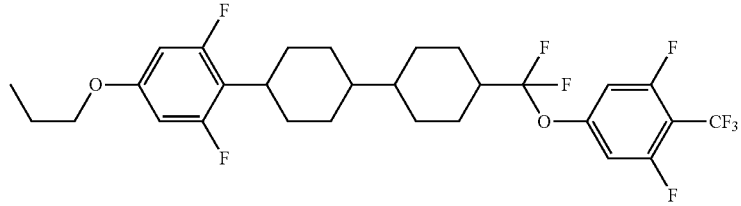
29
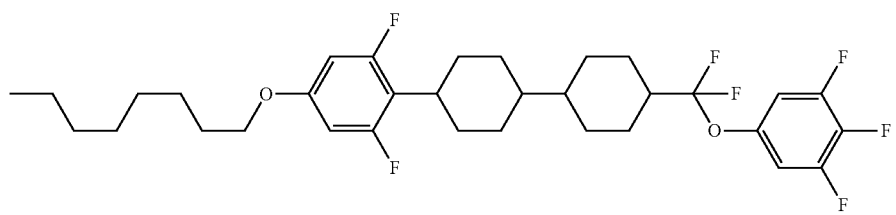
30 31
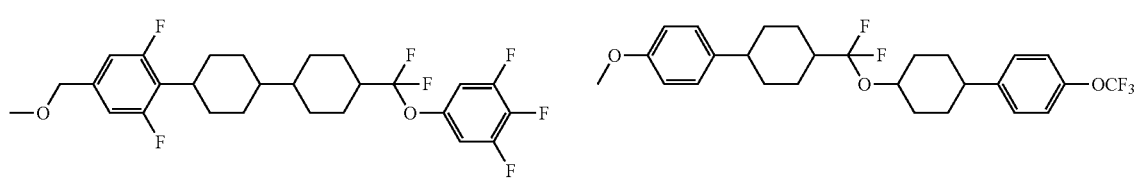
32
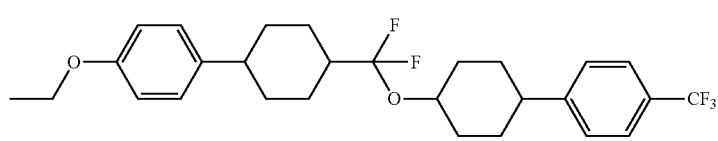

-continued
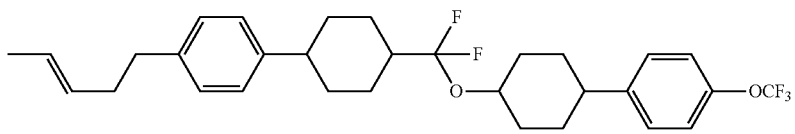
33
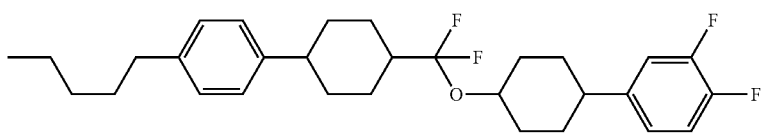
34
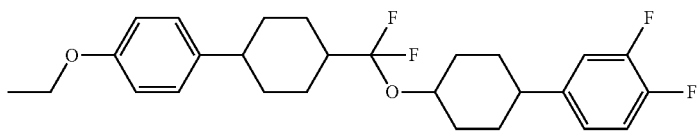
35
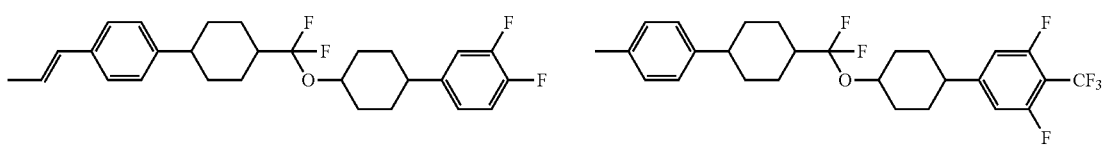
36  37
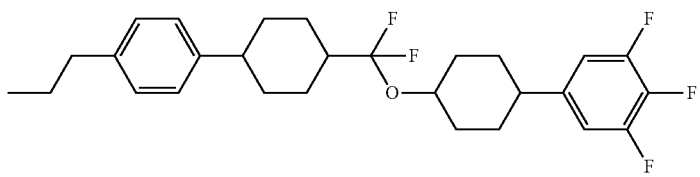
38
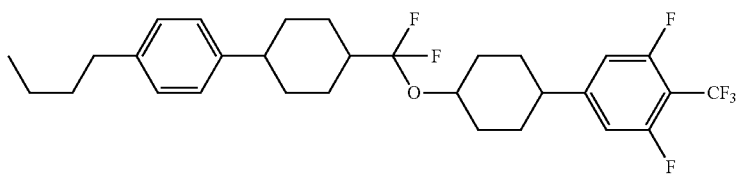
39
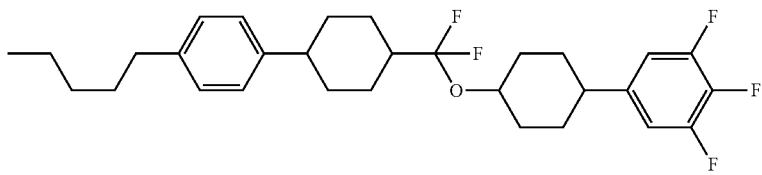
40
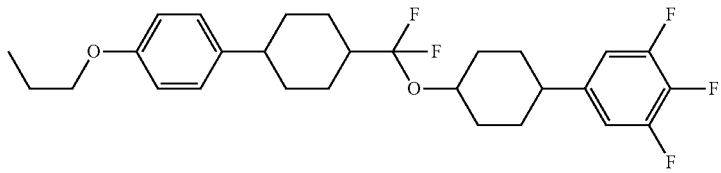
41
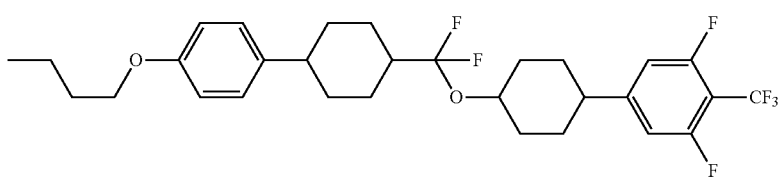
42

-continued
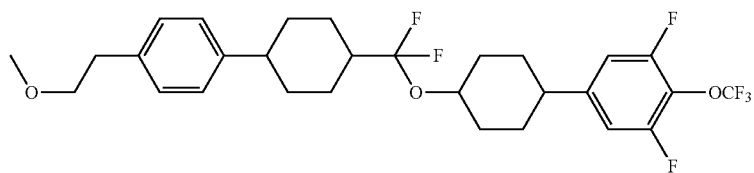
43
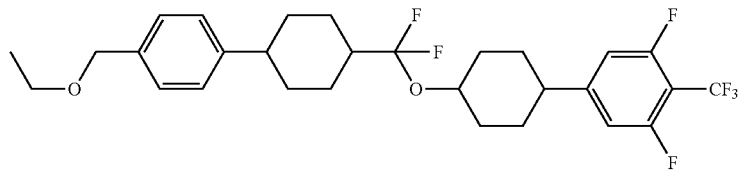
44
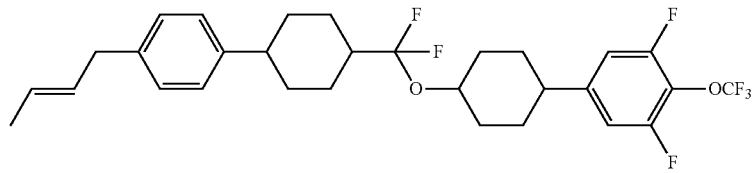
45
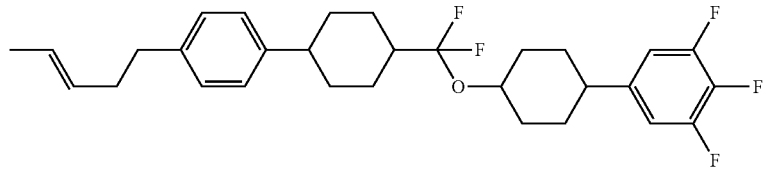
46
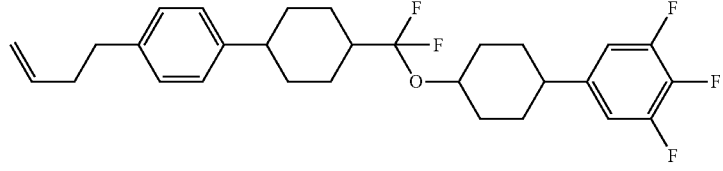
47
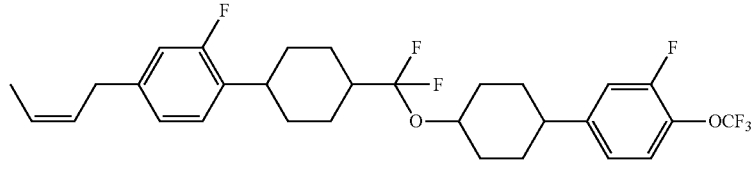
48
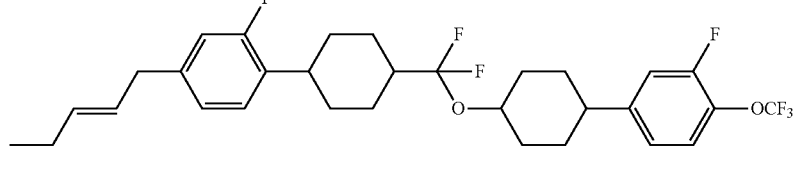
49
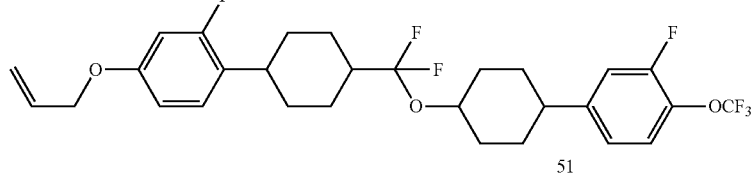
50
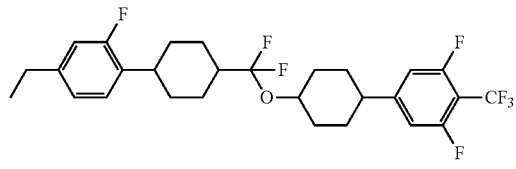
51
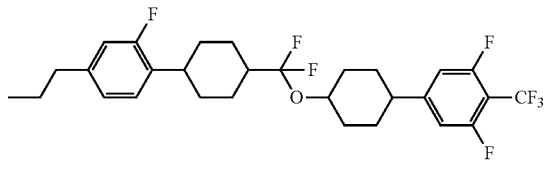
52

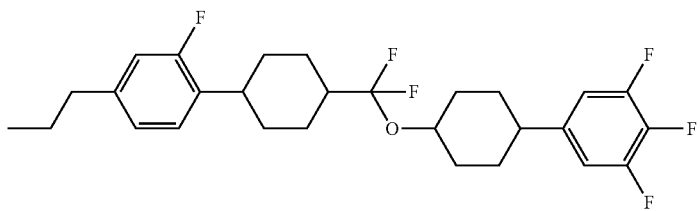
53
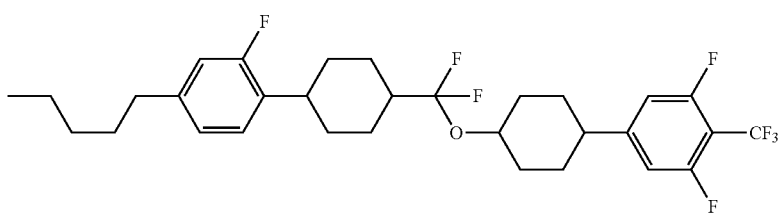
54
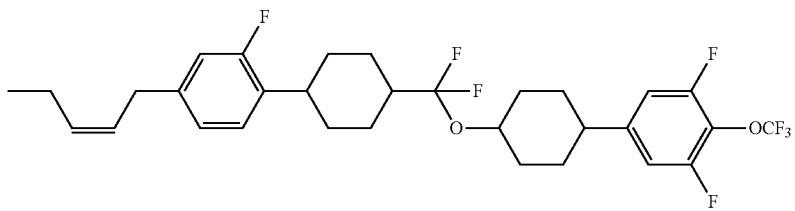
55
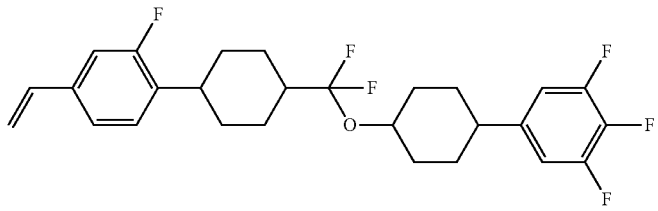
56
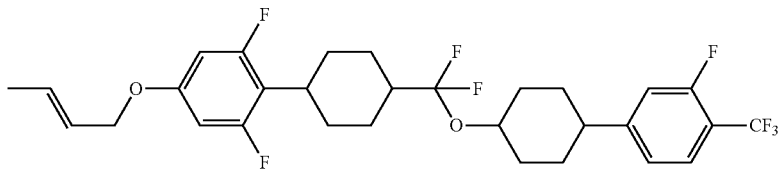
57
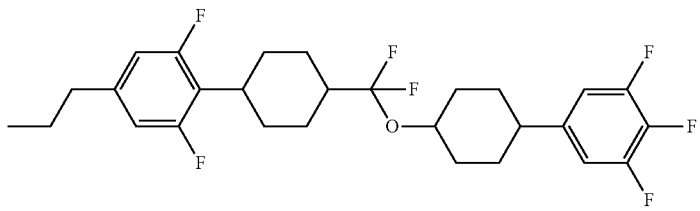
58
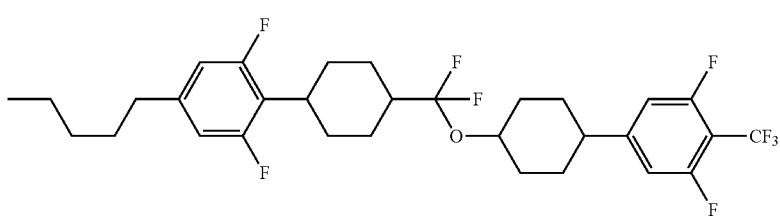
59

60
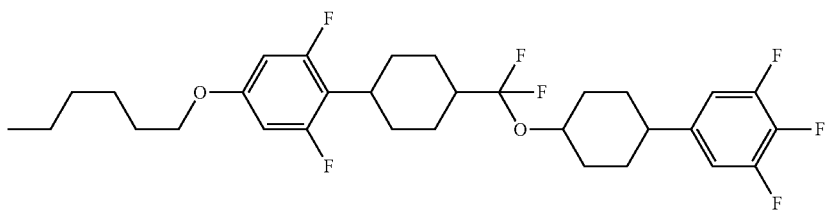
61
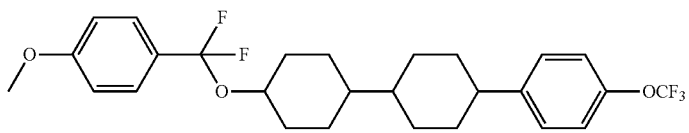
62
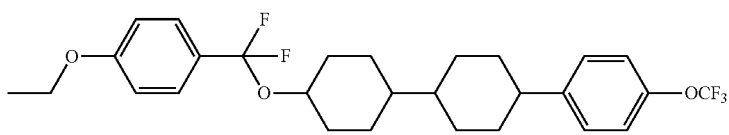
63
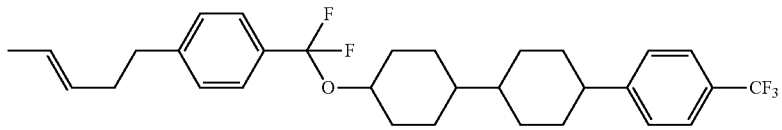
64
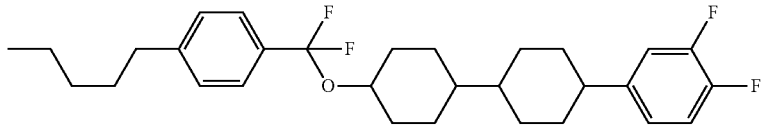
65
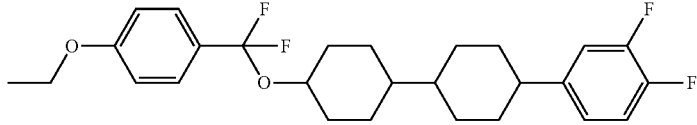
66
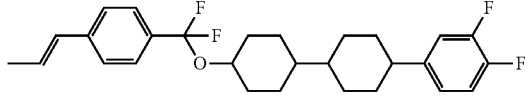
67
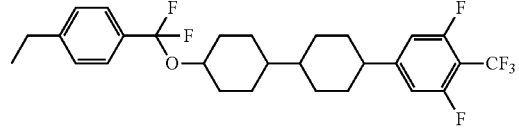
68
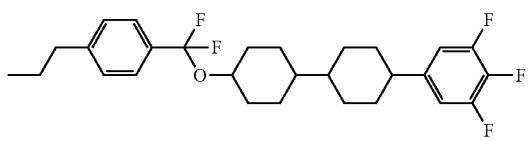
69
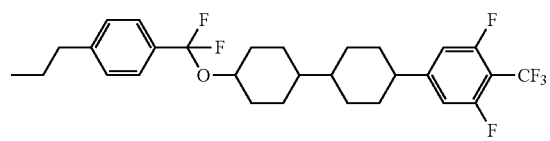
70
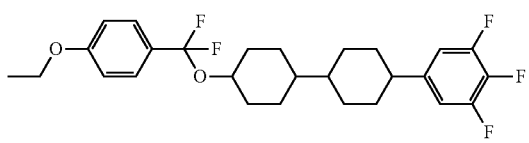
71
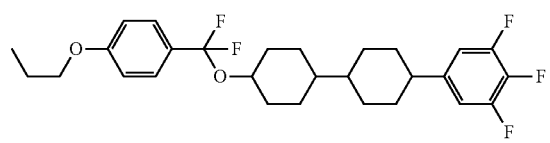
72
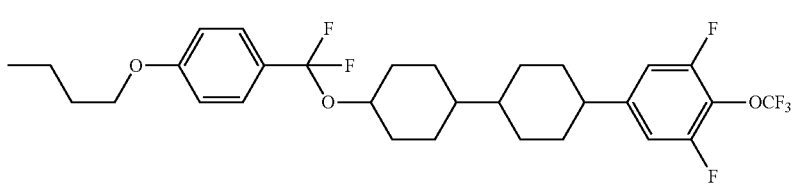

-continued
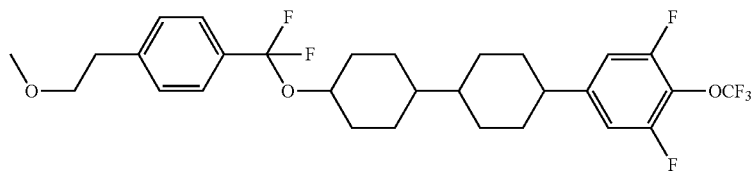
73
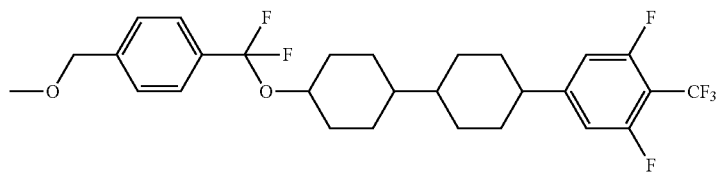
74
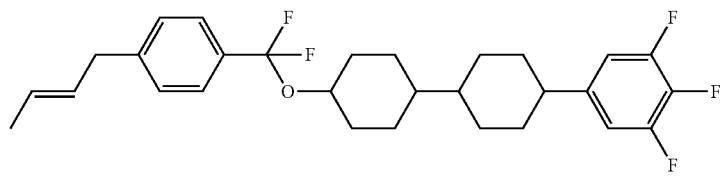
75
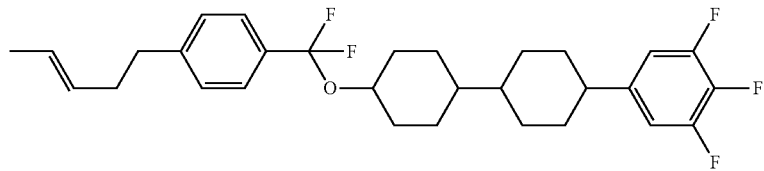
76
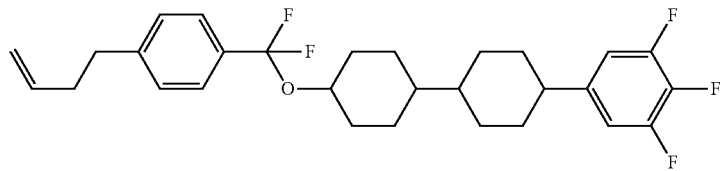
77
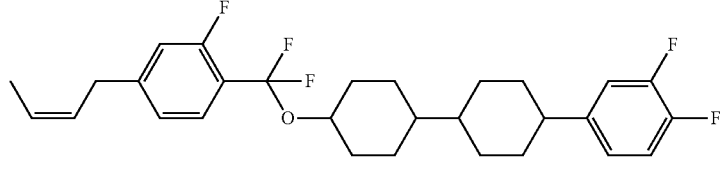
78
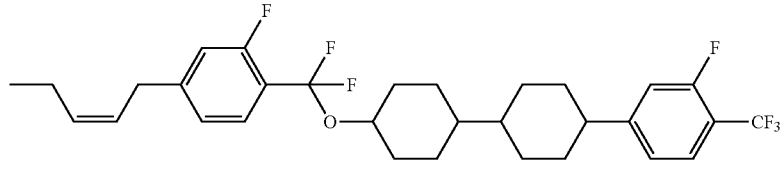
79
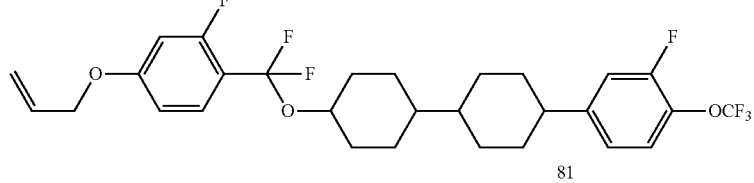
80
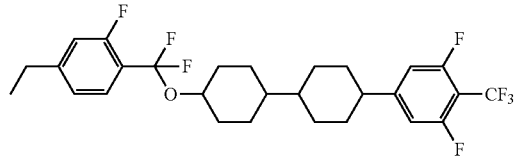
81
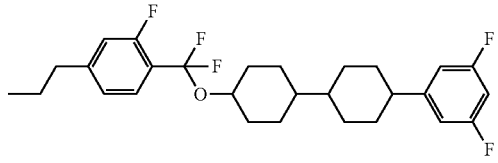
82

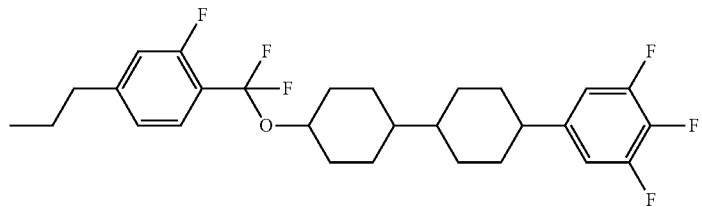
83
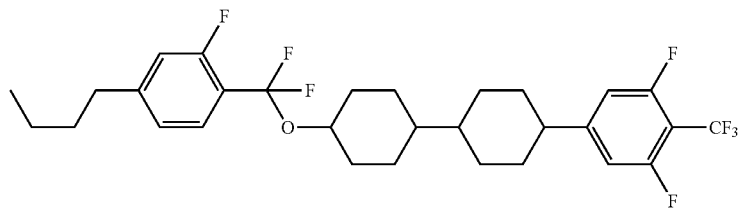
84
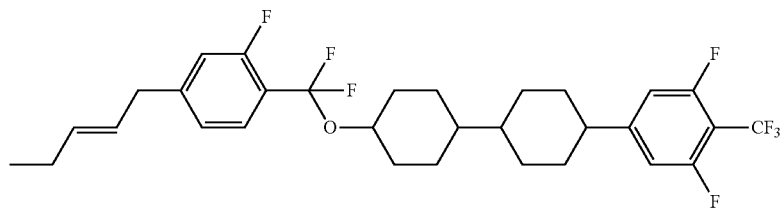
85
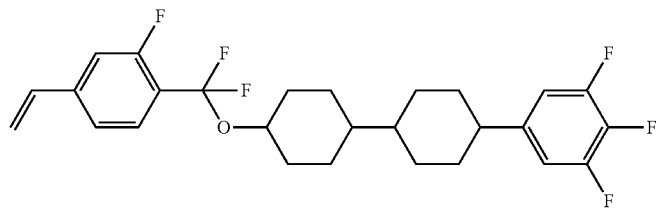
86
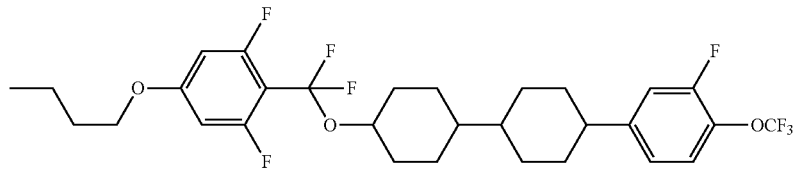
87
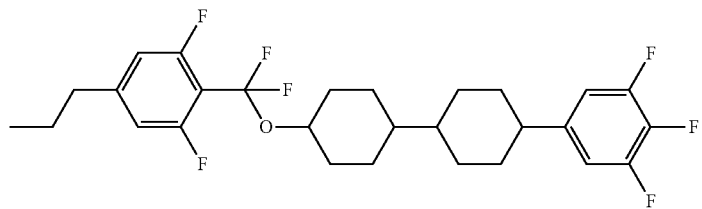
88
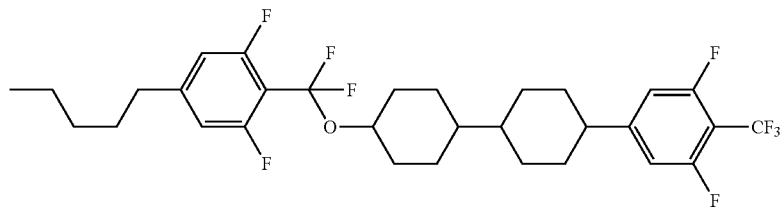
89

-continued
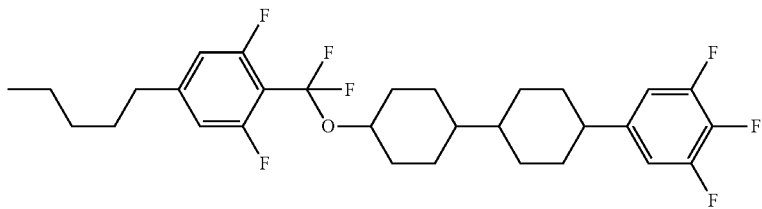
90
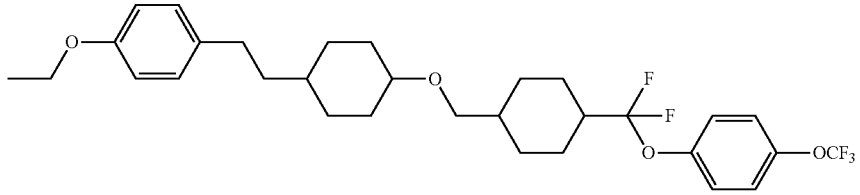
91
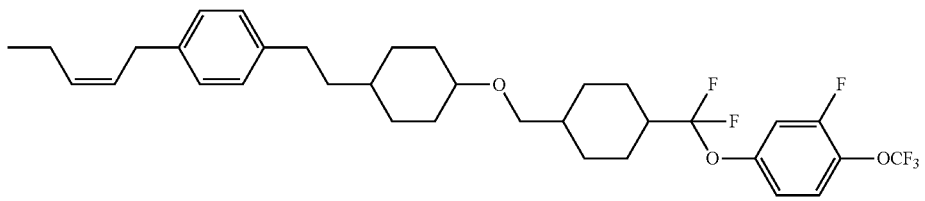
92
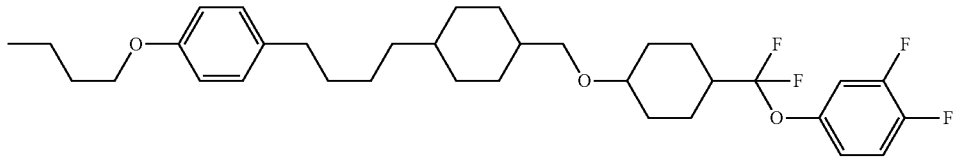
93
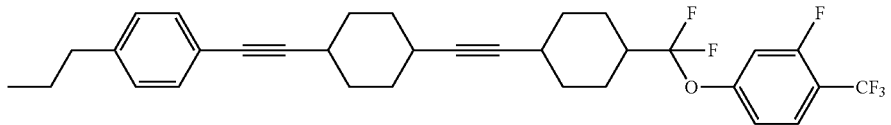
94
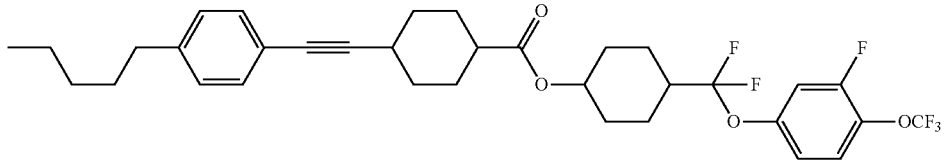
95
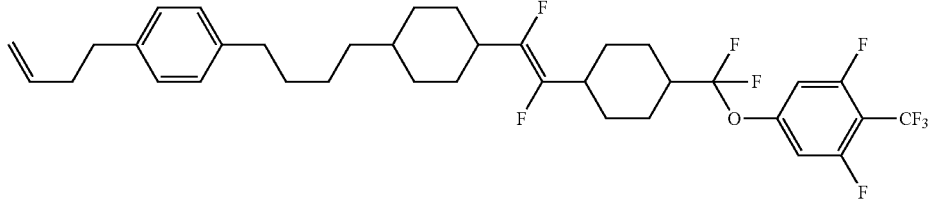
96
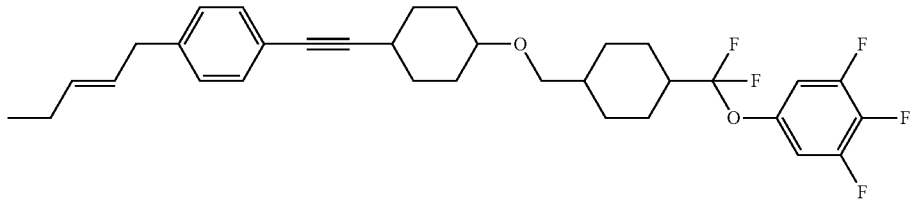
97

-continued
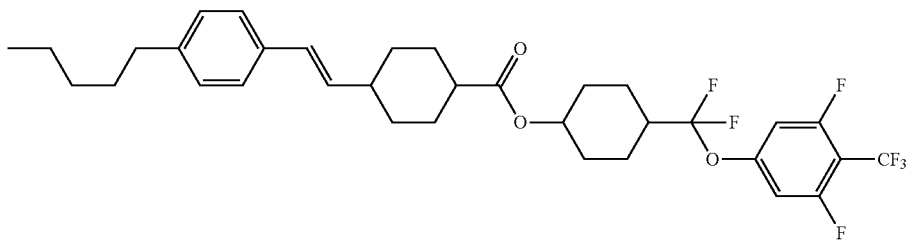
98
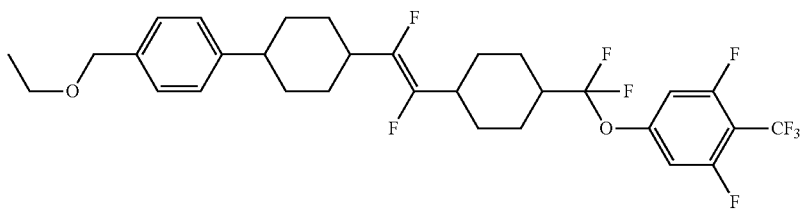
99
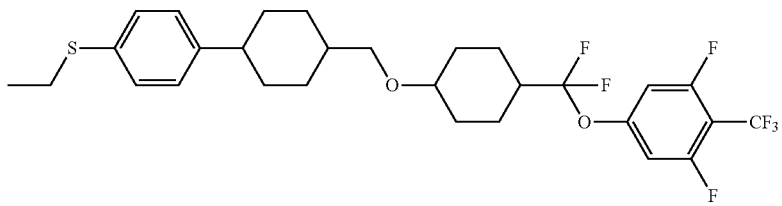
100
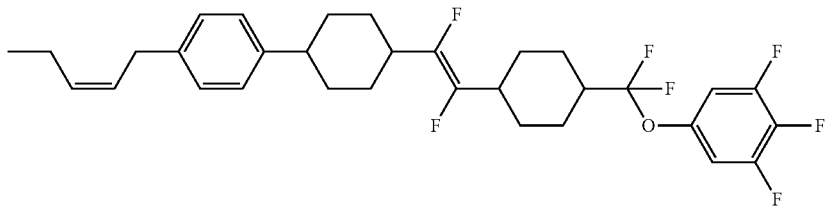
101
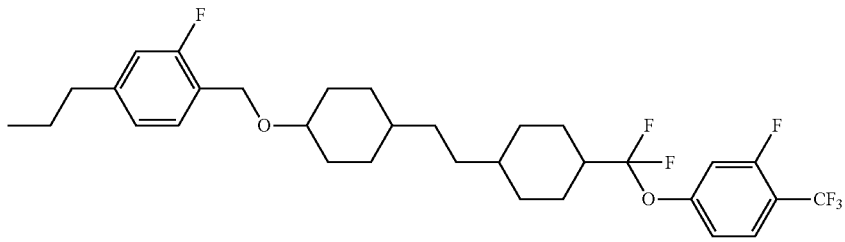
102
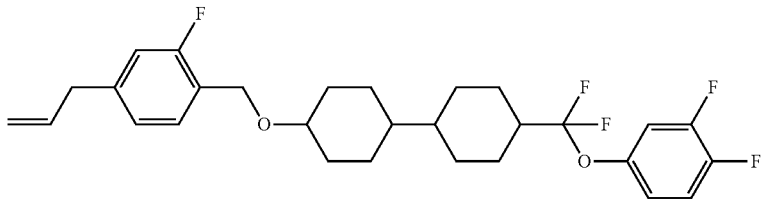
103
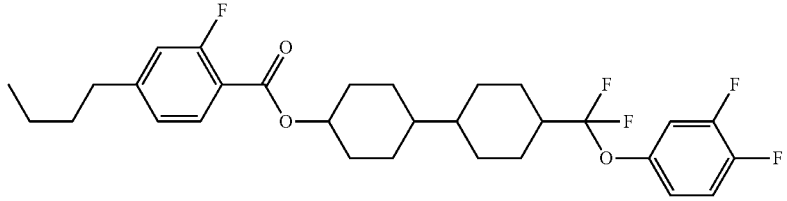
104

-continued
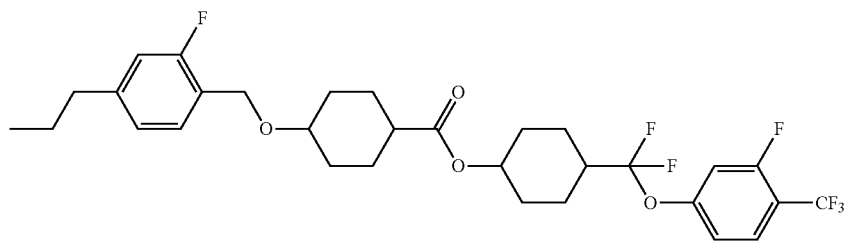
105
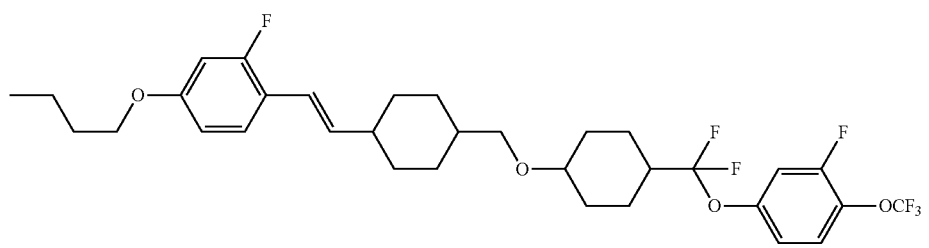
106
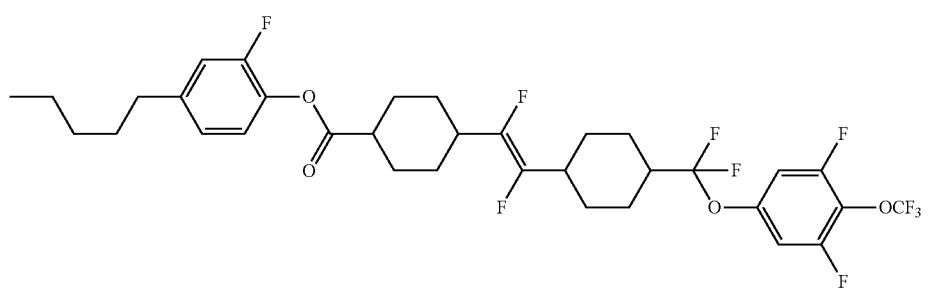
107
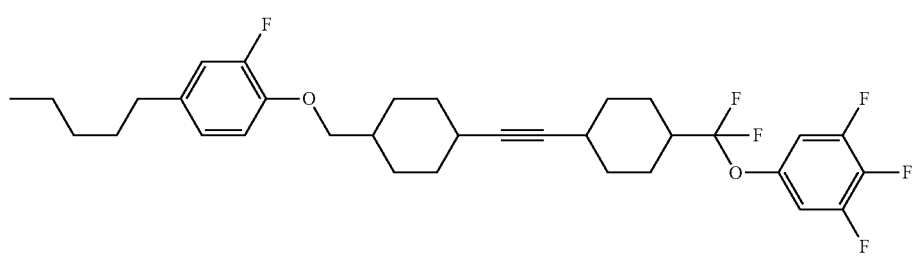
108
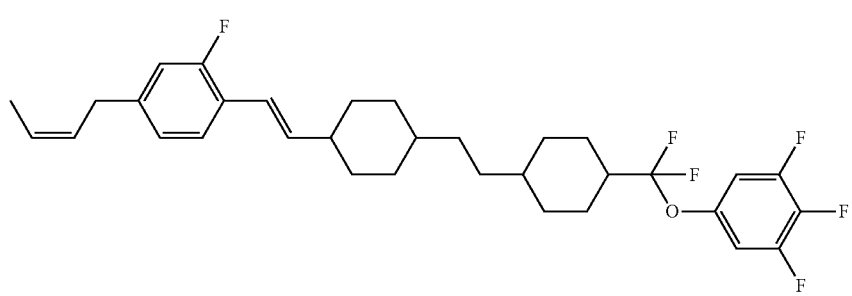
109
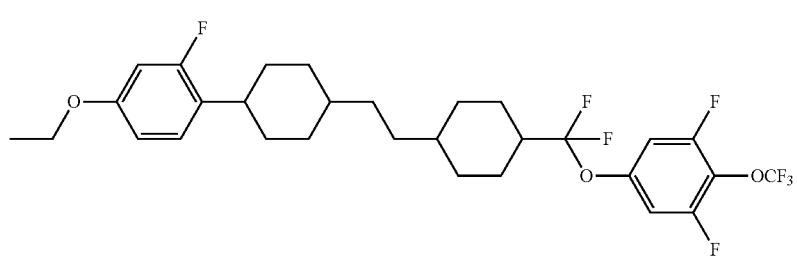
110

-continued
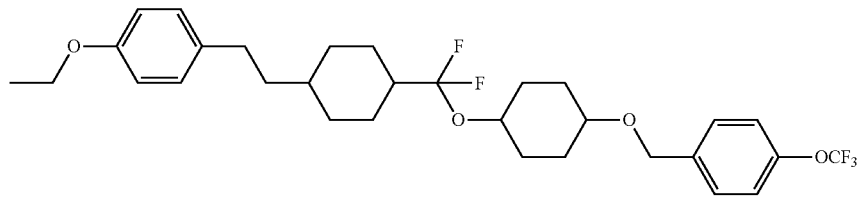
111
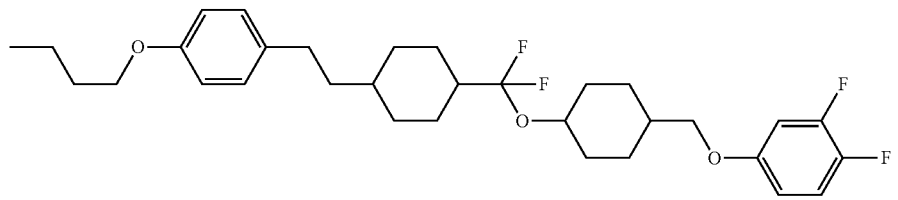
112
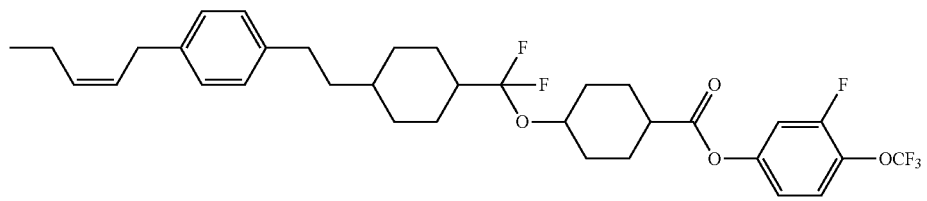
113
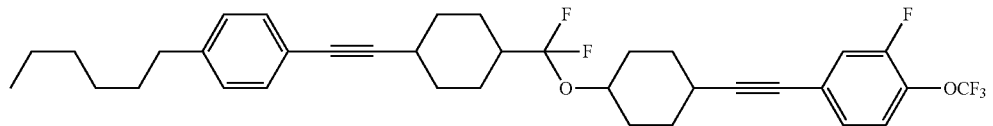
114
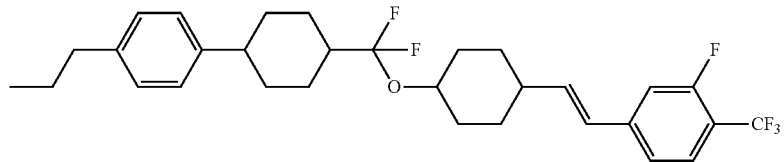
115
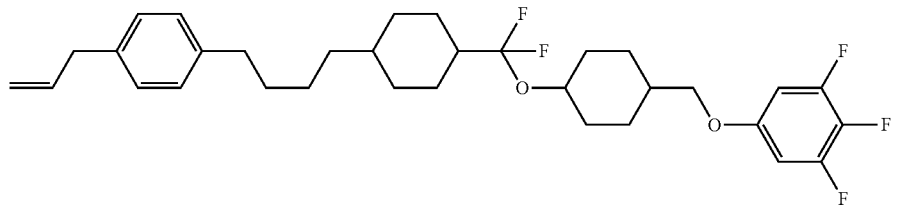
116
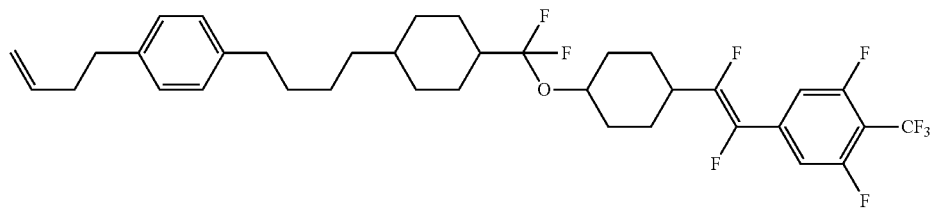
117
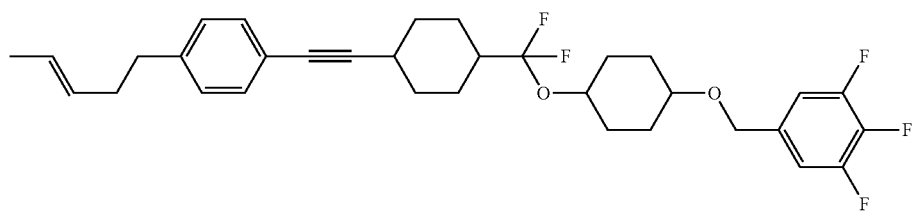
118

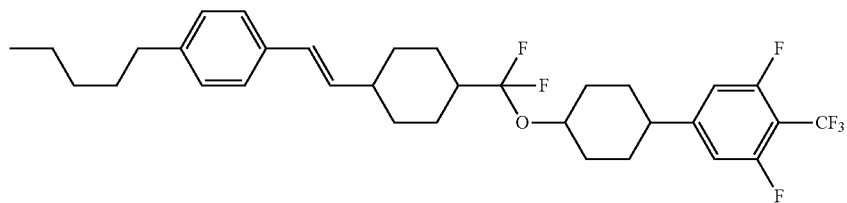
119
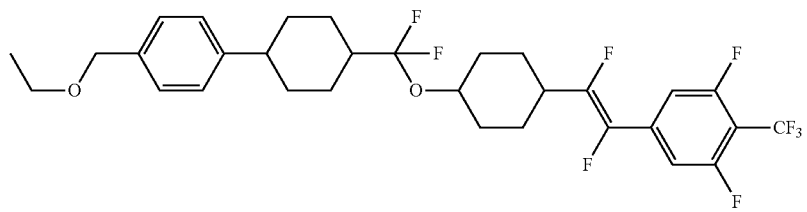
120
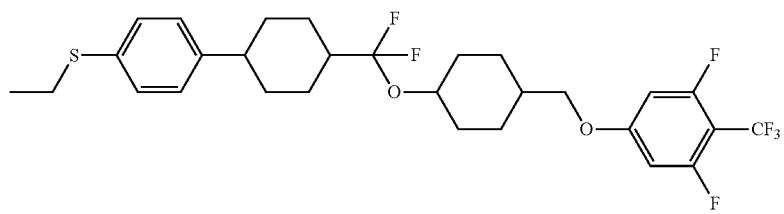
121
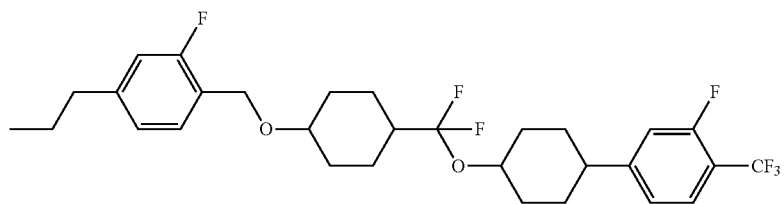
122
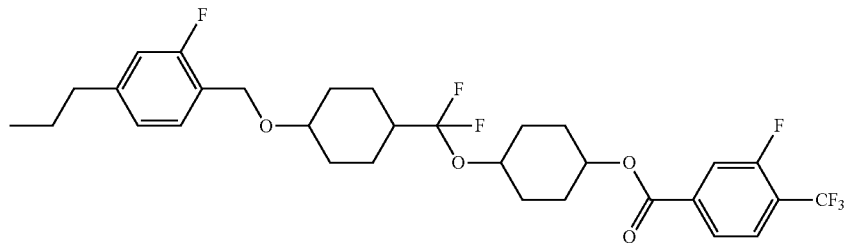
123
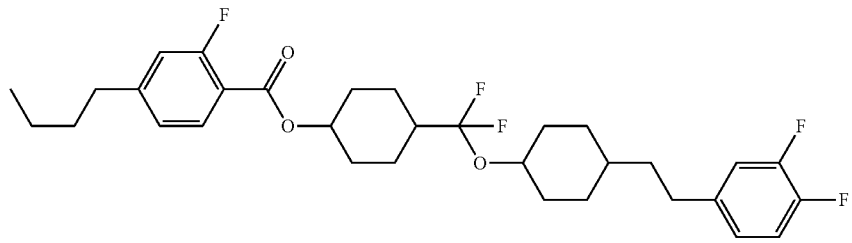
124
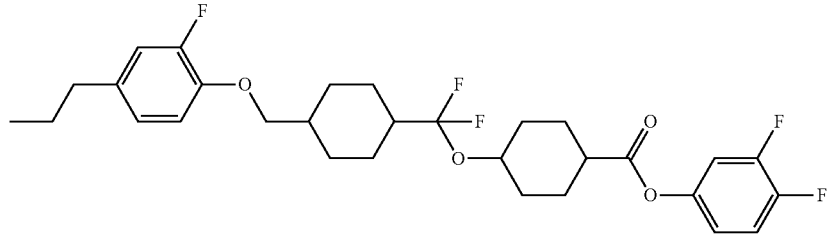
125

-continued
126
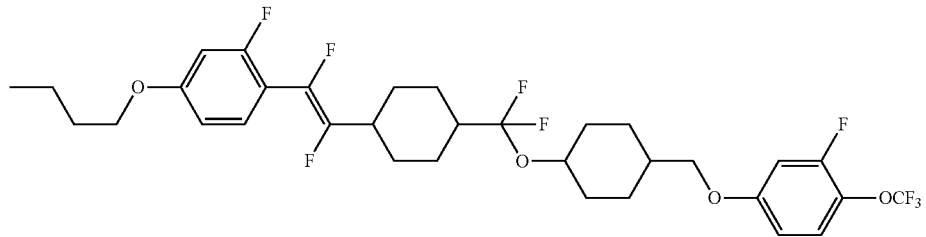
127
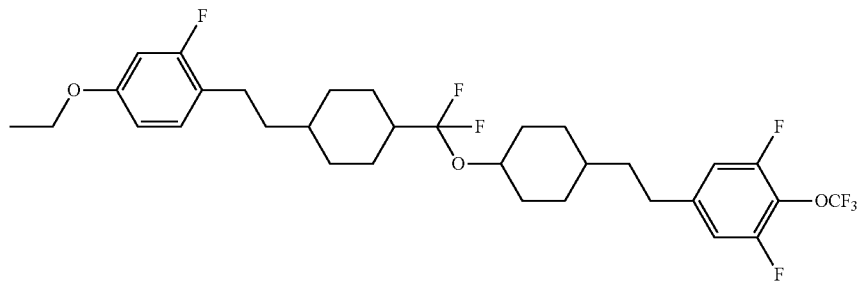
128
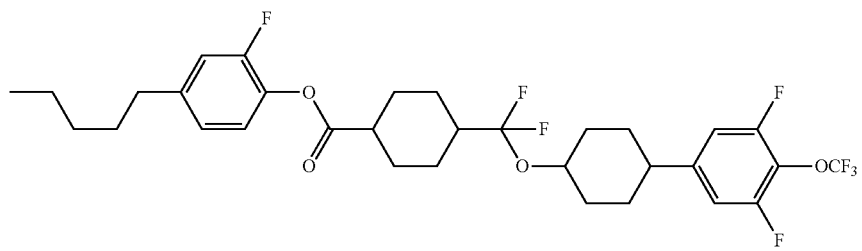
129
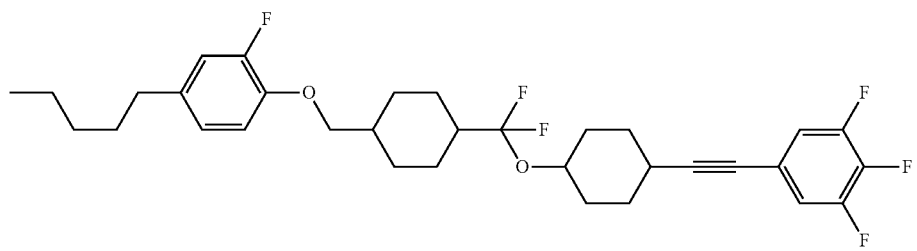
130
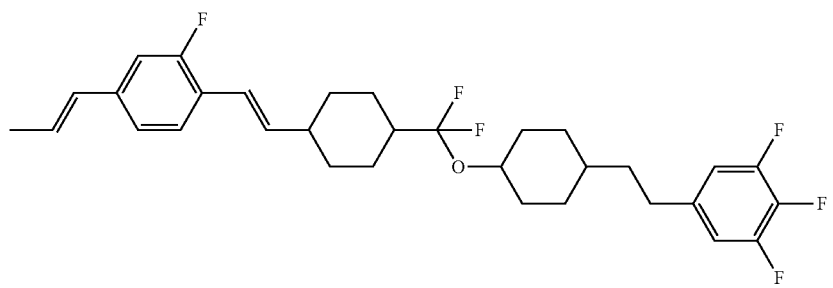
131
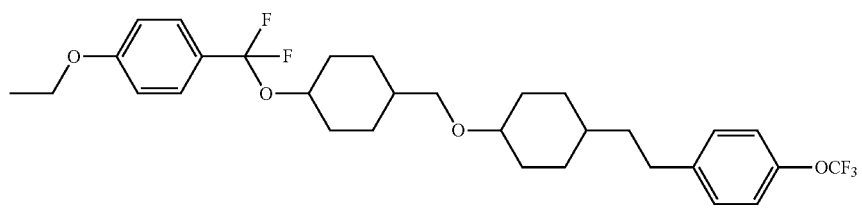

132
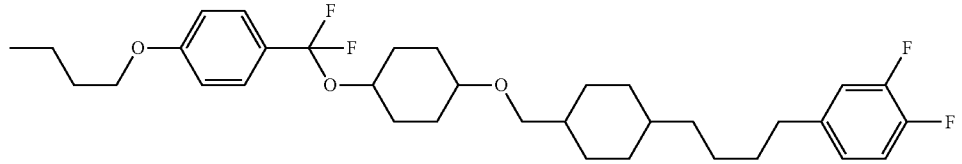
133
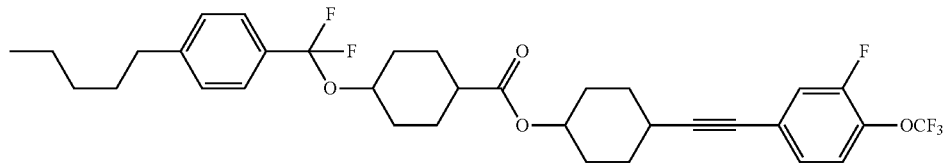
134
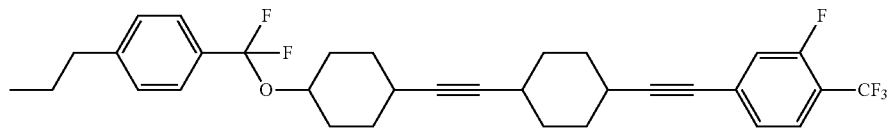
135
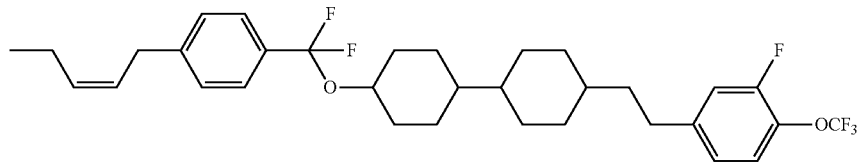
136
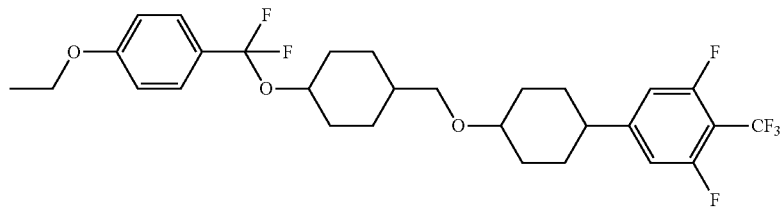
137
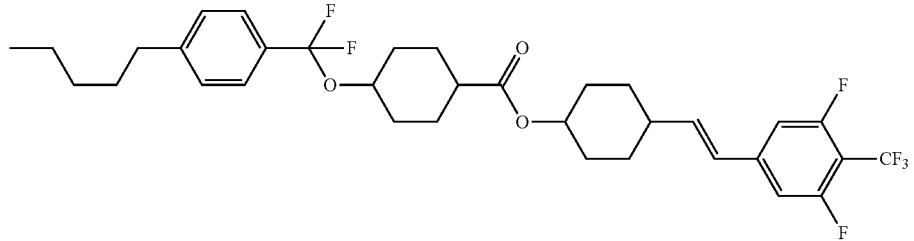
138
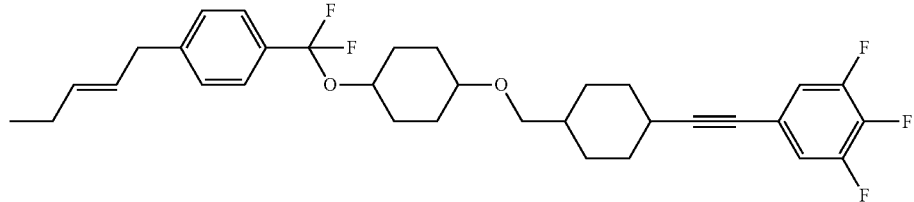
139
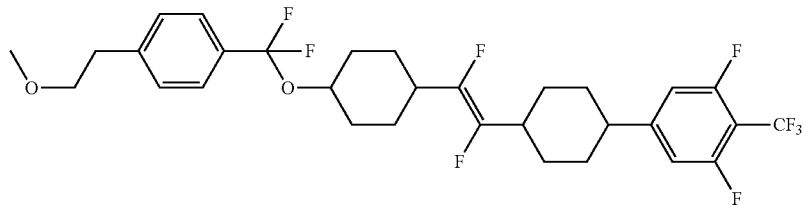

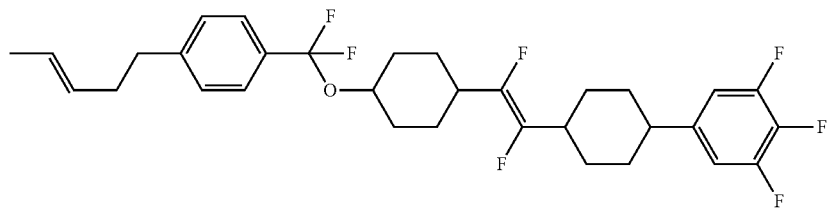 140
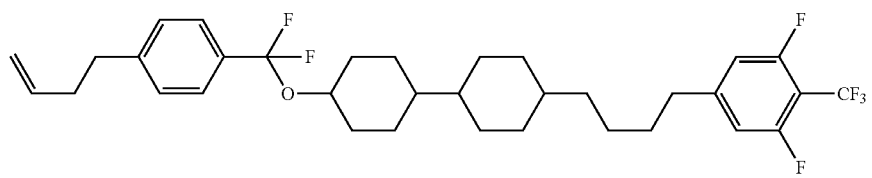 141
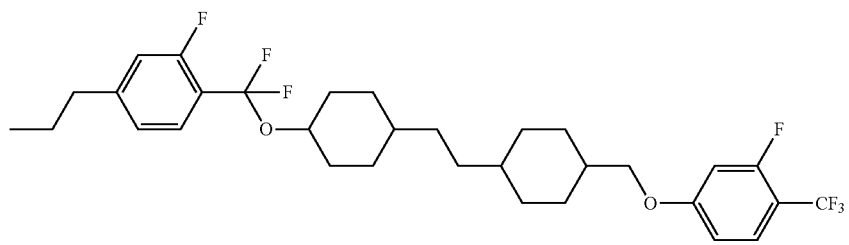 142
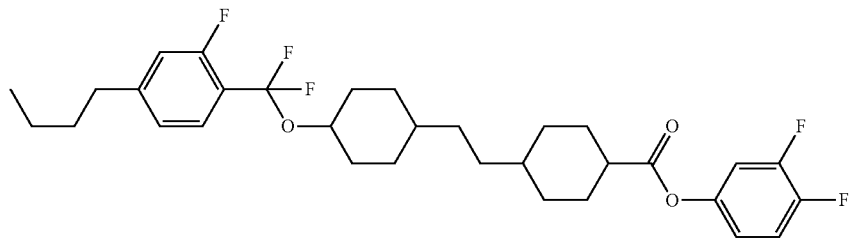 143
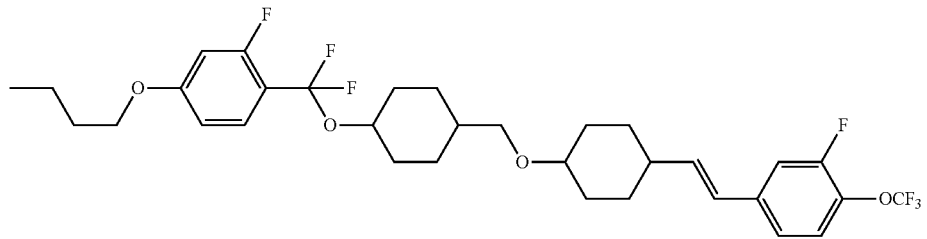 144
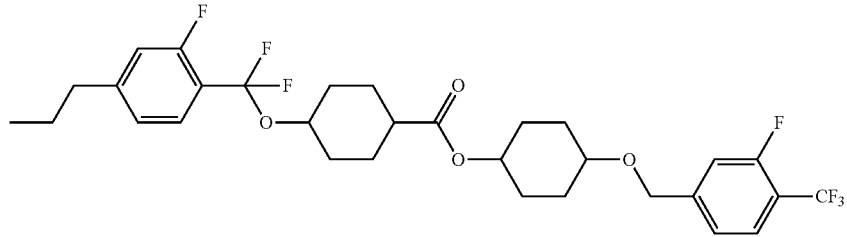 145
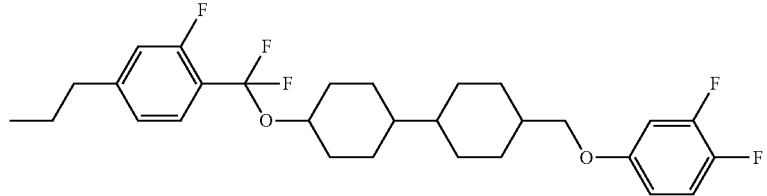 146

147
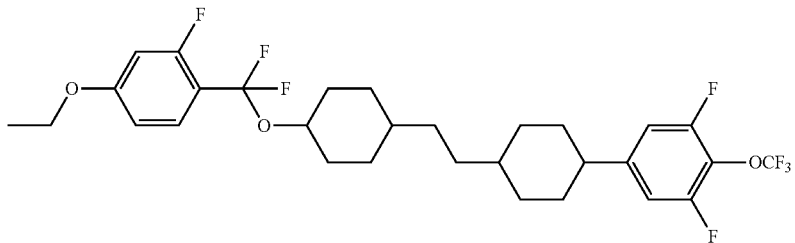
148
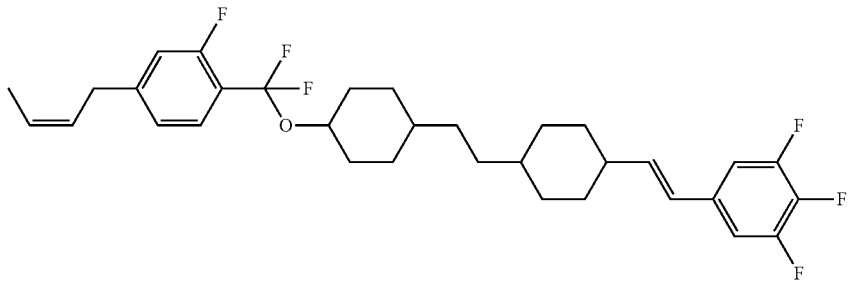
149
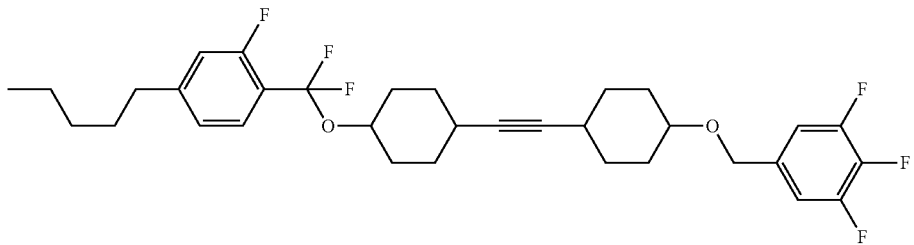
150
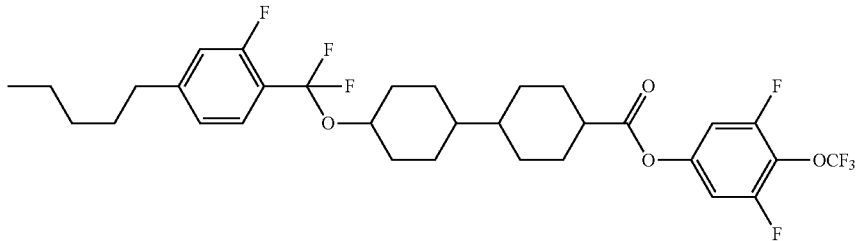
151
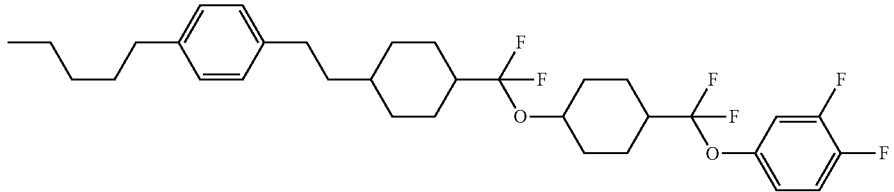
152
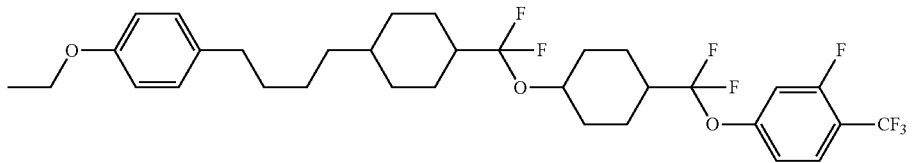
153
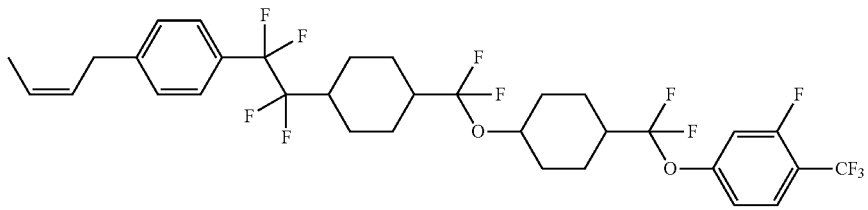

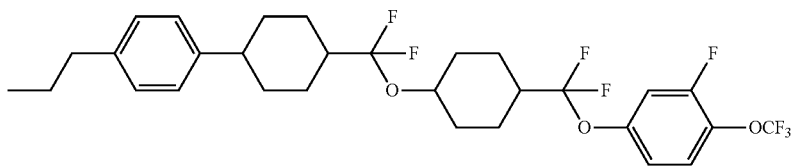
154
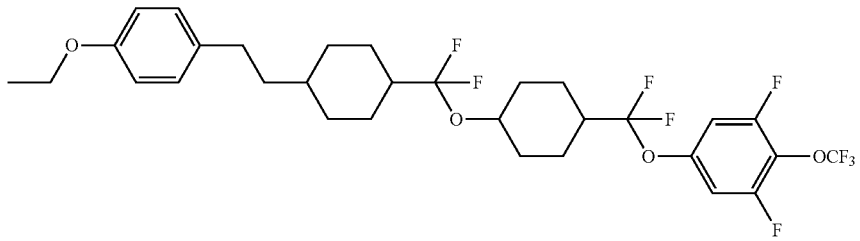
155
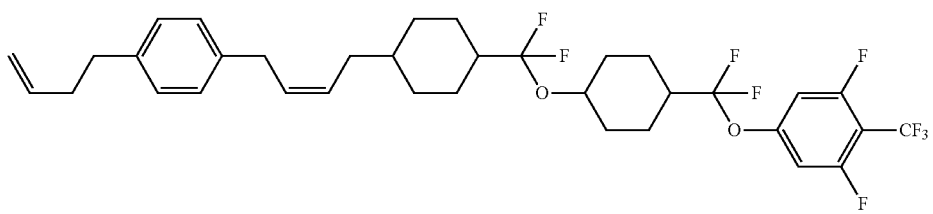
156
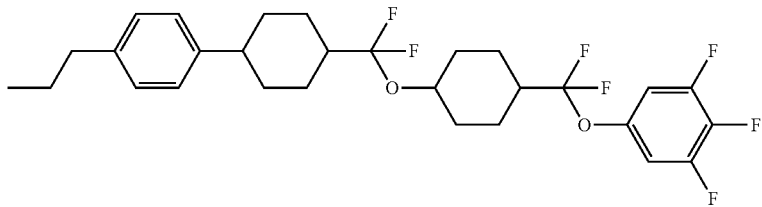
157
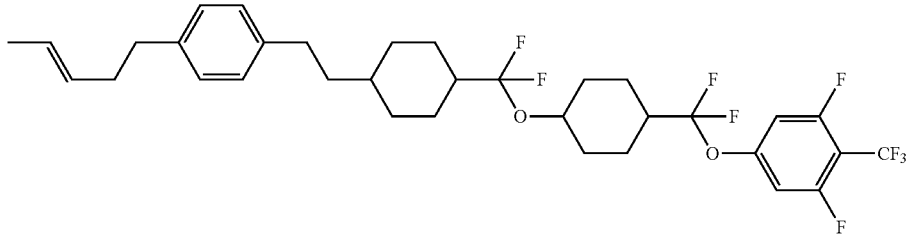
158
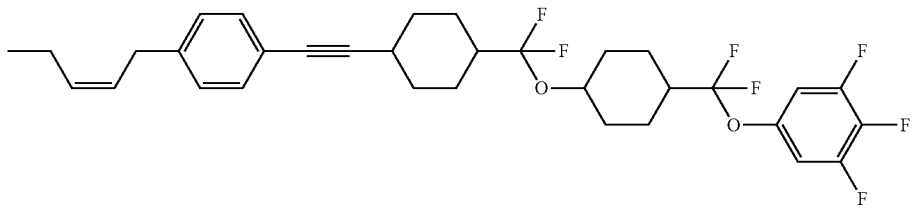
159
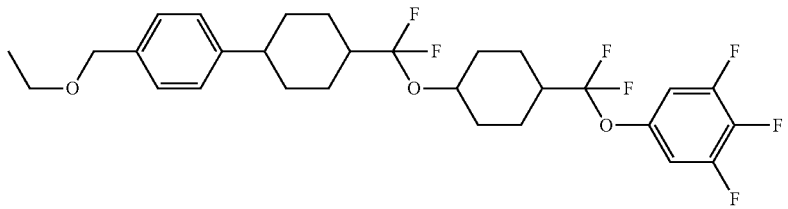
160

-continued
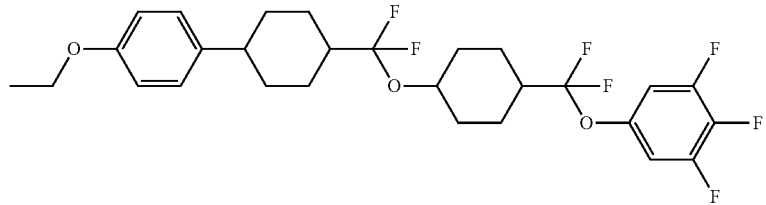
161
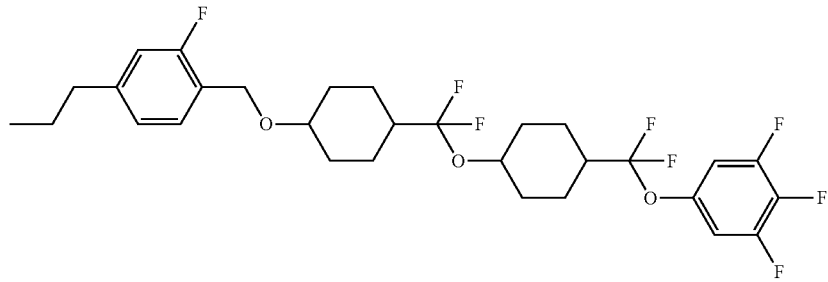
162
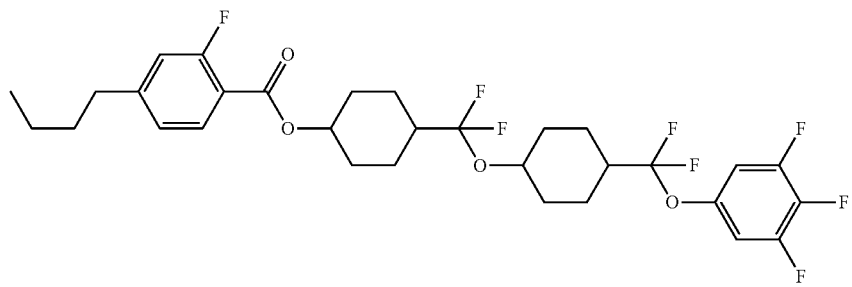
163
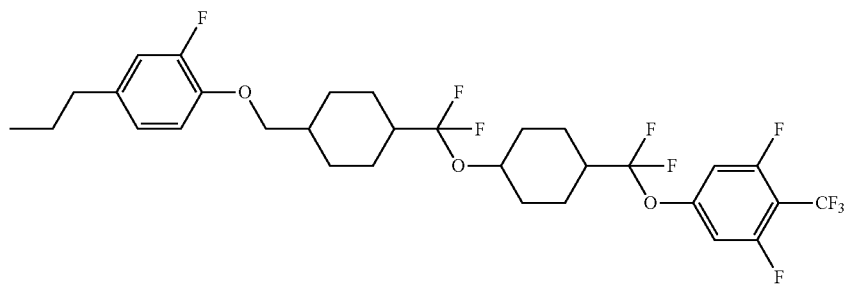
164
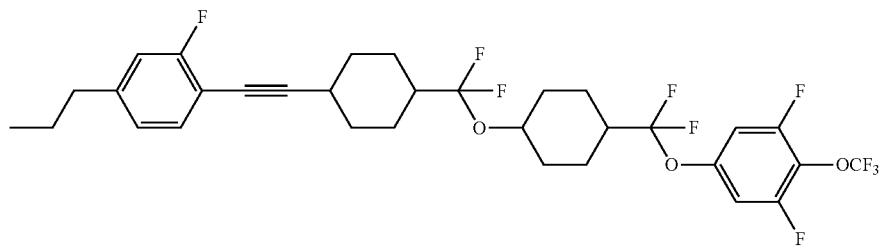
165
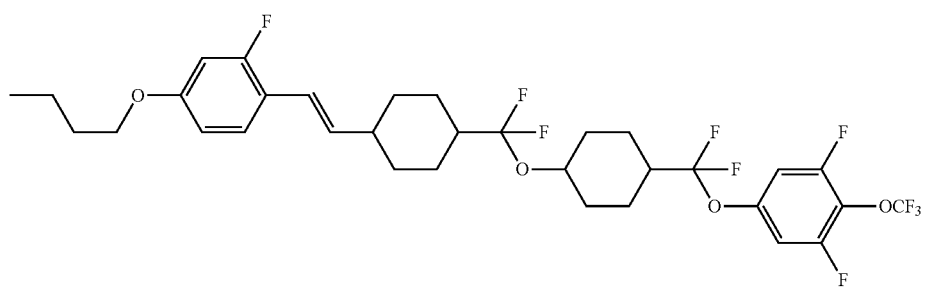
166

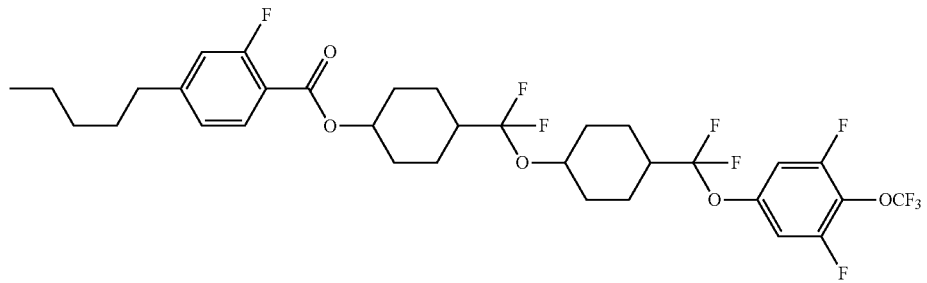 167
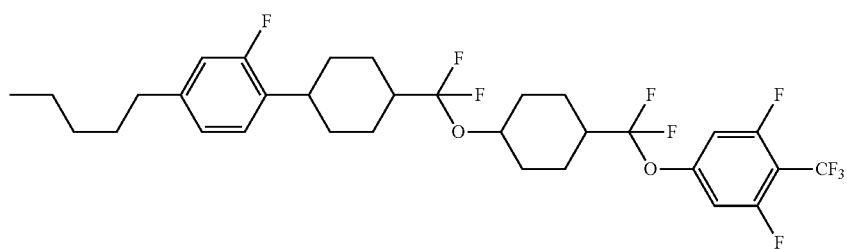 168
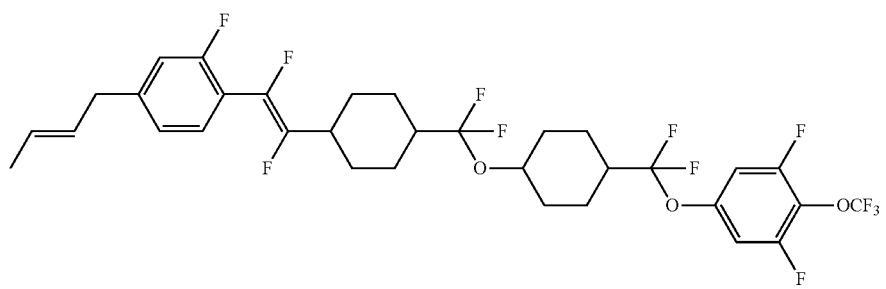 169
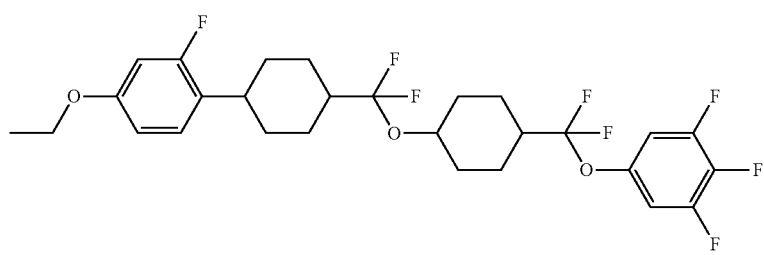 170
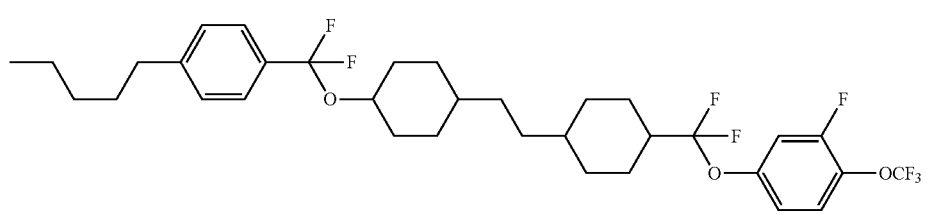 171
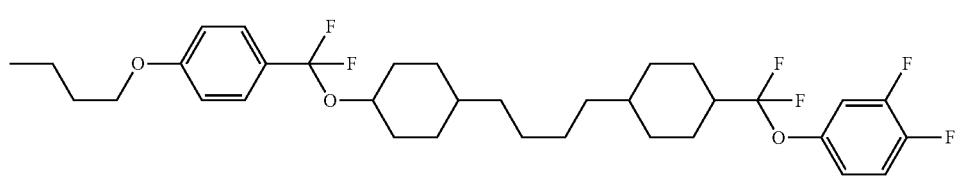 172

173
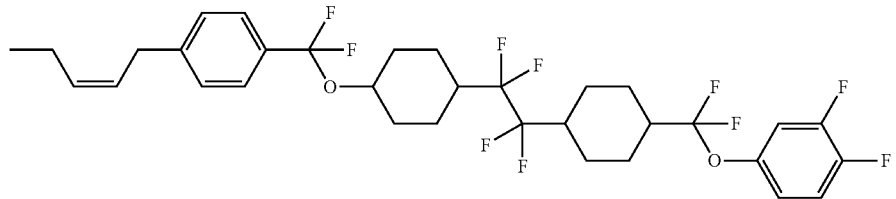
174
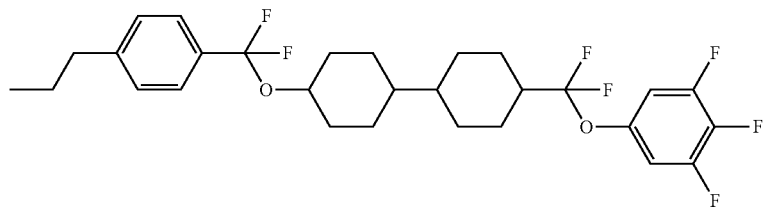
175
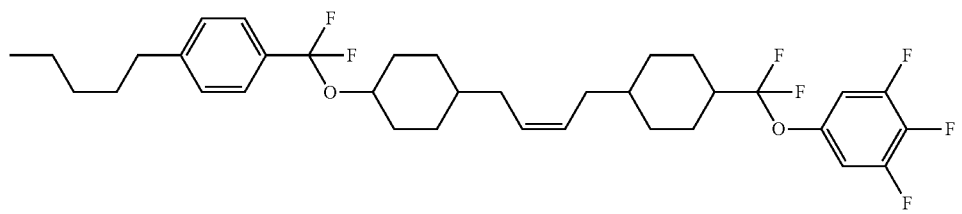
176
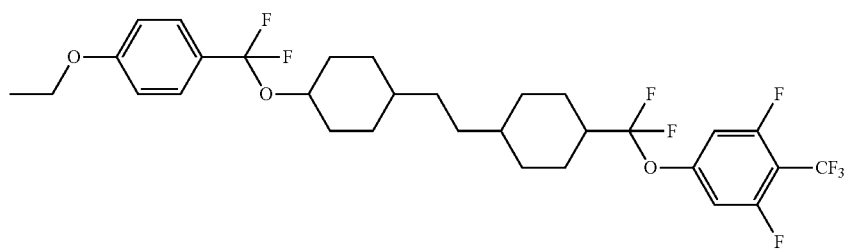
177
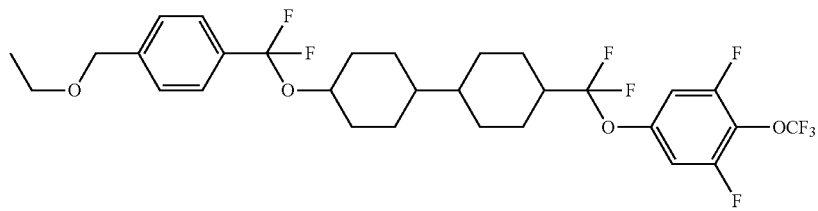
178
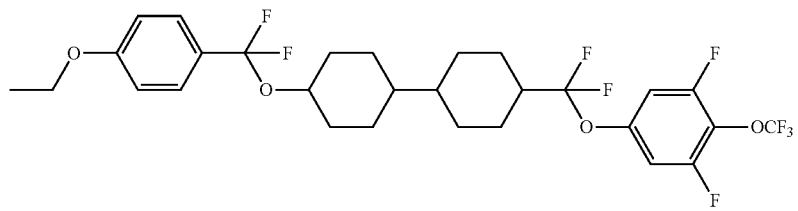
179
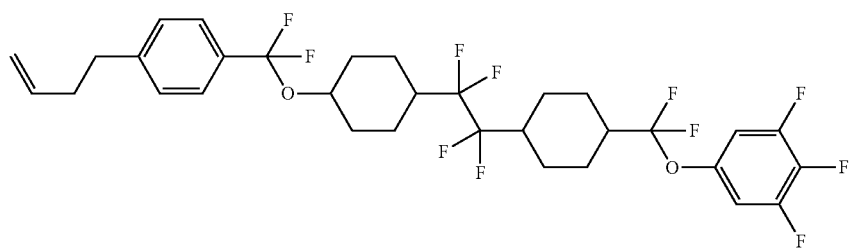

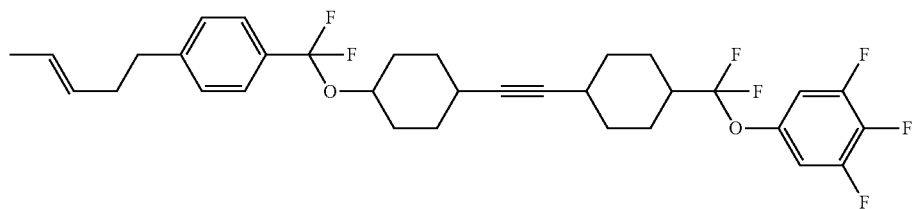
180
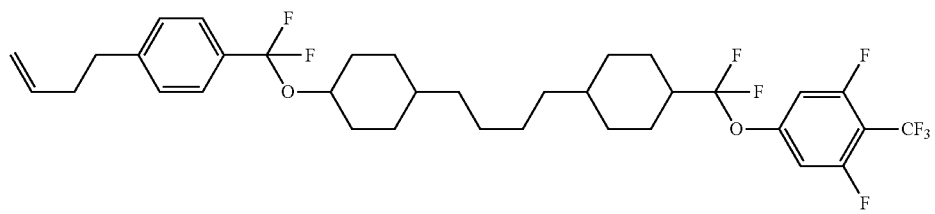
181
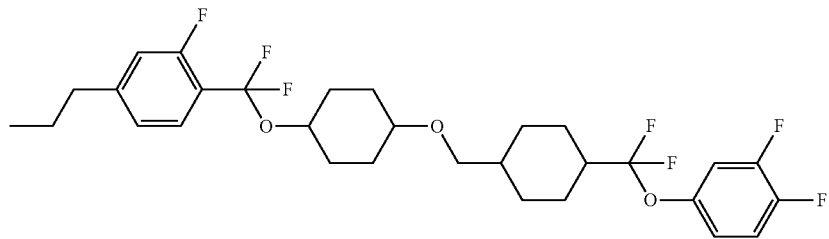
182
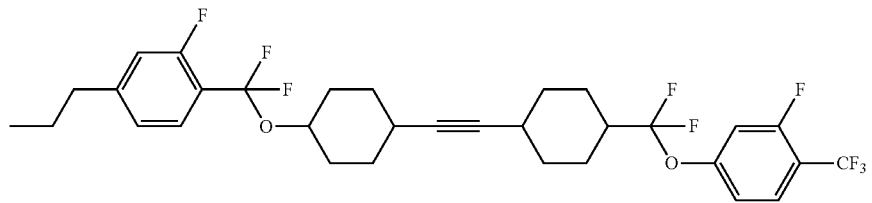
183
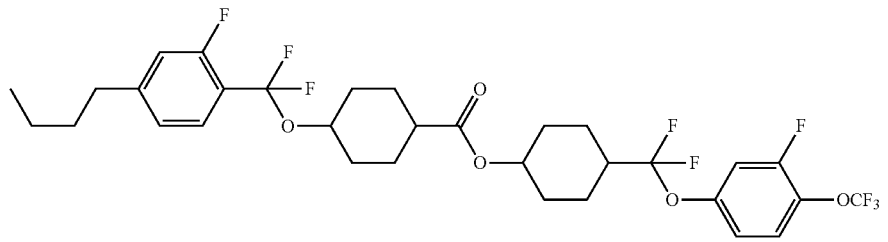
184
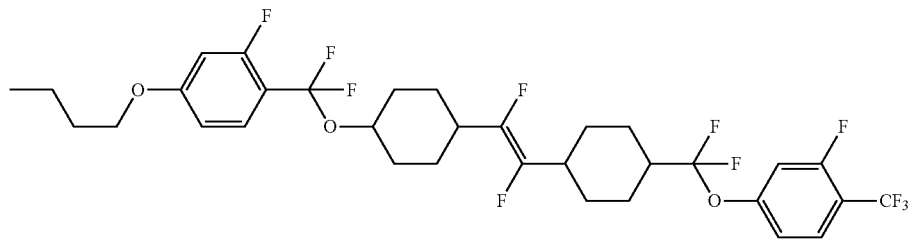
185

186
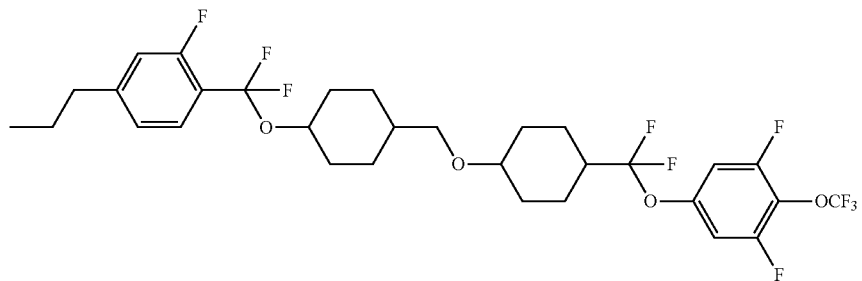
187
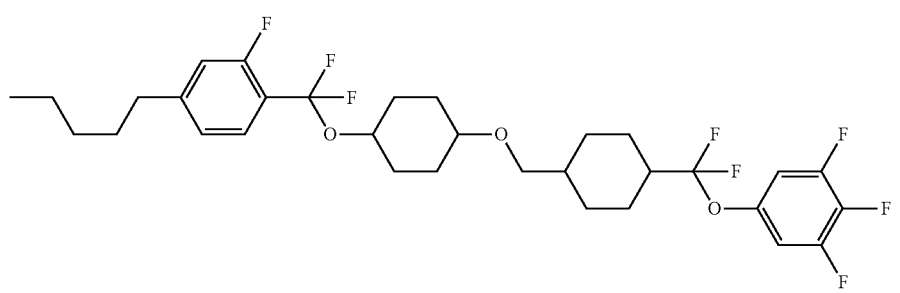
188
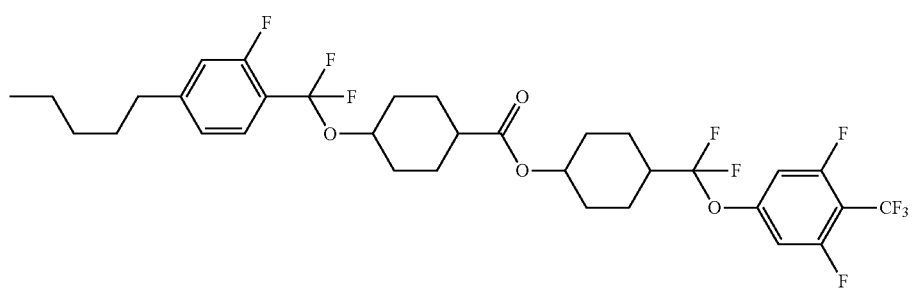
189
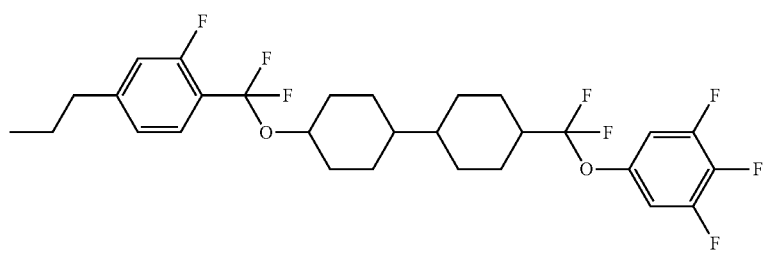
190
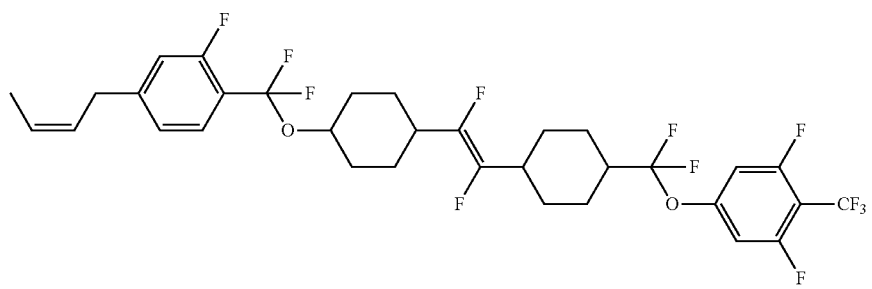
191
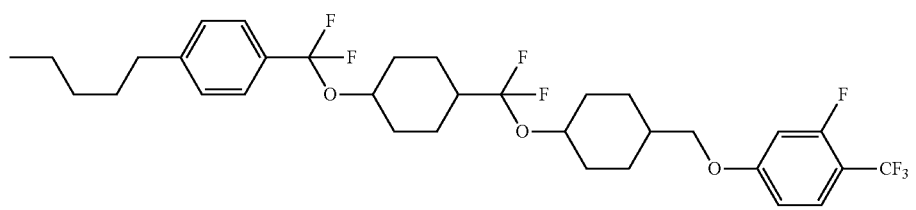

-continued
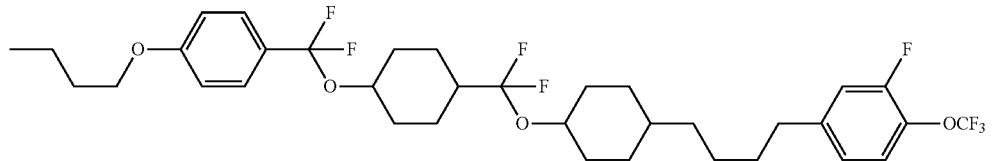
192
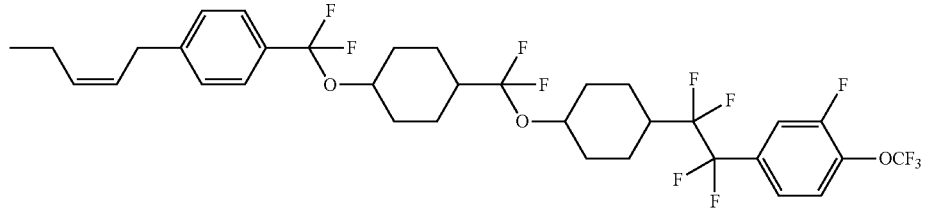
193
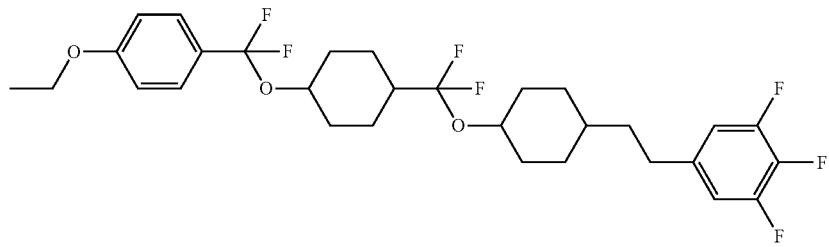
194
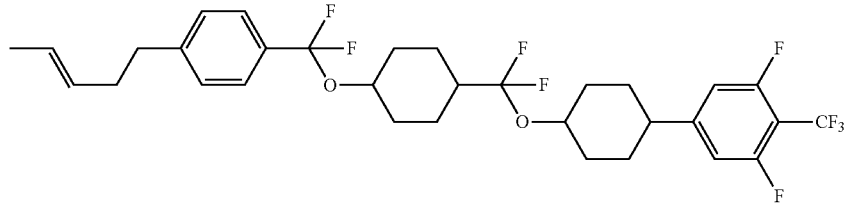
195
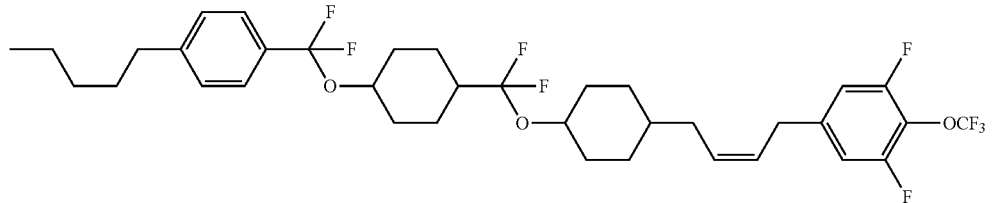
196
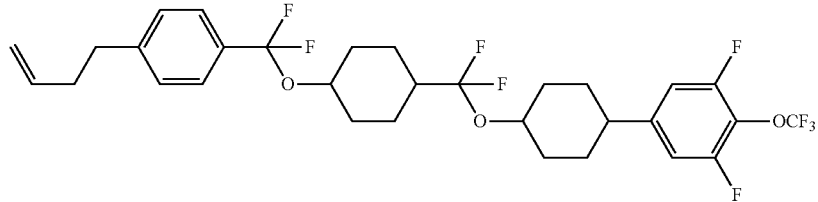
197
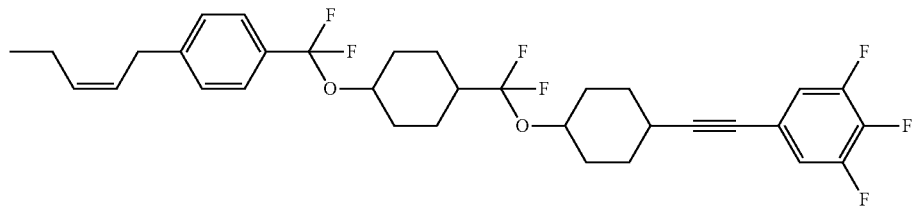
198

199
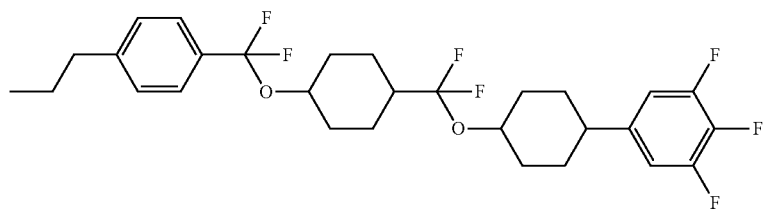
200
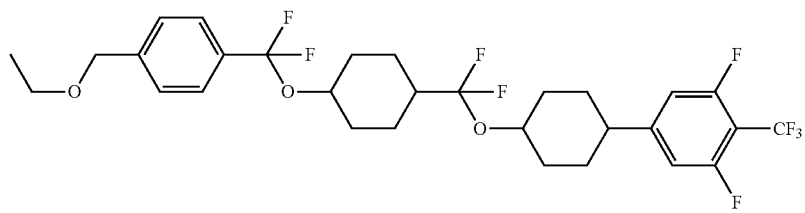
201
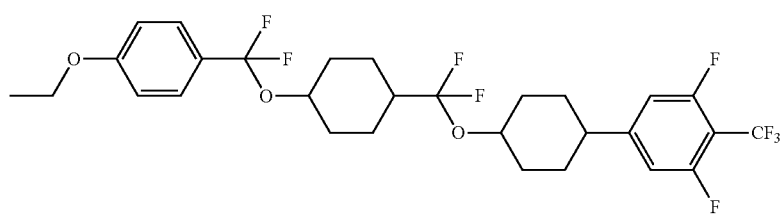
202
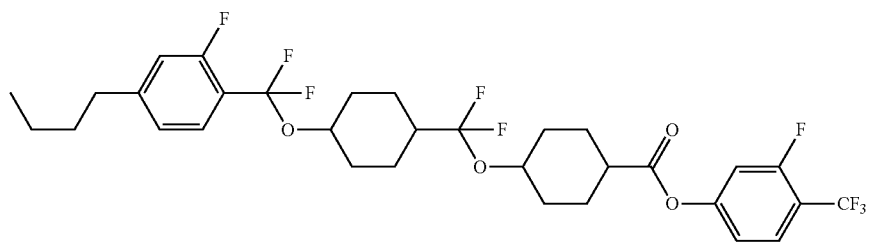
203
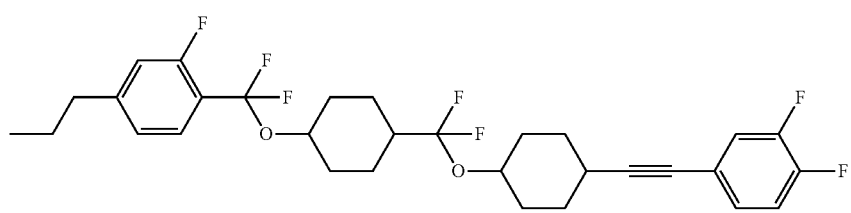
204
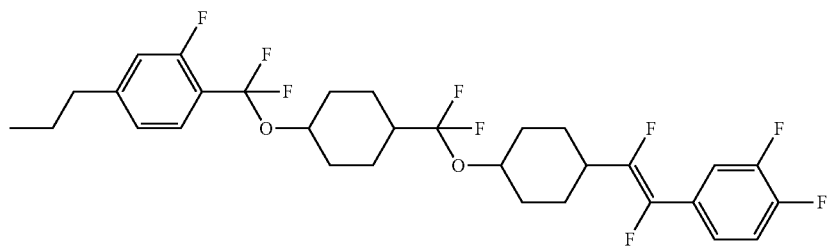
205
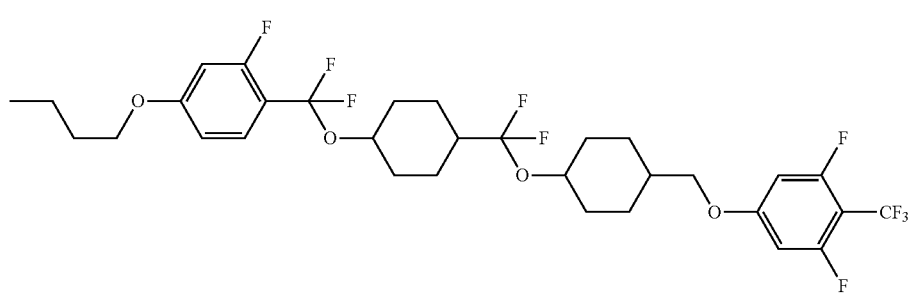

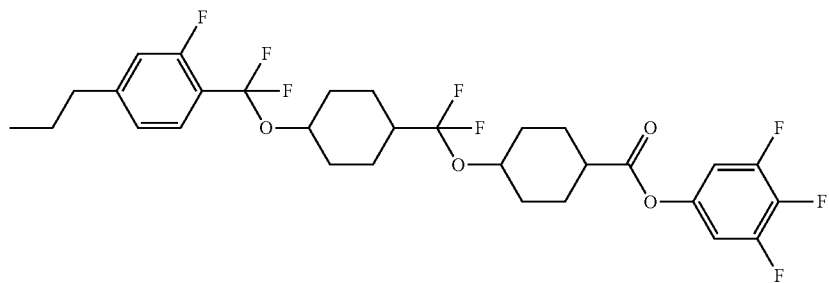
206
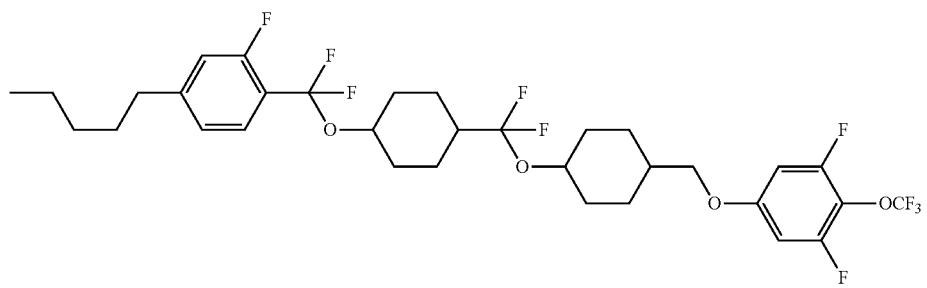
207
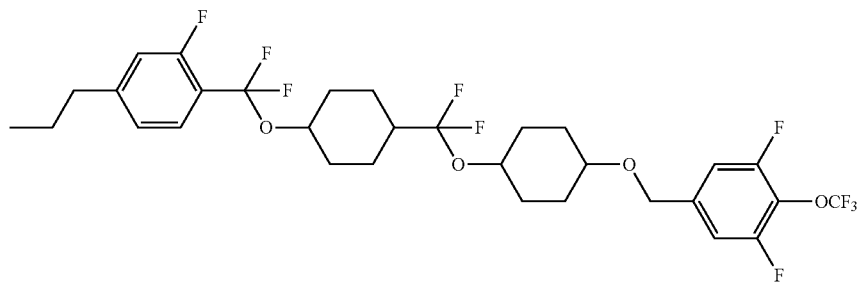
208
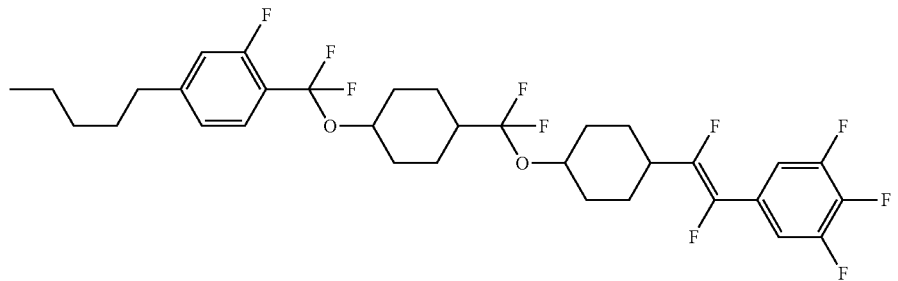
209
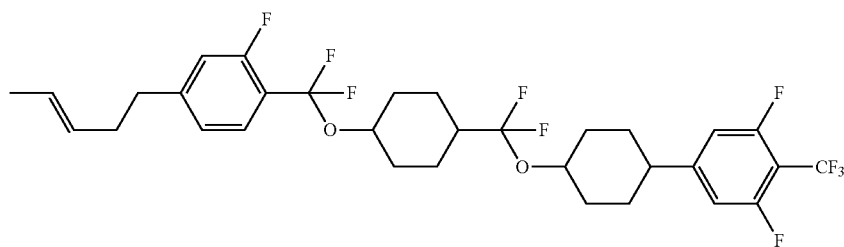
210

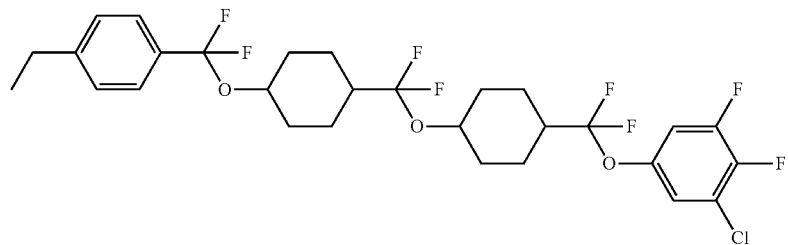 211
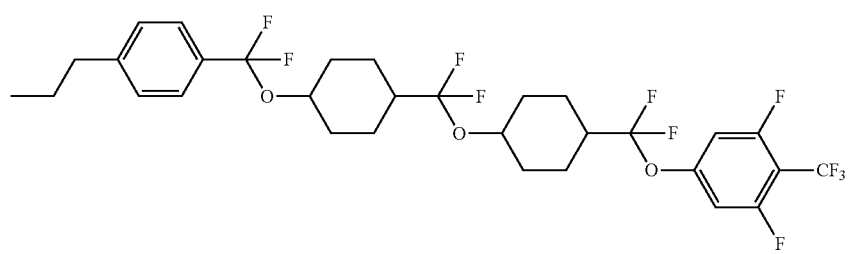 212
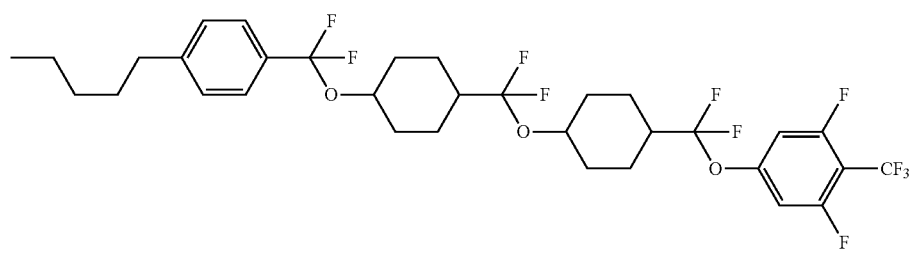 213
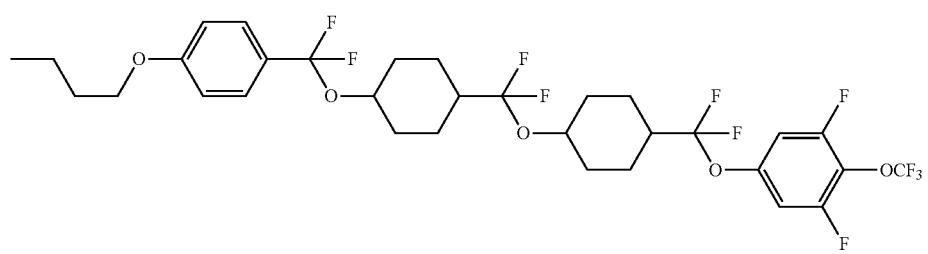 214
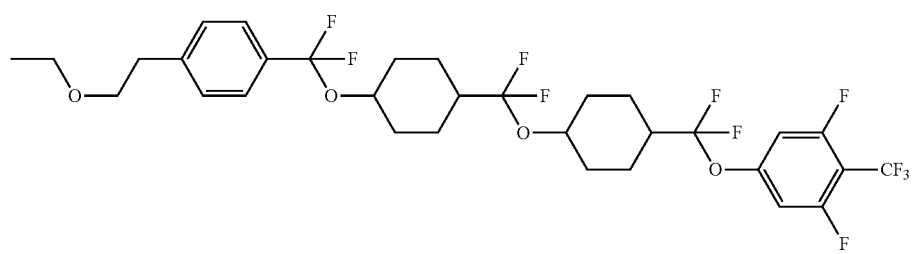 215
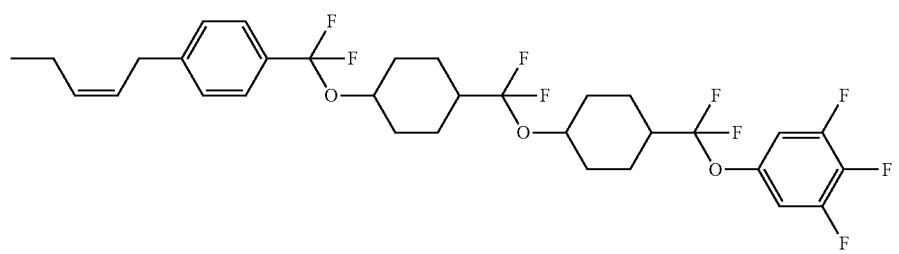 216

-continued
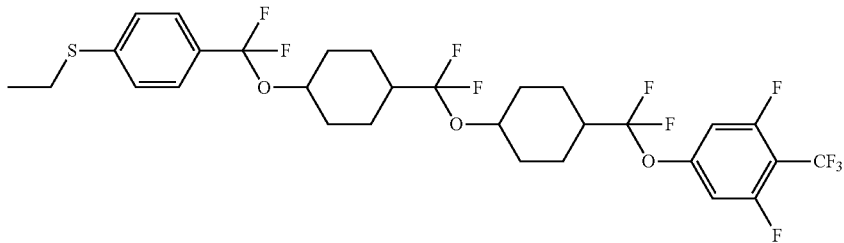
217
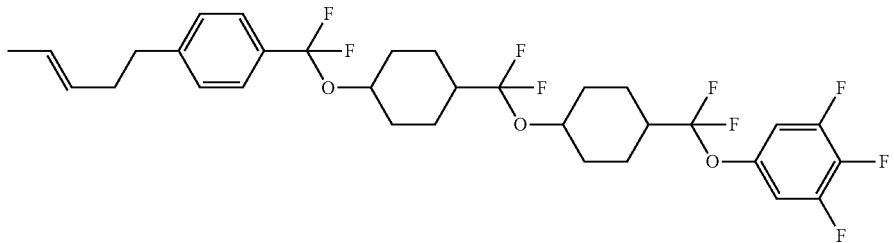
218
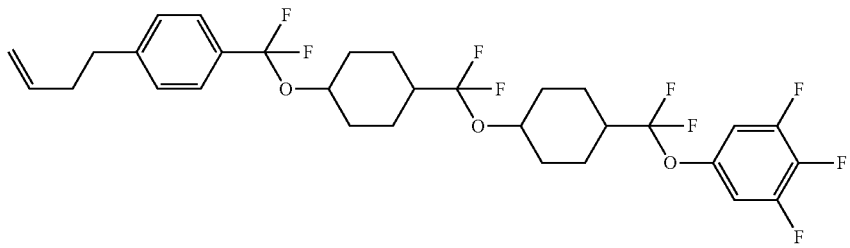
219
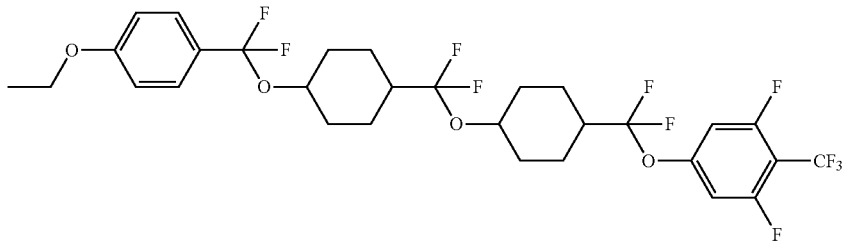
220
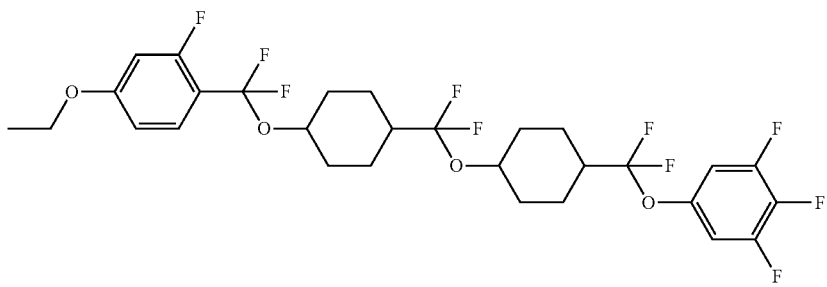
221
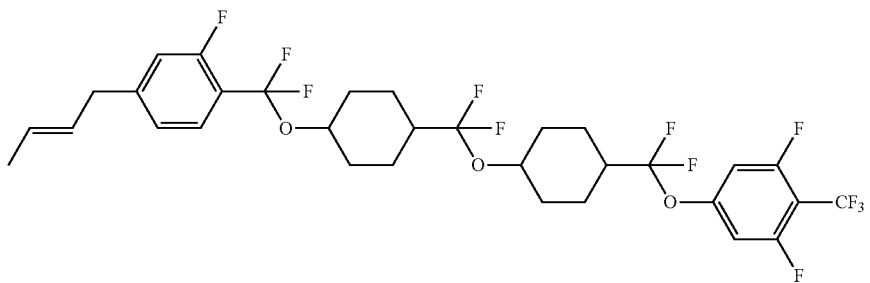
222

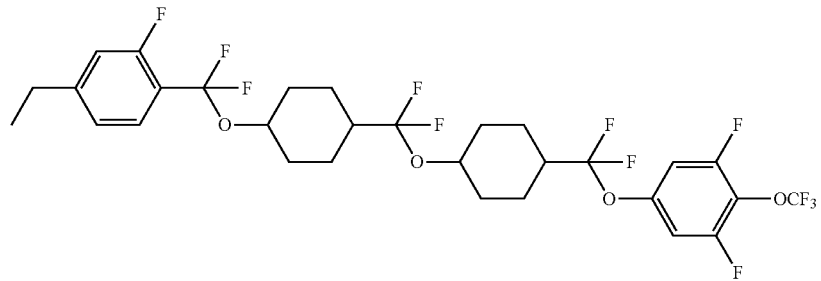
223
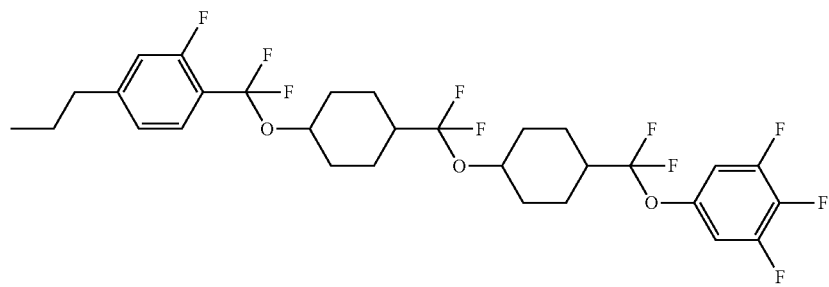
224
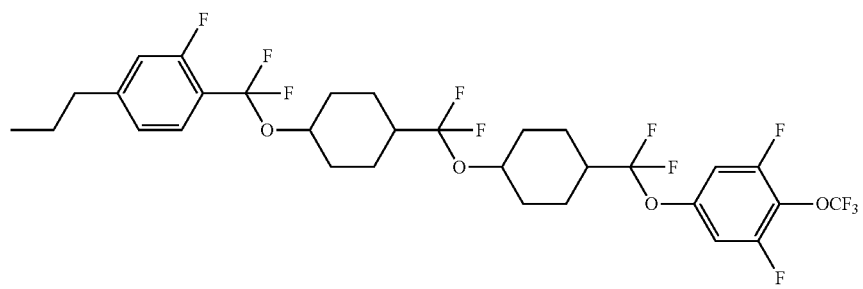
225
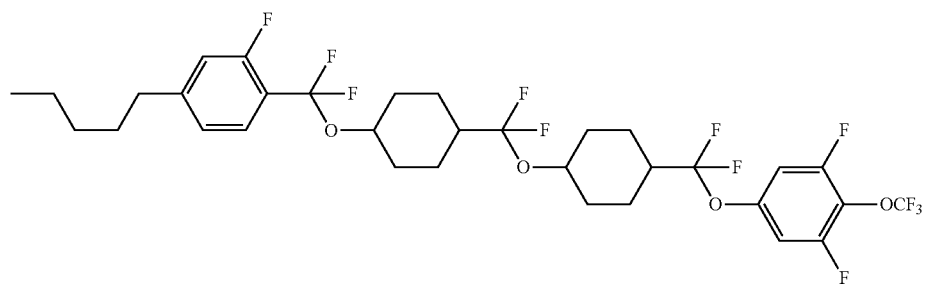
226
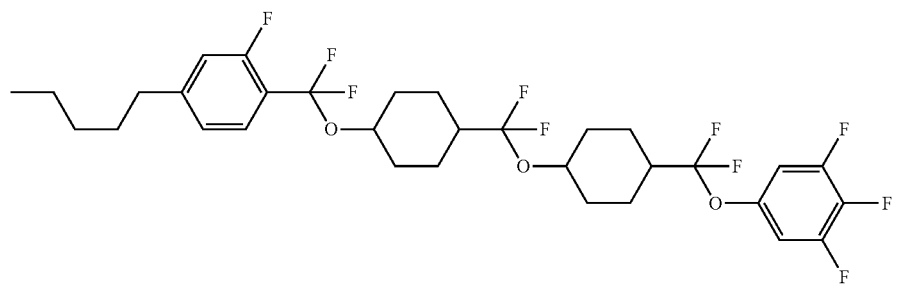
227

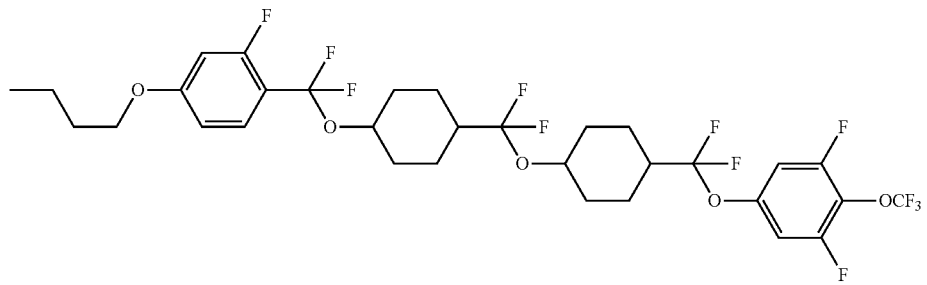
228
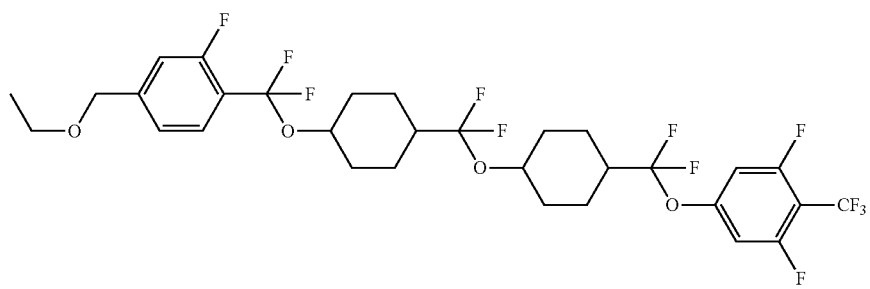
229
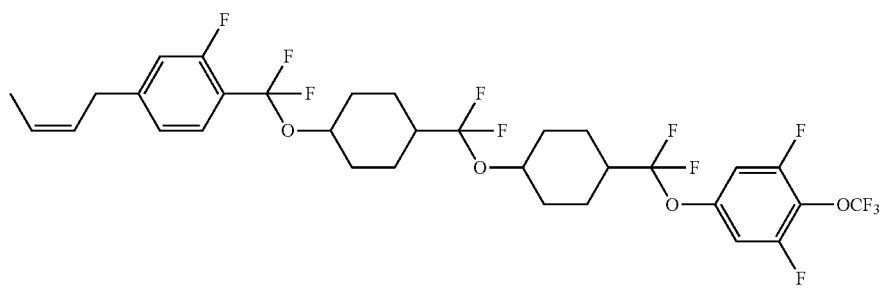
230
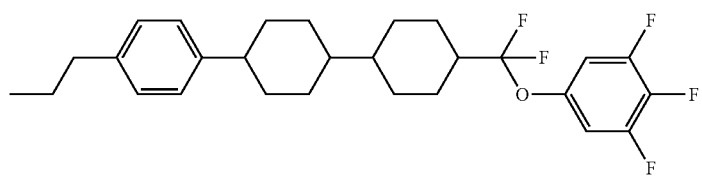
231
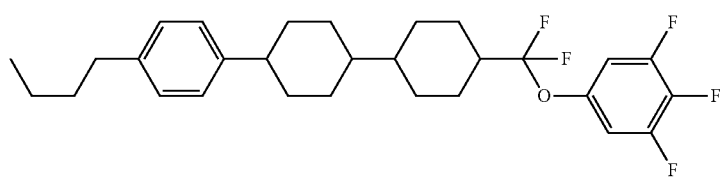
232
C 63.1 SB 93.2 N 192.2 I NI = 139.7;
Δε = 13.5; Δn = 0.104; η = 59 mPa/s.
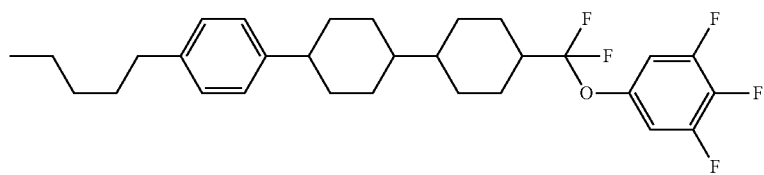
233

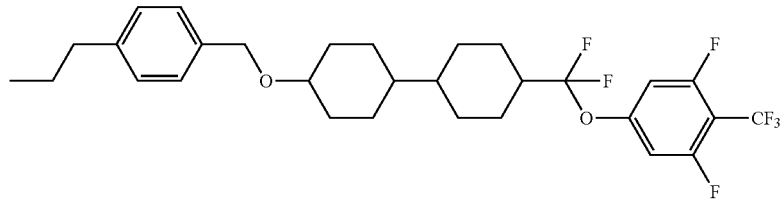
234
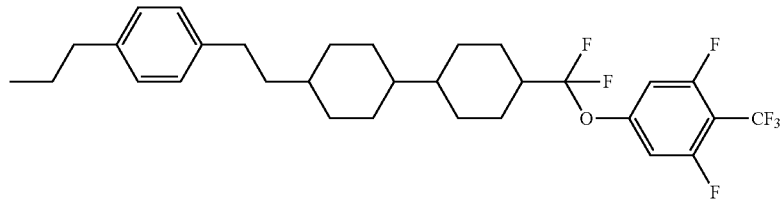
235
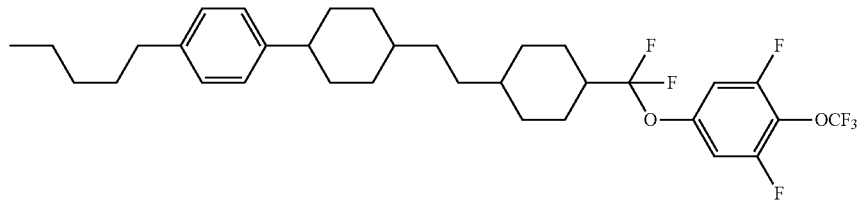
236
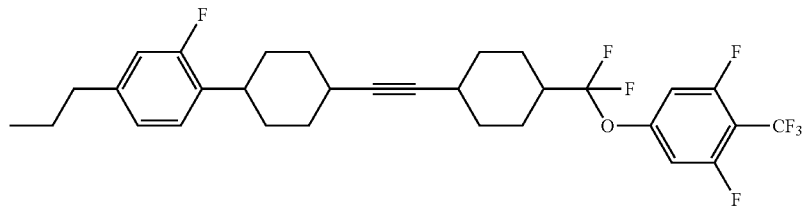
237
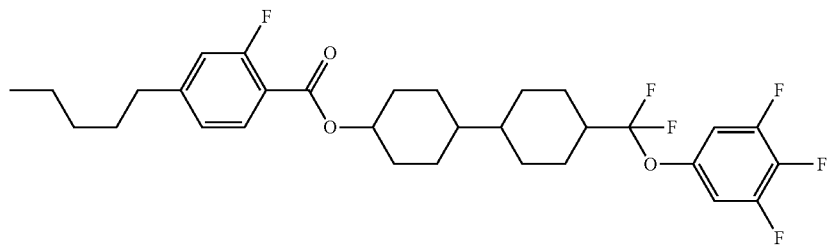
238
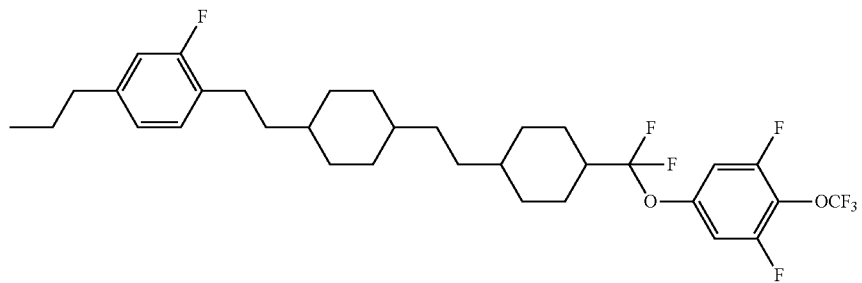
239

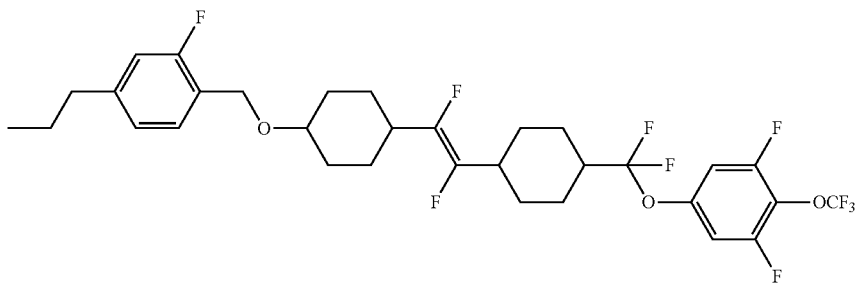

2. Example of Composition

The composition of the invention will be described in detail by way Examples. The invention includes a mixture of a composition in Use Example 1 and a composition in Use Example 2. The invention also includes a mixture of at least two of compositions in Use Examples. The compounds in Use Examples were represented using symbols according to definitions in Table 2 described below. In Table 2, a configuration of 1,4-cyclohexylene is trans. A parenthesized number next to a symbolized compound in the Use Examples represents a chemical formula to which the compound belongs. A symbol (-) means any other liquid crystal compound different from compounds (2) to (15). A proportion (percentage) of the liquid crystal compound is expressed in terms of weight percent (% by weight) based on the weight of the liquid crystal composition. Values of physical properties of the composition are summarized in a last part. The physical properties were measured in accordance with the methods described above, and measured values are directly described (without extrapolation).

TABLE 2

| Method for Description of Compounds using Symbols<br>R—(A$_1$)—Z$_1$— ... —Z$_n$—(A$_n$)—R' | |
|---|---|
| 1) Left-terminal Group R— | Symbol |
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| 2) Right-terminal Group —R' | Symbol |
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n+1}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH=CH—$CF_3$ | —OVCF3 |
| —C≡N | —C |
| 3) Bonding Group —Zn— | Symbol |
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

TABLE 2-continued
Method for Description of Compounds using Symbols
R—(A$_1$)—Z$_1$— . . . —Z$_n$—(A$_n$)—R'
| 4) Ring Structure —An— | Symbol |
|---|---|
|  | H |
|  | B |
| 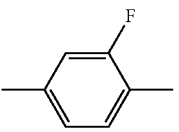 | B(F) |
| 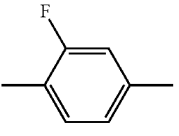 | B(2F) |
| 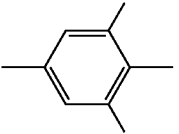 | B(F,F) |
| 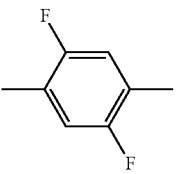 | B(2F,5F) |
| 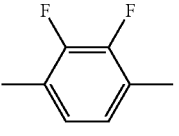 | B(2F,3F) |
| 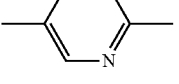 | Py |
| 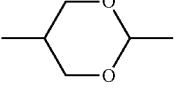 | G |
| 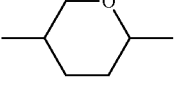 | dh |
| 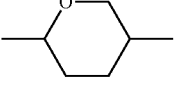 | Dh |

TABLE 2-continued

Method for Description of Compounds using Symbols
R—(A$_1$)—Z$_1$— ... —Z$_n$—(A$_n$)—R'

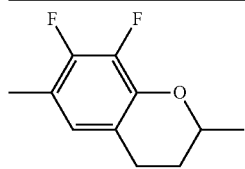  Cro

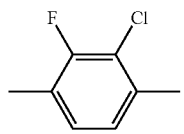  (B(2F,3CL))

5) Examples of Description

Example 1. 3-HH-V

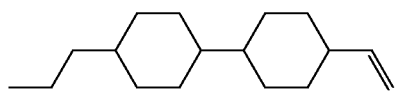

Example 2. 4O-BHHXB(F,F)-F

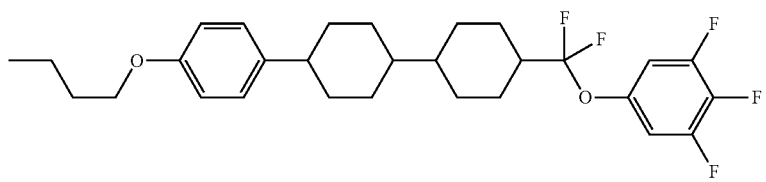 [SMILES: CCCCOc1ccc(C2CCC(C3CCC(C(F)(F)Oc4cc(F)c(F)c(F)c4)CC3)CC2)cc1]

Use Example 1

| | | |
|---|---|---|
| 4O-BHHXB(F,F)-F | (No. 10) | 5% |
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 9% |
| 4-PyBB-F | (6-80) | 9% |
| 5-PyBB-F | (6-80) | 9% |
| 5-HBB(F)B-2 | (4-5) | 9% |
| 5-HBB(F)B-3 | (4-5) | 9% |

NI=98.8° C.; η=40.2 mPa·s; Δn=0.185; Δ∈=8.1.

Use Example 2

| | | |
|---|---|---|
| 3-B(F)HXHB(F,F)-F | (No. 53) | 4% |
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 3% |
| 3-HHB-1 | (3-1) | 9% |
| 3-HHB-O1 | (3-1) | 5% |
| 3-HHB-3 | (3-1) | 15% |
| 3-HHEB-F | (6-10) | 3% |
| 5-HHEB-F | (6-10) | 3% |
| 2-HHB(F)-F | (6-2) | 6% |
| 3-HHB(F)-F | (6-2) | 5% |
| 5-HHB(F)-F | (6-2) | 7% |
| 3-HHB(F,F)-F | (6-3) | 5% |

Use Example 3

| | | |
|---|---|---|
| 3-B(F)XHHB(F,F)-F | (No. 83) | 5% |
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 11% |
| 2-HBB(F)-F | (6-23) | 7% |
| 3-HBB(F)-F | (6-23) | 8% |
| 5-HBB(F)-F | (6-23) | 14% |
| 2-HBB-F | (6-22) | 4% |
| 3-HBB-F | (6-22) | 4% |
| 5-HBB-F | (6-22) | 3% |
| 3-HBB(F,F)-F | (6-24) | 6% |
| 5-HBB(F,F)-F | (6-24) | 8% |

Use Example 4

| | | |
|---|---|---|
| 3-B(F)XHHXB(F,F)-F | (No. 189) | 3% |
| 5-HB-CL | (5-2) | 16% |
| 3-HB-4 | (2-5) | 12% |
| 3-HB-5 | (2-5) | 4% |
| 3-HHB-F | (6-1) | 4% |
| 3-HHB-CL | (6-1) | 3% |
| 4-HHB-CL | (6-1) | 3% |
| 3-HHB(F)-F | (6-2) | 10% |
| 4-HHB(F)-F | (6-2) | 8% |
| 5-HHB(F)-F | (6-2) | 8% |
| 7-HHB(F)-F | (6-2) | 8% |
| 5-HBB(F)-F | (6-23) | 4% |

-continued

| | | |
|---|---|---|
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

Use Example 5

| | | |
|---|---|---|
| 4O-BHHXB(F,F)-F | (No. 10) | 4% |
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 21% |
| 5-HBB(F,F)-F | (6-24) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-5 | (4-1) | 4% |

NI=95.0° C.; p=35.0 mPa·s; Δn=0.114; Δ∈=9.4.

A pitch was 64.9 micrometers when compound (Op-05) was added to the composition described above in a proportion of 0.25% by weight.

Use Example 6

| | | |
|---|---|---|
| 3-B(F)HXHB(F,F)-F | (No. 53) | 5% |
| 5-HB-F | (5-2) | 12% |
| 6-HB-F | (5-2) | 9% |
| 7-HB-F | (5-2) | 7% |
| 2-HHB-OCF$_3$ | (6-1) | 7% |
| 3-HHB-OCF$_3$ | (6-1) | 7% |
| 4-HHB-OCF$_3$ | (6-1) | 7% |
| 5-HHB-OCF$_3$ | (6-1) | 4% |
| 3-HH2B-OCF$_3$ | (6-4) | 4% |
| 5-HH2B-OCF$_3$ | (6-4) | 4% |
| 3-HHB(F,F)-OCF$_2$H | (6-3) | 3% |
| 3-HHB(F,F)-OCF$_3$ | (6-3) | 5% |
| 3-HH2B(F)-F | (6-5) | 3% |
| 3-HBB(F)-F | (6-23) | 10% |
| 5-HBB(F)-F | (6-23) | 7% |
| 5-HBBH-3 | (4-1) | 3% |
| 3-HB(F)BH-3 | (4-2) | 3% |

Use Example 7

| | | |
|---|---|---|
| 3-B(F)XHHB(F,F)-F | (No. 83) | 4% |
| 5-HB-CL | (5-2) | 9% |
| 3-HB-4 | (2-5) | 8% |
| 3-HHB-1 | (3-1) | 5% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 4% |
| 5-HBEB(F,F)-F | (6-39) | 3% |
| 3-HHBB(F,F)-F | (7-6) | 5% |

Use Example 8

| | | |
|---|---|---|
| 3-B(F)XHHXB(F,F)-F | (No. 189) | 5% |
| 3-HB-CL | (5-2) | 6% |
| 5-HB-CL | (5-2) | 4% |
| 3-HHB-OCF$_3$ | (6-1) | 4% |
| 3-H2HB-OCF$_3$ | (6-13) | 5% |
| 5-H4HB-OCF$_3$ | (6-19) | 13% |
| V-HHB(F)-F | (6-2) | 5% |
| 3-HHB(F)-F | (6-2) | 5% |
| 5-HHB(F)-F | (6-2) | 4% |
| 3-H4HB(F,F)-CF$_3$ | (6-21) | 8% |
| 5-H4HB(F,F)-CF$_3$ | (6-21) | 9% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 10% |
| 3-HBEB(F,F)-F | (6-39) | 5% |

Use Example 9

| | | |
|---|---|---|
| 4O-BHHXB(F,F)-F | (No. 10) | 3% |
| 5-HB-CL | (5-2) | 16% |
| 7-HB(F,F)-F | (5-4) | 3% |
| 3-HB-4 | (2-5) | 10% |
| 3-HB-5 | (2-5) | 5% |
| 3-HB-O2 | (2-5) | 15% |
| 3-HHB-1 | (3-1) | 7% |
| 3-HHB-O1 | (3-1) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 4% |

NI=73.8° C.; η=14.9 mPa·s; Δn=0.075; Δ∈=3.1.

Use Example 10

| | | |
|---|---|---|
| 3-B(F)HXHB(F,F)-F | (No. 53) | 4% |
| 5-HB-CL | (5-2) | 3% |
| 7-HB(F)-F | (5-3) | 7% |
| 3-HB-4 | (2-5) | 9% |
| 5-HH-EMe | (2-2) | 23% |
| 3-HHEB-F | (6-10) | 6% |
| 5-HHEB-F | (6-10) | 8% |
| 3-HHEB(F,F)-F | (6-39) | 10% |
| 4-HHEB(F,F)-F | (6-39) | 5% |
| 4-HGB(F,F)-F | (6-103) | 4% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 6% |

Use Example 11

| | | |
|---|---|---|
| 3-B(F)XHHB(F,F)-F | (No. 83) | 3% |
| 3-HB-O1 | (2-5) | 15% |
| 3-HH-4 | (2-1) | 3% |
| 3-HH-V | (2-1) | 5% |
| 3-HB(2F,3F)-O2 | (9-1) | 10% |
| 5-HB(2F,3F)-O2 | (9-1) | 12% |
| 2-HHB(2F,3F)-1 | (10-1) | 10% |
| 3-HHB(2F,3F)-1 | (10-1) | 10% |
| 3-HHB(2F,3F)-O2 | (10-1) | 13% |
| 5-HHB(2F,3F)-O2 | (10-1) | 13% |
| 3-HHB-1 | (3-1) | 6% |

Use Example 12

| | | |
|---|---|---|
| 3-B(F)XHHXB(F,F)-F | (No. 189) | 4% |
| 2-HH-5 | (2-1) | 3% |
| 3-HH-4 | (2-1) | 14% |
| 3-HH-5 | (2-1) | 4% |
| 3-HB-O2 | (2-5) | 12% |
| 3-H2B(2F,3F)-O2 | (9-4) | 14% |
| 5-H2B(2F,3F)-O2 | (9-4) | 14% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 8% |
| 5-HBB(2F,3F)-O2 | (10-7) | 9% |
| 3-HHB-1 | (3-1) | 3% |
| 3-HHB-3 | (3-1) | 4% |
| 3-HHB-O1 | (3-1) | 3% |

Use Example 13

| | | |
|---|---|---|
| 4O-BHHXB(F,F)-F | (No. 10) | 5% |
| 2-HH-3 | (2-1) | 21% |
| 3-HH-4 | (2-1) | 8% |
| 1-BB-3 | (2-8) | 8% |
| 3-HB-O2 | (2-5) | 3% |
| 3-BB(2F,3F)-O2 | (9-3) | 9% |
| 5-BB(2F,3F)-O2 | (9-3) | 5% |
| 2-HH1OB(2F,3F)-O2 | (10-5) | 11% |
| 3-HH1OB(2F,3F)-O2 | (10-5) | 20% |
| 3-HHB-1 | (3-1) | 5% |
| 3-HHB-O1 | (3-1) | 3% |
| 5-B(F)BB-2 | (3-8) | 2% |

NI=78.7° C.; η=16.6 mPa·s; Δn=0.098; Δ∈=−2.9.

Use Example 14

| | | |
|---|---|---|
| 3-B(F)HXHB(F,F)-F | (No. 53) | 5% |
| 2-HH-3 | (2-1) | 16% |
| 7-HB-1 | (2-5) | 10% |
| 5-HB-O2 | (2-5) | 7% |
| 3-HB(2F,3F)-O2 | (9-1) | 15% |
| 5-HB(2F,3F)-O2 | (9-1) | 15% |
| 3-HHB(2F,3CL)-O2 | (10-12) | 4% |
| 4-HHB(2F,3CL)-O2 | (10-12) | 3% |
| 5-HHB(2F,3CL)-O2 | (10-12) | 3% |
| 3-HH1OCro(7F,8F)-5 | (13-6) | 5% |
| 5-HBB(F)B-2 | (4-5) | 9% |
| 5-HBB(F)B-3 | (4-5) | 8% |

Use Example 15

| | | |
|---|---|---|
| 3-B(F)XHHB(F,F)-F | (No. 83) | 4% |
| 1-BB-3 | (2-8) | 10% |
| 3-HH-V | (2-1) | 25% |
| 3-BB(2F,3F)-O2 | (9-3) | 8% |
| 5-BB(2F,3F)-O2 | (9-3) | 5% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 5-B(F)BB-2 | (3-8) | 6% |

Use Example 16

| | | |
|---|---|---|
| 3-B(F)XHHXB(F,F)-F | (No. 189) | 3% |
| 2-HH-3 | (2-1) | 6% |
| 3-HH-V1 | (2-1) | 10% |
| 1V2-HH-1 | (2-1) | 6% |
| 1V2-HH-3 | (2-1) | 7% |
| 3-BB(2F,3F)-O2 | (9-3) | 7% |
| 5-BB(2F,3F)-O2 | (9-3) | 4% |
| 3-H1OB(2F,3F)-O2 | (9-5) | 7% |
| 2-HH1OB(2F,3F)-O2 | (10-5) | 8% |
| 3-HH1OB(2F,3F)-O2 | (10-5) | 19% |
| 3-HDhB(2F,3F)-O2 | (10-3) | 7% |
| 3-HHB-1 | (3-1) | 3% |
| 3-HHB-3 | (3-1) | 2% |
| 2-BB(2F,3F)B-3 | (11-1) | 11% |

Use Example 17

| | | |
|---|---|---|
| 4O-BHHXB(F,F)-F | (No. 10) | 3% |
| 1V2-BEB(F,F)-C | (8-15) | 5% |
| 3-HB-C | (8-1) | 18% |
| 2-BTB-1 | (2-10) | 10% |
| 5-HH-VFF | (2-1) | 30% |
| 3-HHB-1 | (3-1) | 5% |
| VFF-HHB-1 | (3-1) | 8% |
| VFF2-HHB-1 | (3-1) | 9% |
| 3-H2BTB-2 | (3-17) | 4% |
| 3-H2BTB-3 | (3-17) | 4% |
| 3-H2BTB-4 | (3-17) | 4% |

NI=83.4° C.; η=12.8 mPa·s; Δn=0.129; Δ∈=6.1.

Use Example 18

| | | |
|---|---|---|
| 3-B(F)HXHB(F,F)-F | (No. 53) | 4% |
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 3% |
| 3-HHB-1 | (3-1) | 3% |
| V-HHB-1 | (3-1) | 3% |
| V2-BB(F)B-1 | (3-6) | 5% |
| 1V2-BB-F | (3-6) | 3% |
| 3-BB(F,F)XB(F,F)-F | (6-97) | 10% |
| 3-HHBB(F,F)-F | (7-6) | 3% |

Use Example 19

| | | |
|---|---|---|
| 3-B(F)XHHB(F,F)-F | (No. 83) | 3% |
| 3-B(F)XHHXB(F,F)-F | (No. 174) | 2% |
| 3-GB(F)B(F,F)XB(F,F)-F | (7-57) | 4% |
| 3-BB(F)B(F,F)XB(F,F)-F | (7-47) | 3% |
| 4-BB(F)B(F,F)XB(F,F)-F | (7-47) | 6% |
| 5-BB(F)B(F,F)XB(F,F)-F | (7-47) | 3% |
| 3-HH-V | (2-1) | 39% |
| 3-HH-V1 | (2-1) | 6% |
| 3-HHEH-5 | (3-13) | 4% |
| 3-HHB-1 | (3-1) | 4% |
| V-HHB-1 | (3-1) | 5% |
| V2-BB(F)B-1 | (3-6) | 5% |
| 1V2-BB-F | (3-6) | 3% |
| 3-BB(F,F)XB(F,F)-F | (6-97) | 6% |

-continued

| 3-GB(F,F)XB(F,F)-F | (6-113) | 4% |
| 3-HHBB(F,F)-F | (7-6) | 3% |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has excellent physical properties. A liquid crystal composition containing the compound can be widely applied to a liquid crystal display device used for a personal computer, a television and so forth.

What is claimed is:

1. A compound represented by any one of formulas (1a), (1b) or (1c):

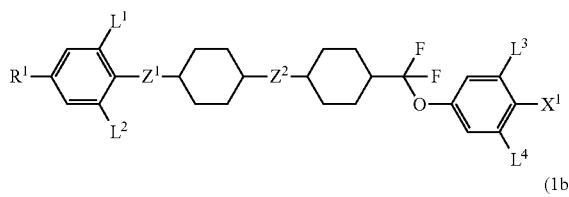
(1a)

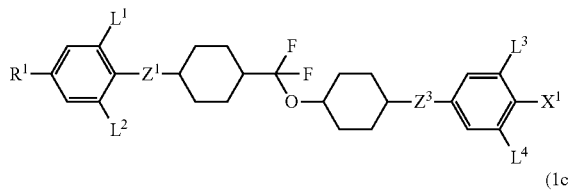
(1b)

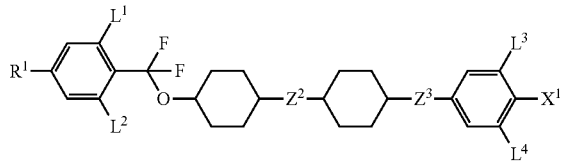
(1c)

wherein, in formulas (1a), (1b) and (1c),
  $R^1$ is alkyl having 1 to 10 carbons, alkoxy having 1 to 10 carbons, alkenyl having 2 to 10 carbons or alkenyloxy having 2 to 10 carbons;
  $Z^1$, $Z^2$ and $Z^3$ are independently a single bond, —COO—, —OCH$_2$, —CH$_2$CH$_2$—, —CF$_2$CF$_2$—, —CF=CF—, —C≡C—, —(CH$_2$)$_4$— or —CH$_2$CH=CHCH$_2$—, and $Z^1$ and $Z^3$ may be independently —CH=CH—;
  $X^1$ is fluorine, —CF$_3$ or —OCF$_3$; and
  $L^1$, $L^2$, $L^3$ and $L^4$ are independently hydrogen, fluorine or chlorine;
  in which, in formula (1a), when $Z^1$ and $Z^2$ are a single bond, $R^1$ is alkoxy having 1 to 10 carbons or alkenyl having 2 to 10 carbons.

2. The compound according to claim 1, wherein, in formulas (1a), (1b) and (1c), $R^1$ is alkenyl having 2 to 10 carbons; $Z^1$, $Z^2$ and $Z^3$ are independently a single bond, —COO— or —OCH$_2$—; $X^1$ is fluorine, —CF$_3$ or —OCF$_3$; and $L^1$, $L^2$, $L^3$ and $L^4$ are independently hydrogen or fluorine.

3. The compound according to claim 1, wherein, in formulas (1a), (1b) and (1c), $R^1$ is alkenyl having 2 to 10 carbons; $Z^1$, $Z^2$ and $Z^3$ are a single bond; $X^1$ is fluorine, —CF$_3$ or —OCF$_3$; and $L^1$, $L^2$, $L^3$ and $L^4$ are independently hydrogen or fluorine.

4. The compound according to claim 1, represented by formula (1a):

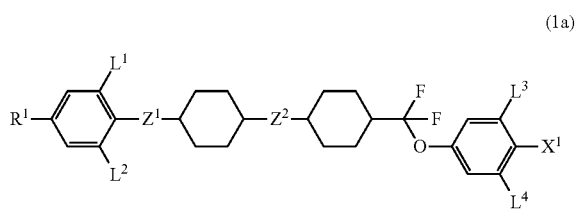
(1a)

wherein, in formula (1a),
  $R^1$ is alkyl having 1 to 10 carbons, alkoxy having 1 to 10 carbons, alkenyl having 2 to 10 carbons or alkenyloxy having 2 to 10 carbons;
  $Z^1$ is a single bond, —COO—, —OCH$_2$— or —CH=CH—, and $Z^2$ is a single bond, —COO— or —OCH$_2$—;
  $X^1$ is —CF$_3$ or —OCF$_3$; and
  $L^1$, $L^2$, $L^3$ and $L^4$ are independently hydrogen or fluorine.

5. The compound according to claim 1, represented by formula (1b) or (1c):

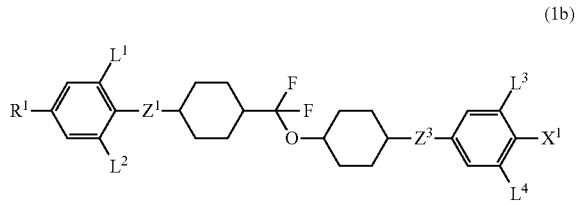
(1b)

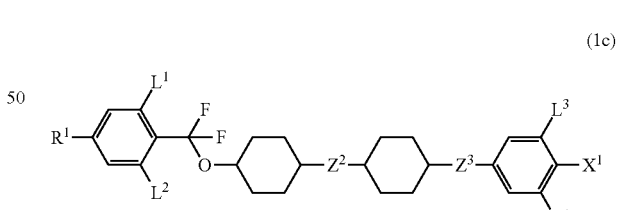
(1c)

wherein, in formulas (1b) and (1c),
  $R^1$ is alkyl having 1 to 10 carbons, alkoxy having 1 to 10 carbons, alkenyl having 2 to 10 carbons or alkenyloxy having 2 to 10 carbons;
  $Z^1$ and $Z^3$ are independently a single bond, —COO—, —OCH$_2$— or —CH=CH—, and $Z^2$ is a single bond, —COO— or —OCH$_2$—;
  $X^1$ is fluorine, —CF$_3$ or —OCF$_3$; and
  $L^1$, $L^2$, $L^3$ and $L^4$ are independently hydrogen or fluorine.

6. The compound according to claim 1, represented by any one of formulas (1g), (1h) and (1i):

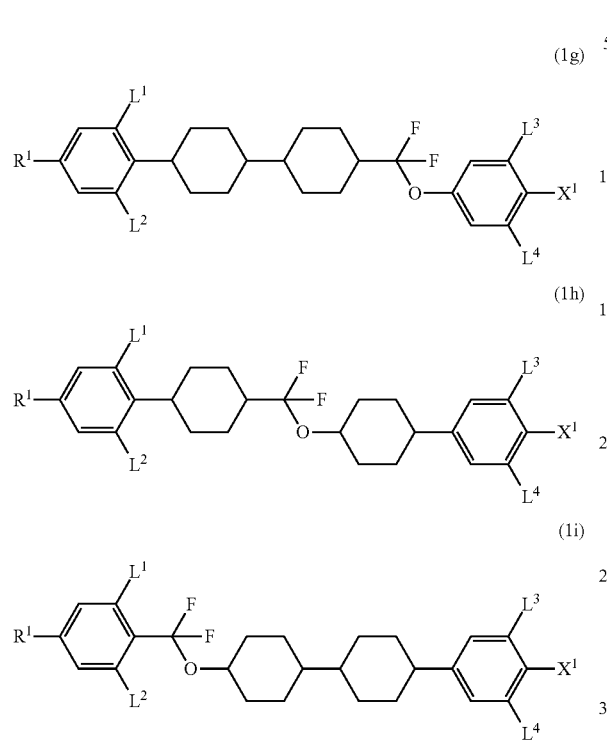

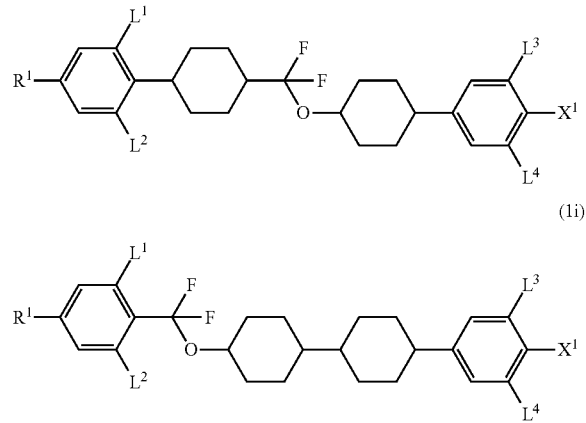

wherein, in formulas (1g), (1h) and (1i), $R^1$ is alkyl having 1 to 10 carbons, alkoxy having 1 to 10 carbons, alkenyl having 2 to 10 carbons or alkenyloxy having 2 to 10 carbons;

$X^1$ is —$CF_3$ or —$OCF_3$;

$L^1$, $L^2$, $L^3$ and $L^4$ are independently hydrogen or fluorine; and in formulas (1h) and (1i), $X^1$ may be fluorine.

7. The compound according to claim 6, represented by formula (1g):

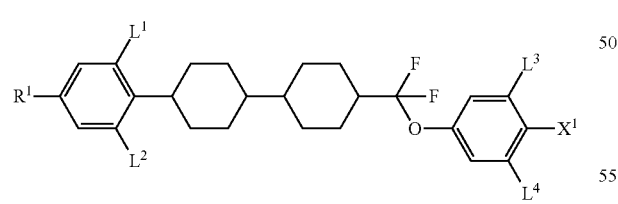

wherein, in formula (1g), $R^1$ is alkyl having 1 to 10 carbons, alkoxy having 1 to 10 carbons, alkenyl having 2 to 10 carbons or alkenyloxy having 2 to 10 carbons;

$X^1$ is —$CF_3$ or —$OCF_3$; and $L^1$, $L^2$, $L^3$ and $L^4$ are independently hydrogen or fluorine.

8. The compound according to claim 6, represented by formula (1h) or (1i):

wherein, in formulas (1h) and (1i), $R^1$ is alkyl having 1 to 10 carbons, alkoxy having 1 to 10 carbons, alkenyl having 2 to 10 carbons or alkenyloxy having 2 to 10 carbons;

$X^1$ is fluorine, —$CF_3$ or —$OCF_3$; and $L^1$, $L^2$, $L^3$ and $L^4$ are independently hydrogen or fluorine.

9. A liquid crystal composition, containing at least one compound according to claim 1.

10. The liquid crystal composition according to claim 9, further containing at least one compound selected from the group of compounds represented by formulas (2) to (4):

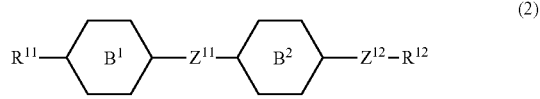

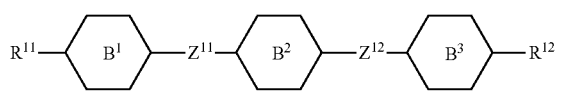

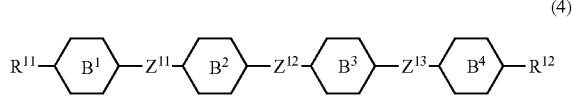

wherein, in formulas (2) to (4), $R^{11}$ and $R^{12}$ are independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

rings $B^1$, $B^2$, $B^3$ and $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH═CH—, —C≡C— or —COO—.

11. The liquid crystal composition according to claim 9, further containing at least one compound selected from the group of compounds represented by formulas (5) to (7):

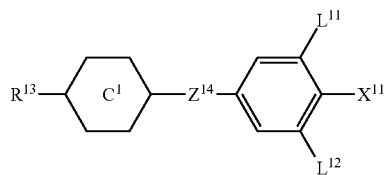
(5)

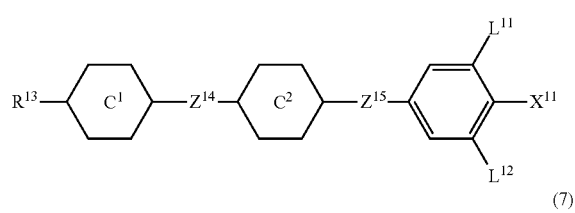
(6)

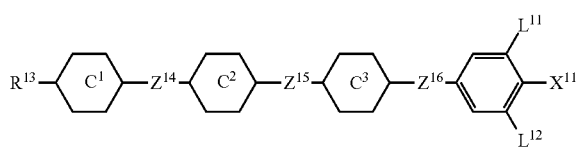
(7)

wherein, in formulas (5) to (7),
R$^{13}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
rings C$^1$, C$^2$ and C$^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{14}$, Z$^{15}$ and Z$^{16}$ are independently a single bond, —CH$_2$CH$_2$—, —CH=CH—, —COO—, —CF$_2$O—, —OCF$_2$—, —CH$_2$O— or —(CH$_2$)$_4$—; and
L$^{11}$ and L$^{12}$ are independently hydrogen or fluorine;
in which, when ring C$^3$ is 1,4-cyclohexylene, ring C$^1$ is 1,4-cyclohexylene, tetrahydropyran-2,5-diyl, 1,3-dioxane-2,5-diyl or pyrimidine-2,5-diyl.

12. The liquid crystal composition according to claim 9, further containing at least one compound selected from the group of compounds represented by formula (8):

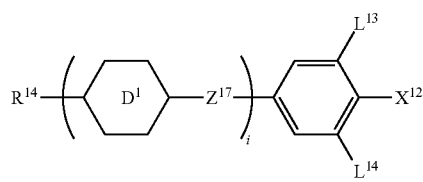
(8)

wherein, in formula (8),
R$^{14}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
X$^{12}$ is —C≡N or —C≡C—C≡N;
ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl, and when a plurality of rings D$^1$ exist, rings D$^1$ may be identical or different;
Z$^{17}$ is a single bond, —CH$_2$CH$_2$—, —C≡C—, —COO—, —CF$_2$O—, —OCF$_2$— or —CH$_2$O—, and when a plurality of Z$^{17}$ exist, Z$^{17}$ may be identical or different;
L$^{13}$ and L$^{14}$ are independently hydrogen or fluorine; and
i is 1, 2, 3 or 4.

13. The liquid crystal composition according to claim 9, further containing at least one compound selected from the group of compounds represented by formulas (9) to (15):

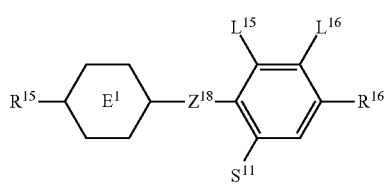
(9)

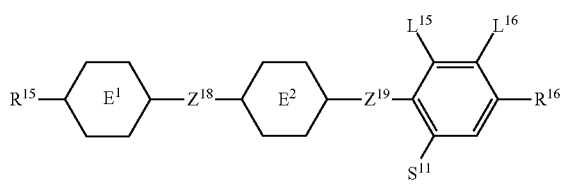
(10)

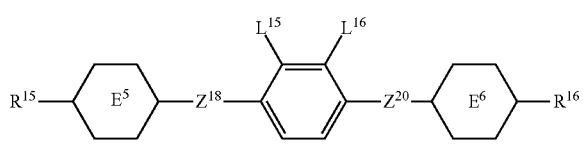
(11)

-continued

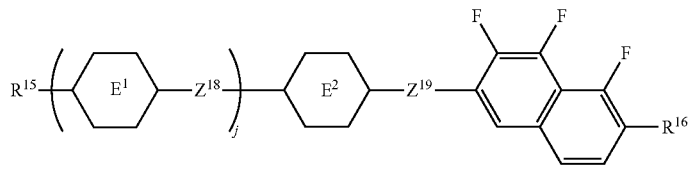
(12)

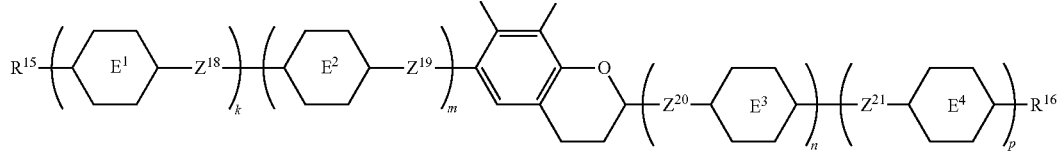
(13)

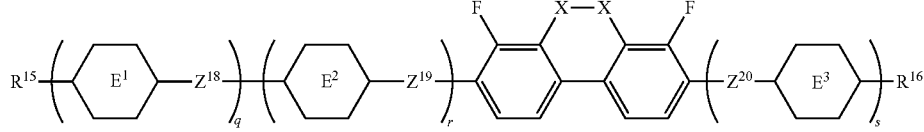
(14)

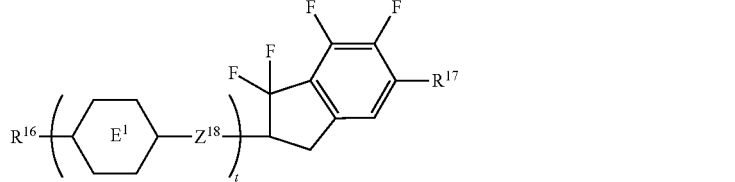
(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

$R^{17}$ is hydrogen, fluorine, alkyl having 1 to 10 carbons or alkenyl having 2 to 10 carbons, and in the alkyl and the alkenyl, at least one —$CH_2$— may be replaced by —O—, and at least one piece of hydrogen may be replaced by fluorine;

rings $E^1$, $E^2$, $E^3$ and $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl, and when a plurality of rings $E^1$, $E^2$, $E^3$ and $E^4$ exist, rings $E^1$, $E^2$, $E^3$ and $E^4$ may be identical or different;

rings $E^5$ and $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—, and when a plurality of $Z^{18}$, $Z^{19}$, $Z^{20}$ and $Z^{21}$ exist, $Z^{18}$, $Z^{19}$, $Z^{20}$ and $Z^{21}$ may be identical or different;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

14. The liquid crystal composition according to claim 9, further containing at least one additive selected from the group consisting of a polymerizable compound, a polymerization initiator, a polymerization inhibitor, an optically active compound, an antioxidant, an ultraviolet light absorber, a light stabilizer, a heat stabilizer, a dye and an antifoaming agent.

15. A liquid crystal display device including the liquid crystal composition according to claim 9.

* * * * *